US008110672B2

(12) United States Patent
Stephanopoulos et al.

(10) Patent No.: US 8,110,672 B2
(45) Date of Patent: Feb. 7, 2012

(54) PROMOTER ENGINEERING AND GENETIC CONTROL

(75) Inventors: Gregory Stephanopoulos, Winchester, MA (US); Hal S. Alper, Cambridge, MA (US); Curt Fischer, Cambridge, MA (US); Elke Nevoigt, Berlin (DE)

(73) Assignee: Massachusetts Institute of Technology, Cambridge, MA (US)

( * ) Notice: Subject to any disclaimer, the term of this patent is extended or adjusted under 35 U.S.C. 154(b) by 44 days.

(21) Appl. No.: 11/411,212

(22) Filed: Apr. 26, 2006

(65) Prior Publication Data

US 2007/0009932 A1 Jan. 11, 2007

Related U.S. Application Data

(60) Provisional application No. 60/675,081, filed on Apr. 27, 2005, provisional application No. 60/677,327, filed on May 4, 2005.

(51) Int. Cl.
*C07H 21/04* (2006.01)
*C40B 40/02* (2006.01)
*C40B 40/06* (2006.01)
*C40B 20/08* (2006.01)

(52) U.S. Cl. ............. 536/24.1; 506/6; 506/14; 506/16

(58) Field of Classification Search ................ 536/24.1; 506/6, 14, 16
See application file for complete search history.

(56) References Cited

U.S. PATENT DOCUMENTS

| | | | |
|---|---|---|---|
| 4,683,195 A | | 7/1987 | Mullis et al. |
| 5,030,563 A | * | 7/1991 | Schendel et al. .............. 435/69.8 |
| 5,654,169 A | * | 8/1997 | Oppenheim et al. .......... 435/69.1 |
| 5,726,039 A | * | 3/1998 | Oppenheim et al. .......... 435/69.1 |
| 6,207,384 B1 | | 3/2001 | Mekalanos et al. |
| 6,472,177 B1 | * | 10/2002 | Szybalski et al. ............. 435/69.1 |
| 6,689,601 B2 | | 2/2004 | Koffas et al. |
| 6,969,595 B2 | | 11/2005 | Brzostowicz |
| 7,018,833 B2 | * | 3/2006 | Sykes et al. ................. 435/320.1 |
| 7,232,666 B2 | | 6/2007 | Sharpe |
| 2002/0051998 A1 | | 5/2002 | Schmidt-Dannert et al. |
| 2004/0219629 A1 | * | 11/2004 | Cheng et al. .................... 435/67 |
| 2005/0003354 A1 | * | 1/2005 | Wilkinson et al. ................ 435/6 |

FOREIGN PATENT DOCUMENTS

| | | | |
|---|---|---|---|
| WO | PCT/US95/14692 | | 8/1996 |
| WO | WO 9807846 | | 2/1998 |
| WO | WO 02/18617 | | 3/2002 |
| WO | WO 2006116400 | * | 4/2006 |

OTHER PUBLICATIONS

Lutz et al., 1997, Independent and tight regulation of transcriptional units in *Escherichia coli* via the LacR/O, the TetR/O, and AraC/I1-I2 regulatory elements, Nucleic Acids Research, 25(6): 1203-1210.*
U.S. Appl. No. 10/997,308, filed Mar. 16, 2006, Sharpe.
Hunter et al. (1994) "Introduction of new carotenoids into the bacterial photosynthetic apparatus by combining the carotenoid biosynthetic pathways of *Erwinia herbicola* and *Rhodobacter sphaeroides*." J. Bact. 176:3692-3697.
Biery et al. (2000) "A simple in vitro Tn7-based transposition system with low target site selectivity for genome and gene analysis." Nucl Acid Res 28:1067-1077.
Devine et al. (1997) "A transposon-based strategy for sequencing repetitive DNA in eukaryotic genomes." Genome Res. 7:551-563.
Fabret et al. (2000) "Efficient gene targeted random mutagenesis in genetically stable *Escherichia coli* strains." Nucl Acid Res, 28, 1-5.
Szybalska et al., Proc. Natl. Acad. Sci. USA, 48:2026-2034 (1962).
K. Y. San, G. N. Bennett, C. H. Chou, A. A. Aristidou, *Ann NY Acad Sci* 721, 268-276 (May 2, 1994).
Toyama, H., et al., FEMS Microbiol. Lett., 166:1 7 (1998).
Ward et al., 1982, Photochem. Photobiol., 35: 803-808.
Levine et al., 1982, Comp. Biochem. Physiol.,72B: 77-85.
Wigler et al., Cell, 11:223 (1977).
Wigler et al., Natl. Acad. Sci. USA, 77:3567 (1980).
Wu et al., Biotherapy, 3:87-95 (1991).
Yoshida, T., et al., Biotechnol. Lett., 23: 787-791 (2001).
S. Mnaimneh et al., *Cell* 118, 31-44 (Jul. 9, 2004).
A. Khlebnikov, O. Risa, T. Skaug, T. A. Carrier, J. D. Keasling, *J Bacteriol* 182, 7029-34 (Dec. 2000).
D. A. Siegele, J. C. Hu, *Proc Natl Acad Sci U S A* 94, 8168-72 (Jul. 22, 1997).
Isabelle Meynial-Salles, Marguerite A. Cervin, and Philippe Soucaille, "New Tool for Metabolic Pathway Engineering in *Escherichia coli*: One-Step Method to Modulate Expression of Chromosomal Genes", Applied and Environmental Microbiology, Apr. 2005, p. 2140-2144.
L. Zhou, X. H. Lei, B. R. Bochner, B. L. Wanner, *J Bacteriol* 185, 4956-72 (Aug. 2003).
K. Nishino, Y. Inazumi, A. Yamaguchi, *J Bacterial* 185, 2667-72 (Apr. 2003).
P. R. Jensen, K. Hammer, *Appl Environ Microbiol* 64, 82-7 (Jan. 1998).
C. M. Jorgensen, K. Hammer, P. R. Jensen, J. Martinussen, *Eur J Biochem* 271, 2438-45 (Jun. 2004).
Lutz et al., Independent and tight regulation of transcriptional units in *Escheria coli* via the LacR/O, the TetR/O and AraC/I1-I2 regulatory elements. Nucleic Acids Research. vol. 25(6): 1203-1210; 1997.
Qian et al., Construction of tetR-integrated *Salmonella enterica* serovar Typhi CVD908 strain that tightly controls expression of the major Merozoite surface protein of *Plasmodium falciparum* for applications in human vaccine production. Infection and Immunity, vol. 70(4): 2029-2038; 2002.
Anderson et al., Simultaneous fluorescence-activated cell sorter analysis of two distinc transcriptional elements within a single cell using engineered green fluorescent proteins PNAS vol. 93: 8508-8511; 1996.
Molesh et al., Quantitive analysis of CD34+ stem cells using RE-PCR on whole cells PCR Methods and Applications. vol. 3: 278-284; 1994.
Miller et al., An improved GFP cloning cassette designed for prokaryotic transcriptional fusions. Gene. vol. 191: 149-153; 1997.

* cited by examiner

*Primary Examiner* — Amber D. Steele
(74) *Attorney, Agent, or Firm* — Pearl Cohen Zedek Latzer, LLP; Mark S. Cohen

(57) ABSTRACT

The present invention relates to expression cassettes libraries of expression vectors comprising the same, wherein each vector comprises at least one gene of interest and a promoter operatively linked thereto wherein each promoter comprises a nucleic acid, whose sequence is randomly mutated with respect to that of another in the library and cells comprising the same. Methods utilizing either the libraries or cells of this invention, in optimizing gene expression, protein expression, or optimized gene or protein delivery are described.

52 Claims, 8 Drawing Sheets

PROMOTER ENGINEERING AND GENETIC CONTROL

CROSS-REFERENCE TO RELATED APPLICATIONS

This Application claims the benefit of U.S. Provisional Application Ser. No. 60/675,081, filed Apr. 27, 2005 and U.S. Provisional Application Ser. No. 60/677,327, filed May 4, 2005, both of which are fully incorporated by reference herein.

FIELD OF THE INVENTION

This invention provides constructs or expression cassettes comprising promoters of varying strength, operatively linked to at least one gene of interest and cells comprising the same. Methods utilizing the libraries or cells of this invention, in optimizing gene expression, protein expression, or optimized gene or protein delivery are described.

BACKGROUND OF THE INVENTION

Protein engineering via directed evolution and gene shuffling has been extensively applied for the systematic improvement of protein properties such as antibody binding affinity, enzyme regulation, and increased or diverse substrate specificity. A similar approach whereby continuously improved mutants are generated along a selection-defined trajectory in the sequence space can also be applied for the systematic improvement or modification of other types of biological sequences, e.g. ribozymes. We show here that promoters can also be engineered via directed evolution to achieve precise strengths and regulation, and, by extension, can constitute libraries exhibiting broad ranges of genetic control.

Typically, the deletion and the strong over-expression of genes have been the principal strategies for elucidation of gene function. These two methods sample the continuum of gene expression at only a few discrete points, determined by experimental feasibility and not necessarily biological significance. Thus, the full dependency of phenotype on gene expression may not be accessible due to the limitations inherent in these methods. Despite prior attempts, no previous work has developed a fully-characterized, homogeneous, broad-range, functional promoter library and demonstrated its applicability to the analysis of such a genetic control.

While inducible promoters allow for a continuous control of expression at the macroscopic level, practical applications of these systems are limited by prohibitive inducer costs, hypersensitivity to inducer concentration, and transcriptional heterogeneity at the single-cell level. The latter factor in particular, can limit the effect of inducers in a culture to a simple increase of the number of cells expressing the gene of interest instead of the overexpression of the gene in all cells. Inducible systems are suitable in certain applications (e.g. recombinant protein overproduction); however, the elucidation of gene function and genetic control on phenotype requires well characterized promoter libraries which are homogeneous at the single cell level.

SUMMARY OF THE INVENTION

The invention provides, in one embodiment, a library of expression vectors, each vector comprising at least one gene of interest and a promoter operatively linked thereto, wherein each promoter comprises a nucleic acid, whose sequence is randomly mutated with respect to that of another in the library.

According to this aspect of the invention, and in one embodiment, the gene of interest encodes an enzyme, which, in another embodiment, is involved in a metabolic pathway. In one embodiment, the mutations in each promoter result in varying promoter strength, which, in one embodiment, may vary between 100-200-fold. In another embodiment, the vector comprises sequences which allow for stable integration of the promoter and the gene of interest in the genome of a cell into which the vector is introduced.

In another embodiment, this invention provides a plurality of cells comprising the library of expression vectors of this invention.

According to this aspect of the invention, and in one embodiment, each cell comprises a vector of the library, which is stably integrated within the genome of the cell. In one embodiment, the cells do not endogenously express, or have been engineered such that they do not endogenously express the gene of interest.

In one embodiment, this invention provides a method of determining an optimized level of gene expression for a gene of interest, the method comprising
  contacting a plurality of cells with a library of expression vectors, each vector comprising at least one gene of interest and a promoter operatively linked thereto, wherein each promoter comprises a nucleic acid, whose sequence is randomly mutated with respect to that of another in said library, and wherein relative changes in expression level of said gene of interest are a function of the mutation in said promoter sequence;
  detecting said relative changes in expression level; and
  identifying a cell from said plurality of cells with a desired expression level,
thereby being a method of determining an optimized level of gene expression for a gene of interest.

According to this aspect of the invention, and in one embodiment, the vectors comprise sequences which allow for stable integration of the promoter and the gene of interest in the genomes of said cells.

In another embodiment, each vector in the library provides a consistent level of expression of the gene of interest, which, in another embodiment, is verified via at least two different methods. In one embodiment, the methods verify expression at a single cell level, and in another embodiment, may comprise fluorescent activated cell sorting analysis, fluorescence microscopy, or a combination thereof.

In another embodiment, the method further comprises identifying the promoter within the cell. In another embodiment, this invention provides a method of optimized protein delivery to a subject, comprising administering to a subject a vector comprising the promoter identified herein.

In another embodiment, this invention provides a cell with a desired expression level of a gene of interest, identified by a method of this invention.

In one embodiment, the cell does not endogenously express, or has been engineered such that it does not endogenously express said gene of interest.

In another embodiment, this invention provides a method of optimized protein delivery to a subject, comprising administering to said subject a cell which expresses an optimized level of the protein, identified via a method of this invention.

In one embodiment, this invention provides an isolated nucleic acid comprising a mutated $PL_{teto-1}$ promoter, wherein said mutated $PL_{teto-1}$ promoter has a sequence comprising:
  a replacement of a/an:
   a) T with a C at nucleotide position 12, 38, 39, 46, 52, 58, 60, 72, 73, 76, 79, 89, 99, 102, 108, 109, 114, 118, 120, 121, 127, or 133;
   b) A with G at nucleotide position 12, 15, 16, 18, 19, 20, 26, 32, 35, 37, 39, 40, 41, 48, 49, 50, 51, 53, 59, 65, 81, 87, 94, 97, 101, 105, 107, 119, 122, 126, 128, 130 or 138;
   c) C with A at nucleotide position 21;

d) A with C at nucleotide position 23, 62, 87, 101, 105, 113, 126, or 128;
e) T with A at nucleotide position 24;
f) C with T at nucleotide position 31 or 135;
g) A with T at nucleotide position 49, 51, 62, or 87;
h) G with A at nucleotide position 64, 67, 86, 98, 100, 125, 129 or 131;
i) T with G at nucleotide 109;
a deletion of nucleotide:
a) T at position 24 or 25;
b) T at position 28;
an insertion of nucleotide:
c) C between nucleotide positions 88 and 89;
d) T between nucleotide positions 96 and 97;
or any combination thereof, of the sequence as set forth in SEQ ID NO: 34.

DETAILED DESCRIPTION OF THE INVENTION

Figure 1:
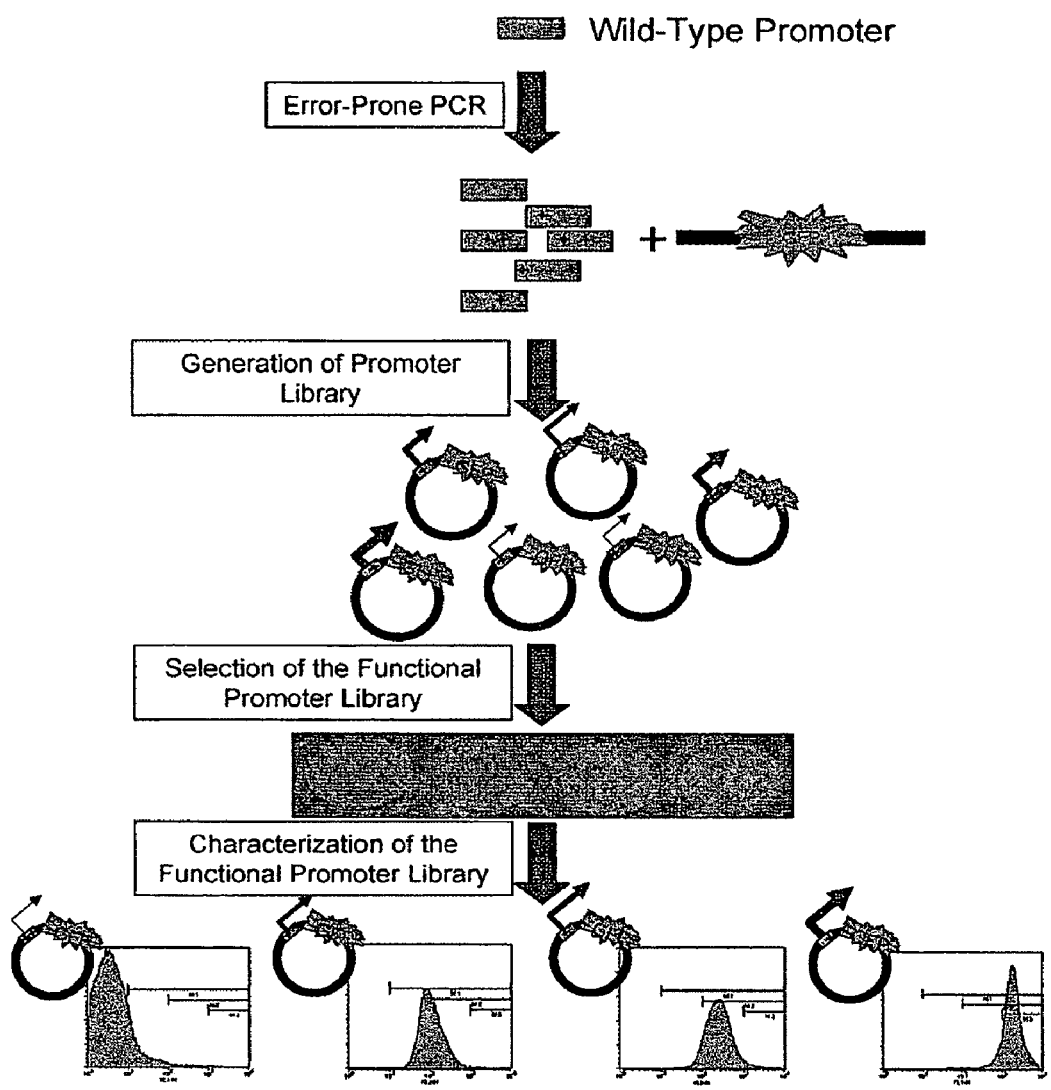
FIG. 1 depicts the generation of the functional promoter library. A variant of the constitutive bacteriophage $P_L$-λ promoter was mutated through error-prone PCR, used in a plasmid construct to drive the expression of gfp, then screened based on fluorescence of colonies. The chosen constructs have a wide range of fluorescence both on a culture-wide level and on a single-cell level as illustrated by representative flow cytometry histograms. All of the selected promoters have a uniform expression level on a single cell level as measured by GFP signal.

This invention provides, in one embodiment, constructs and/or expression cassettes comprising promoters of varying strength, operatively linked to at least one gene of interest and cells comprising the same. In one embodiment, the constructs are part of an expression library.

As is demonstrated herein, a derivative of the constitutive bacteriophage $P_L$-λ promoter was mutated through error-prone PCR and cloned into a plasmid upstream of a reporter. It was also demonstrated herein that chromosomal promoter delivery into the region upstream of a targeted gene, replacing a native promoter and its inherent regulation modality provided a quantitative means of assessing promoter strength for the library members.

In one embodiment, this invention provides a library of expression vectors, each vector comprising at least one gene of interest and a promoter operatively linked thereto, wherein each promoter comprises a nucleic acid, whose sequence is randomly mutated with respect to that of another in the library.

In one embodiment, the term "promoter" refers to a DNA sequence, which, in one embodiment, is directly upstream to the coding sequence, important for basal and/or regulated transcription of a gene. In one embodiment, only a few nucleotides within a promoter are absolutely necessary for its function.

In one embodiment, the promoter is a mutant of the endogenous promoter, which is normally associated with expression of the gene of interest. In one embodiment, such promoters will be randomly mutated, and will comprise a library of this invention. In another embodiment, such mutants will be evaluated for their promoter strength, in terms of the resulting levels of expression of the gene of interest. In one embodiment, the expression will be validated by at least two means, and in another embodiment, expression will be assessed at a population and single cell level, as exemplified herein, or via any such means, as will be appreciated by one skilled in the art.

In one embodiment, the promoter is a constitutive promoter, or in another embodiment, the promoter is inducible. In another embodiment, the promoter is inducible following the provision of specific conditions which stimulate expression from the particular promoter. In one embodiment, such conditions may include specific temperatures, nutrients, absence of nutrients, presence of metals, or other stimuli as will be known to one skilled in the art.

In one embodiment, this invention provides an isolated nucleic acid comprising a mutated $PL_{teto-1}$ promoter, wherein said mutated $PL_{teto-1}$ promoter has a sequence comprising:

a replacement of a/an:
a) T with a C at nucleotide position 12, 38, 39, 46, 52, 58, 60, 72, 73, 76, 79, 89, 99, 102, 108, 109, 114, 118, 120, 121, 127, or 133;
b) A with G at nucleotide position 12, 15, 16, 18, 19, 20, 26, 32, 35, 37, 39, 40, 41, 48, 49, 50, 51, 53, 59, 65, 81, 87, 94, 97, 101, 105, 107, 119, 122, 126, 128, 130 or 138;
c) C with A at nucleotide position 21;
d) A with C at nucleotide position 23, 62, 87, 101, 105, 113, 126, or 128;
e) T with A at nucleotide position 24;
f) C with T at nucleotide position 31 or 135;
g) A with T at nucleotide position 49, 51, 62, or 87;
h) G with A at nucleotide position 64, 67, 86, 98, 100, 125, 129 or 131;
i) T with G at nucleotide 109;
a deletion of nucleotide:
b) T at position 24 or 25;
b) T at position 28;
an insertion of nucleotide:
c) C between nucleotide positions 88 and 89;
d) T between nucleotide positions 96 and 97;
or any combination thereof, of the sequence as set forth in SEQ ID NO: 34.

In one embodiment, this invention provides a nucleic acid with a sequence as set forth in SEQ ID NO: 22-229.

In one embodiment, the libraries described in the present invention are constructed from nucleic acid fragments comprising genomic DNA, cDNA, or amplified nucleic acid. In one embodiment, the promoters, and/or, in another embodiment, the gene of interest, or, in another embodiment, genes of interest, under the control of the promoter, are derived from one or two, or more genomes, which, in another embodiment, may be well-characterized genomes.

The nucleic acids used in this invention can be produced by any synthetic or recombinant process such as is well known in the art. Nucleic acids can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences. These nucleic acids may comprise the vector, the expression cassette, the promoter sequence, the gene of interest, or any combination thereof.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together (see, generally, Sambrook et al. (1989) and Glover et al. (1995)). DNA expressing functional homologues of the protein can be prepared from wild-type DNA by site-directed mutagenesis (see, for example, Zoller et al. (1982); Zoller (1983); and Zoller (1984); McPherson (1991)). The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989).

In one embodiment, the genome selected is one that is well-characterized. In one embodiment, the genome is a compact genome of a eukaryote (ie. protist, dinoflagellate, alga, plant, fungus, mould, invertebrate, vertebrate, etc) such as, for example, a eukaryote from: *Arabidopsis thaliana, Anopheles gambiae, Caenorhabditis elegans, Danio rerio, Drosophila melanogaster, Takifugu rubripes, Cryptosporidium parvum, Trypanosoma cruzii, Saccharomyces cerevesiae,* and *Schizosaccharomyces pombe*. In another embodiment, the genome is murine, rat, simian or human.

In another embodiment, the genome is a compact genome of a prokaryote (ie. bacteria, eubacteria, cyanobacteria, etc) such as, for example a prokaryote from: *Archaeoglobus julgidis, Aqui/ex aeolicus, Aeropyrum pernix, Bacillus subtilis, Bordetella pertussis* TOX6, *Borrelia burgdorferi, Chlaniydia trachomatis, Escherichia coli* K12, *Haemophilus influenzae* (rd), *Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis* PCC 6803, *Thermoplasma volcanium Andrhermotoga maritima*.

In another embodiment, the promoter library may be derived from sequences from *Actinobacillus pleuropneumoniae, Aeropyrum pernix, Agrobacterium tumeficians, Anopheles gambiae, Aquifex aeolicus, Arabidopsis thaliana, Archeglobus fulgidis, Bacillus anthracis, bacillus cereus, Baccilus halodurans, Bacillus subtilis, Bacteroides thetaiotaomicron, Bdellovibrio bacteriovorus, Bifidobacterium longum, Bordetella bronchiseptica, Bordetella pertussis, Borrelia burgdorferi, Bradyrhizobium japonicum, Brucella melitensis, Brucella suis, Bruchnera aphidicola, Brugia malayi, Caenorhabditis elegans, Canipylobacter jejuni, Candidatus blochmanniafloridanus, Caulobacter crescentus, Chlarnydia muridarum, Chlamydia trachomatis, Chlamydophilia caviae, Chlamydia pneumoniae, Chlorobium tepidum, Chromobacterium violaceum, Clostridium acetobutylicum, Clostridium perfringens, Clostridium tetani, Corynebacterium diphtheriae, Corynebacterium efficiens, Corynebacterium glutamicum, Coxiella burnetii, Danio rerio, Dechloromonas aromatica, Deinococcus radiodurans, Drosophila melanogaster, Eimeria tenella, Eimeria acervulina, Entamoeba histolytica, Enterococcus faecalis, Escherichia coli, Fusobacterium nucleatum, Geobacter su6rurreducens, Gloeobacter violaceus, Haemophilis ducreyi, Haemophilus influenzae, Halobacterium, Helicobacter hepaticus, Helicobacter pylori, Lactobacillus johnsonii, Lactobacillus plantarum, Lactococcus lactis, Leptospira interrogans serovar lai, Listeria innocua, Listeria monocytogenes, Mesorhizobium loti, Methanobacter thermoautotrophicus, Methanocaldocossus jannaschii, Methanococcoides burtonii, Methanopyrus kandleri, Methanosarcina acetivorans, Methanosareina mazei Goel, Mycobacterium avium, Mycobacterium bovis, Mycobacterium leprae, Mycobacterium tuberculosis, Mycoplasma gallisepticum* strain R, *Mycoplasma genitalium, Mycoplasma penetrans, Mycoplasma pneumoniae, Mycoplasma pulmonis, Nanoarchaeum equitans, Neisseria meningitidis, Nitrosomonas europaea, Nostoc, Oceanobacillus iheyensis, Onion yellows phytoplasma, Oryzias latipes, Oryza sativa, Pasteurella multocida, Photorhabdus luminescens, Pirellula, Plasmodium falciparum, Plasmodium vivax, Plasmodium yoelii, Porphyromonas gingivalis, Prochlorococcus marinus, Pseudomonas aeruginosa, Pseudomonas putida, Pseudomonas syringae, Pyrobaculum aerophilum, Pyrococcus abyssi, Pyrococcus furiosus, Pyrococcus horikoshii, Ralstonia solanacearum, Rhodopseudomonas palustris, Rickettsia conorii, Rickettsia prowazekii, Rickettsia rickettsii, Saccharomyces cerevisiae, Salmonella enterica, Salmonella typhimurium, Sarcocystis cruzi, Schistosoma mansoni, Schizosaccharomyces pombe, Shewanella oneidensis, Shigella flexneri, Sinorhizobium meliloti, Staphylococcus aureus, Staphylococcus epidermidis, Streptococcus agalactiae, Streptococcus agalactiae, Streptococcus mutans, Streptococcus pneumoniae, Strepto-* coccus pyogenes, Streptomyces avermitilis, Streptomyces coelicolor, Suffiblobus tokodaii, Synechocystis sp., Takifugu rubripes, Tetraodon fluviatilis, Thleileria parva, Thermoanaerobacter tengcongensis, Thernzoplasma acidophilum, Thermoplasma voleanium, Thermosynechococcus elongatus, Aermotoga maritima, Toxoplasma gondii, Treponema denticola, Treponema pallidum, Tropheryma whipplei, Tryponosoma brucei, Trypanosoma cruzi, Ureaplasma urealyticum, Vibrio cholerae, Vibro parahaemolyticus, Pbro vulnificus, Wigglesworthia brevipalpis, Wolbachia endosymbiont of Drosophilia melanogaster, W01inella succinogenes, Xanthomonas axonopodis pv. Citri, Xanthomonas campestris pv. Campestris, Xylella fastidiosa, or Yersinia pestis.

In another embodiment, nucleic acid fragments are derived from viral genomes, such as, for example: T7 phage, HIV, equine arteritis virus, lactate dehydrogenase-elevating virus, lelystad virus, porcine reproductive and respiratory syndrome virus, simian hemorrhagic fever virus, avian nephritis virus, turkey astrovirus, human asterovirus type 1, 2 or 8, mink astrovirus 1, ovine astrovirus 1, avian infectious bronchitis virus, bovine coronavirus, human coronavirus, murine hepatitis virus, porcine epidemic diarrhea virus, SARS coronavirus, transmissible gastroenterifis virus, acute bee paralysis virus, aphid lethal paralysis virus, black queen cell virus, cricket paralysis virus, *Drosophila* C virus, himetobi P virus, kashmir been virus, plautia, stali intestine virus, rhopalosiphutn padi virus, taura syndrome virus, triatoma virus, allchunna virus, apoi virus, cell fusing agent virus, deer tick virus, dengue virus type 1, 2, 3 or 4, Japanese encephalitis virus, Kamiti River virus, kunjin virus, langat virus, louping ill virus, modoc virus, Montana myotis leukoencephalitis virus, Murray Valley encephalitis virus, omsk hemorrhagic fever virus, powassan virus, Rio Bravo virus, Tamana bat virus, tick-borne encephalitis virus, West Nile virus, yellow fever virus, yokose virus, Hepatitis C virus, border disease virus, bovine viral diarrhea virus I or 2, classical swine fever virus, pestivirus giraffe, pestivirus reindeer, GB virus C, hepatitis G virus, hepatitis GB virus, bacteriophage Ml 1, bacteriophage Qbeta, bacteriophage SP, enterobacteria phage MXI, enterobacteria NL95, bacteriophage AP205, enterobacteria phage fr, enterobacteria phage GA, enterobacteria phage KU1, enterobacteria phage M12, enterobacteria phage MS2, pseudomonas phage PP7, pea enation mosaic virus-1, barley yellow dwarf virus, barley yellow dwarf virusGAV, barley yellow dwarf virus-MAW, barley yellow dwarf virus-PAS, barley yellow dwarf virus-PAV, bean leafroll virus, soybean dwarf virus, beet chlorosis virus, beet mild yellowing virus, beet western yellows virus, cereal yellow dwarf virus-RPS, cereal yellow dwarf virus-RPV, cucurbit aphid-borne yellows virus, potato leafroll. virus, turnip yellows virus, sugarcane yellow leaf virus, equine rhinitis A virus, foot- and mouth disease virus, encephalomyocarditis virus, theilovirus, bovine enterovirus, human enterovirus A, B, C, D or E, poliovirus, porcine enterovirus A or B, -unclassified enterovirus, equine rhinitis B virus, hepatitis A virus, aichi virus, human parechovirus 1, 2 or 3, Ijungan virus, equine rhinovirus 3, human rhinovirus A and B, porcine tescbovirus 1, 2-7, 8, 9, 10 or 11, avian encephalomyelitis virus, kakago virus, simian picornavirus 1, aura virus, bartnah forest virus, chikungunya virus, eastern equine encephalitis virus, igbo ora virus, mayaro virus, ockelbo virus, onyong-nyong virus, Ross river virus, sagiyama virus, salmon pancrease disease virus, semliki forest virus, sindbis virus, sindbus-like virus, sleeping disease virus, Venezuelan equine encephalitis virus, Western equine encephalomyelitis virus, rubella virus, grapevine fleck virus, maize rayado fino virus, oat blue dwarf virus, chayote mosaic tymovirus, eggplant mosaic virus, erysimum latent virus, kennedya yellow mosaic virus, ononis yellow mosaic virus, physalis mottle virus, turnip yellow mosaic virus or poinsettia mosaic virus.

In another embodiment, the genome is the human genome, or from *Mus* or *Rattus* genuses. In another embodiment, the genome is from a simian.

Information regarding sequenced viruses and/or bacteria and/or other sources, such as animals or humans is readily obtained from publicly available sources, such as, for example, the databases of National Center for Biotechnological Information, Entrez Genomes (NCBI), the Sangre Center, the Institute for Genomic Research (TIGR), the National Center for Genome Resources, or others.

In one embodiment, when nucleic acid fragments are from mixtures of organisms, the organisms are not normally found together in nature. In accordance with this embodiment of the invention, the process of combining nucleic acid fragments derived from diverse organisms not normally found together in nature enhances and controls diversity of the expression library produced using such nucleic acid fragments.

It is to be understood that the nucleic acid fragments used in the production of the expression cassettes or expression libraries of the present invention are generated using art-recognized methods such as, for example, a method selected from the group consisting mechanical shearing, digestion with a nuclease and digestion with a restriction endonuclease.

Combinations of such methods can also be used to generate the genome fragments, which comprise the promoters and/or gene/s of interest, of which the expression cassettes and/or libraries of this invention are comprised, and/or are used in the methods of this invention. In one embodiment, copies of nucleic acid fragments from one or two or more genomes are generated using polymerase chain reaction (PCR) using random oligonucleotide primers.

In another embodiment, the cassettes or genomes are randomly mutated by any means known in the art, such as, for example, chemical mutagenesis, or via the use of error-prone PCR, as known in the art, and exemplified herein. A derivative of the constitutive bacteriophage $P_L$-λ promoter was mutated through error-prone PCR, cloned into a reporter plasmid upstream of a low-stability GFP gene, and screened in *E. coli* based on the fluorescence signal in a glucose minimal medium. A functional promoter library of mutants was formed, wherein reproducible and homogeneous single-cell fluorescence distributions as measured by flow cytometry (FIG. 2).

In another embodiment, the methods of inducing random mutations using PCR are known in the art and, are described, for example, in Dieffenbach (ed) and Dveksler (ed) (In: PCR Primer: A Laboratory Manual, Cold Spring Harbour Laboratories, NY, 1995). In another embodiment, commercially available kits for use in mutagenic PCR are utilized, such as, for example, the Diversify PCR Random Mutagenesis Kit (Clontech) or the GeneMorph Random Mutagenesis Kit (Stratagene).

In one embodiment, PCR reactions are performed in the presence of at least about 200 mM manganese or a salt thereof. Such concentrations of manganese ion or a manganese salt induce from about 2 mutations per 1000 base pairs (bp) to about 10 mutations every 1 000 bp of amplified nucleic acid (Leung et al Technique 1, II-1 5, 1989).

In another embodiment, PCR reactions are performed in the presence of an elevated or increased or high concentration of dGTP, for example, between about 150 mM and about 200 mM. Such high concentrations of dGTP result in the misincorporation of nucleotides into PCR products at a rate of between about 1 nucleotide and about 3 nucleotides every 1 000 bp of amplified nucleic acid (Shahani et al BioTechniques 23, 304-306, 1997).

In another embodiment, the nucleic acid of the expression cassette and/or library is mutated by insertion into a host cell that is capable of mutating the nucleic acid. Such host cells are deficient in one or more enzymes, such as, for example, one or more recombination or DNA repair enzymes, thereby enhancing the rate of mutation to a rate that is rate approximately 5,000 to 10,000 times higher than for non-mutant cells.

In one embodiment, strains useful for the mutation of nucleic acids carry alleles that modify or inactivate components of the mismatch repair pathway. Examples of such alleles include mutH, mutM, mutD, mutI, mutA, mutC or mutS. Bacterial cells that carry alleles that modify or inactivate components of the mismatch repair pathway are known in the art, such as, for example the XL1Red, XL-mutS and XL-mutS-Kad bacterial cells (Stratagene).

In another embodiment, the nucleic acid fragments may be cloned into a nucleic acid vector that is preferentially replicated in a bacterial cell by the repair polymerase, Pol I. A Pol I variant strain which induces a high level of mutations in the introduced nucleic acid vector, may be used, in one embodiment, adapting the method described by Fabret et al (In: Nucl Acid Res, 28, 1-5 2000), which is incorporated herein by reference.

In another embodiment, the mutagenized library may be constructed using transposons. In one embodiment, the mariner transposon may be used. Mariner transposition occurs efficiently in vitro, does not require cellular cofactors and shows very little insertion site specificity, requiring only the dinucleotide TA in the target sequence (and even this minor site specificity can be easily altered using different in vitro reaction conditions). In another embodiment, the Tn7 transposon may be used.

Transposons occur naturally as DNA sequences coding for an enzyme, transposase, which recognizes and cuts the DNA at sites flanking the gene for the transposase. The recognition sites, or binding sites for the transposase, are referred to as inverted repeat sequence. As such, transposable elements, when activated, produce an enzyme, which promotes the excision of itself from one location in DNA and the insertion of the excised DNA at another site. In some embodiments, the transposon selected will exhibit site-specific insertion at so-called "hot spots."

In another embodiment, the transposon may be Tn551, Minos, Hermes or piggyback. In another embodiment, the transposon may be AT-2 (tyl based transposon, Perkin Elmer; Devine et al. (1997) Genome Res. 7:551-563), GPS-1 (New England Biolabs), GPS-2 (New England Biolabs), EZ::tn (Tn5 based transposon, Epicenter Technologies), SIF (Tn7 based transposon, Biery et al. (2000) Nucl Acid Res 28:1067-1077), or Mu (Finnzymes, Haapa et al. (1999) Nucl Acid Res 13:2777-2784). It is to be understood that any transposon may be used in the methods of this invention.

The transposons will be employed, in one embodiment, with their natural cognate transposases, or in another embodiment, with the use of modified and/or improved transposases.

In another embodiment, the transposon may comprise a nucleic acid sequence encoding a heterologous polypeptide. This sequence may be integrated, together with the transposon, into the genome of the cell on transposon integration. In one embodiment, the heterologous polypeptide may be excised, together with the transposon, when the latter excises on remobilisation. In one embodiment, the heterologous polypeptide is a detectable marker, such as, for example, the green fluorescent protein (GFP), or mutants, homologues thereof.

GFPs have been isolated from the Pacific Northwest jellyfish, *Aequorea Victoria*, from the sea pansy, *Renilla reniformis*, and from *Phialidium gregarium*. (Ward et al., 1982, Photochem. Photobiol., 35: 803-808; Levine et al., 1982, Comp. Biochem. Physiol., 72B: 77-85). See also Matz, et al., 1999, ibid for fluorescent proteins isolated recently from *Anthoza* species (accession nos. AF168419, AF168420, AF168421, AF168422, AF168423 and AF168424), each of which may be incorporated in the methods of this invention.

A variety of *Aequorea*-related GFPs having useful excitation and emission spectra have been engineered by modifying the amino acid sequence of a naturally occurring GFP from *Aequorea victoria* (Prasher et al., 1992, Gene, 111: 229-233; Heim et al., 1994, Proc. Natl. Acad. Sci. U.S.A., 91: 12501-12504; PCT/US95/14692).

In another embodiment, in vitro transposition may be conducted upon genomic DNA cloned into a vector, for example a cosmid, phage, plasmid, YAC (yeast artificial chromosome), or BAC (bacterial artificial chromosome) vector. Similar high-density mutagenesis can be performed in non-naturally competent organisms using genomic DNA cloned into an allelic replacement vector (see for example, U.S. Pat. No. 6,207,384).

In one embodiment, chromosomal DNA from the cell of interest is isolated and mutagenized with the Himar1 transposase and, in another embodiment, an artificial minitransposon encoding a marker gene, such as, for example, the gene for either kanamycin or chloramphenicol resistance.

Insertion of the transposon produces a short single-stranded gap on either end of the insertion site. In one embodiment, bacterial strains, which are known to take up single stranded DNA are utilized, and according to this aspect of the invention, these gaps may require repair (using a DNA polymerase and a DNA ligase) to produce the flanking DNA sequence required for recombination into the chromosome.

In another embodiment, the mutagenized cassettes and/or libraries are constructed via the use of radiation. When creating mutations through radiation, in one embodiment, ultraviolet (UV) or, in another embodiment, ionizing radiation may be used. Suitable short wave UV wavelengths for genetic mutations may fall within the range of 200 nm to 300 nm, in one embodiment, where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range may be used, in another embodiment, and may be used in conjunction with various activators such as psoralen dyes that interact with the DNA, in another embodiment.

In another embodiment, mutagenesis with chemical agents may also be used. Such chemical mutagens may comprise, in other embodiments, chemicals that affect nonreplicating DNA such as $HNO_2$ and $NH_2OH$, as well as agents that affect replicating DNA such as acridine dyes, which have been shown to cause frameshift mutations. Methods for creating mutants using radiation or chemical agents are well known in the art, and any method may be utilized for the methods of this invention (see, for example, Thomas D. Brock in Biotechnology: A Textbook of Industrial Microbiology, Second Edition (1989) Sinauer Associates, Inc., Sunderland, Ma., or Deshpande, Mukund V., Appl. Biochem. Biotechnol. 36, 227 (1992).

Mutagenized DNA is transformed into bacteria, in one embodiment, or other cells of interest, in another embodiment, by methods well known and described in the art (see for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Cells, which acquire transposon insertions by homologous recombination, are selected, for example via plating on an appropriate antibiotic-containing medium.

In one embodiment, southern blot analysis of digested DNA from individual transposon mutants to verify transposon insertion, or in another embodiment, from individual mutagenized cells. In another embodiment, sequence analysis, PCR and/or hybridization may be utilized to determine mutagenesis by, for example transposon insertion, or error-prone PCR, etc.

Screening of the mutagenized library obtained as exemplified herein on minimal media plates identified cells with varying expression of the reporter gene, which were a function of the mutations introduced into the promoter, which comprises embodiments of this invention. It is to be understood, that other promoters, and thereby mutations involved in regulated expression in such promoterss may be identified via the methods of this invention, as described herein. The method of identification, as well as strains obtained thereby, are to be considered as part of this invention.

It is to be understood that any method whereby random mutations are generated in promoter sequences may be used to generate the cassettes, libraries and/or vectors of this invention, and are to be considered an embodiment thereof. It is also to be understood that such methods may be combined, and comprise additional embodiments of the invention.

In one embodiment, the cassettes and/or vectors comprise nucleic acid fragments or cDNA or amplified DNA derived therefrom in operable connection with a gene, whose expression is desired. The construct used for the regulated expression of the gene under the control of the diverse promoter library may also comprise cassettes, which facilitate screening for expression on a qualitative and quantitative level. Thus, in one embodiment, an expression format suitable for screening the library is considered.

In one embodiment, the term "vector" in the present invention, may refer to a nucleic acid construct which further includes an origin of replication, and may be a shuttle vector, which can propagate both in prokaryotic, and in eukaryotic cells, or the vector may be constructed to facilitate its integration within the genome of an organism of choice. The vector, in other embodiements may be, for example, a plasmid, a bacmid, a phagemid, a cosmid, a phage, a virus or an artificial chromosome.

In one embodiment, the term "expression cassette" or "cassette" may refer to a nucleic acid which comprises a promoter sequence and a gene operatively linked thereto, wherein the promoter may be mutated, as described herein, for provision of an optimized expression level of said gene of interest for a particular application. In one embodiment, the cassette may be in any location, for example, it may be ligated within an expression vector, as described, or the cassette may be so engineered that it may integrate within a chromosome of a cell of interest.

In another embodiment, the cassette and/or vector contemplated by this invention further comprises an insertion of a heterologous nucleic acid sequence encoding a marker polypeptide. The marker polypeptide may comprise, for example, green fluorescent protein (GFP), DS-Red (red fluorescent protein), secreted alkaline phosphatase (SEAP), beta-galactosidase, luciferase, or any number of other reporter proteins known to one skilled in the art.

In one embodiment, the term "gene" refers to a nucleic acid fragment that is capable of being expressed as a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

Regulated expression of the genes of interest may be accomplished using the cassettes, vectors and/or libraries of this invention, and via any means as will be known to one skilled in the art. In one embodiment, such expression may be effected in genetically engineered bacteria, eukaryotic cells such as yeast, and/or mammalian cells, and such cells are to be considered as part of this invention. In one embodiment, a construct is introduced in the prokaryotes or eukaryotes, such that it is possible to select for homologous recombination events in the cell. One ordinarily skilled in the art can readily design such a construct including both positive and negative selection genes for efficiently selecting transfected cells that underwent a homologous recombination event with the construct.

There are a number of techniques known in the art for introducing cassettes and/or vectors into cells, for affecting the methods of the present invention, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation or liposome-mediated transfection, (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Bombardment with nucleic acid coated particles is also envisaged. It is to be understood that any of these methods may be utilized for introduction of the desired sequences into cells, and cells thereby produced are to be considered as part of this invention, as is their use for effecting the methods of this invention.

In one embodiment, the vector or gene construct is suitable for in vitro display of an expressed peptide. Preferred in vitro display formats include, ribosome display, mRNA display or covalent display.

In another embodiment, the cassette, vector or gene construct is suitable for expressing a peptide in a cellular host. Preferred cellular hosts in this context are capable of supporting the expression of exogenous or episomal DNA such as, for example, a cellular host, which may be a bacterial cell, yeast cell, insect cell, mammalian cell, plant cell, or others.

In another embodiment, the vector or gene construct is suitable for expressing a peptide in a multicellular organism, and may include multicellular organisms having a compact genome and/or short life cycle to facilitate rapid high throughput screening, such as, for example, a plant (eg., *Arabidopsis thaliana* or *Nicotinia tabaccum*) or an animal, such as *Caenorhabditis elegans, Danio rerio, Drosophila melanogaster, Takifugu rubripes*, or *Mus* or *Rattus* genuses.

In another embodiment, the vector or gene construct is suitable for expression in a prokaryote. In another embodiment, the vector or gene construct is suitable for expression in any eukaryotic cell.

Constructs Encoding Therapeutic Proteins

In one embodiment, the constructs of this invention comprise a gene of interest, which codes for a therapeutic protein.

In one embodiment, the term "construct" refers to an expression cassette, a vector or a library of vectors, as described herein.

In one embodiment, the term "therapeutic", refers to a molecule, which when provided to a subject in need, provides a beneficial effect. In some cases, the molecule is therapeutic in that it functions to replace an absence or diminished presence of such a molecule in a subject. In one embodiment, the therapeutic protein is that of a protein which is absent in a subject, such as in cases of subjects with an endogenous null or misense mutation of a required protein. In other embodiments, the endogenous protein is mutated, and produces a non-functional protein, compensated for by the provision of the functional protein. In other embodiments, expression of a heterologous protein is additive to low endogenous levels, resulting in cumulative enhanced expression of a given protein. In other embodiments, the molecule stimulates a signalling cascade that provides for expression, or secretion, or others of a critical element for cellular or host functioning.

In one embodiment the therapeutic protein may comprise an enzyme, an enzyme cofactor, a cytotoxic protein, an antibody, a channel protein, a transporter protein, a growth factor, a hormone or a cytokine.

In one embodiment, the term "antibody or antibody fragment" refers to intact antibody molecules as well as functional fragments thereof, such as Fab, F(ab')2, and Fv that are capable of binding to an epitope. In one embodiment, an Fab fragment refers to the fragment which contains a monovalent antigen-binding fragment of an antibody molecule, which can be produced by digestion of whole antibody with the enzyme papain to yield an intact light chain and a portion of one heavy chain. In one embodiment, Fab' fragment refers to a part of an antibody molecule that can be obtained by treating whole antibody with pepsin, followed by reduction, to yield an intact light chain and a portion of the heavy chain. Two Fab' fragments may be obtained per antibody molecule. In one embodiment, (Fab')$_2$ refers to a fragment of an antibody that can be obtained by treating whole antibody with the enzyme pepsin without subsequent reduction. In another embodiment, F(ab')$_2$ is a dimer of two Fab' fragments held together by two disulfide bonds. In one embodiment, Fv, may refer to a genetically engineered fragment containing the variable region of the light chain and the variable region of the heavy chain expressed as two chains. In one embodiment, the antibody fragment may be a single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

In one embodiment, the antibody will recognize an epitope, which in another embodiment, refers to antigenic determinant on an antigen to which the paratope of an antibody binds. Epitopic determinants may, in other embodiments, consist of chemically active surface groupings of molecules such as amino acids or carbohydrate side chains and in other embodiments, may have specific three dimensional structural characteristics, and/or in other embodiments, have specific charge characteristics.

In one embodiment, the epitope recognized is from a pathogen, or in another embodiment, a pathogenic cell, or in another embodiment, a protein aberrantly expressed, which, in another embodiment, may refer to the location, quantity, or combination thereof of expression.

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

In other embodiments, antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

In one embodiment, the antibody is tumoricidal, and is thereby therapeutic in certain cancers. Antibodies that possess tumoricidal activity are also known in the art, the use of any of which may represent an embodiment of this invention, including IMC-C225, EMD 72000, OvaRex Mab B43.13, anti-ganglioside G(D2) antibody ch14.18, CO17-1A, trastuzumab, rhuMAb VEGF, sc-321, AF349, BAF349, AF743, BAF743, MAB743, AB1875, Anti-Flt-4AB3127, FLT41-A, rituximab, 2C3, CAMPATH 1H, 2G7, Alpha IR-3, ABX-EGF, MDX-447, anti-p75 IL-2R, anti-p64 IL-2R, and 2A11.

In another embodiment, the therapeutic protein may comprise an enzyme, such as one involved in glycogen storage or breakdown. In one embodiment, the enzyme is involved in a metabolic pathway. In another embodiment, the invention provides for optimized production of a compound, which is a function of the regulated expression of a gene of interest. In one embodiment, the compound is a protein, or in another embodiment, a lipid, or in another embodiment, a carbohydrate, or in another embodiment, a mineral, or in another embodiment, a vitamin, or in another embodiment, any compound, whose production may be affected by a gene product of interest, whose expression may be regulated.

In another embodiment, the vector comprises sequences which allow for stable integration of the promoter and the gene of interest in the genome of a cell into which the vector is introduced.

Chromosomal promoter delivery into the region upstream of the targeted gene, replacing the native promoter and its inherent regulation modality, was exemplified herein. The accuracy of the assessment of genetic control was compared to a null expression level (i.e. gene knockout), and the quantitative nature of the regulation was demonstrated, via the derivation of an average promoter strength metric exemplified herein for the library members. Use of the integrated system, in one embodiment, bypassed instability associated with the over-expression of endogenous genes seen at times, using plasmid-based systems, however, in another embodiment of this invention, plasmid based systems using the constructs of the present invention are also envisioned.

Growth yield and lycopene production were evaluated, using some constructs of this invention. ppc gene regulation, which encodes for phosphoenol pyruvate carboxylase, a key anaplerotic enzyme, demonstrated exponential-phase biomass yields as a function of the average promoter strength metric. The results illustrated an optimum in the expression level of ppc that is above that found from endogenous expression.

Kinetic control of metabolic pathways is often distributed and dependent on the expression level of several genes within the pathway. Promoter delivery experiments allow for the quantification of this control. Volumetric productivity of lycopene accumulation in glucose medium was investigated as a function of the expression levels of the dxs gene in a wild-type and an engineered *E. coli* strain. Elevating dxs expression increased lycopene accumulation only until a certain point. Beyond this optimum, increased dxs expression was detrimental for lycopene production.

However, a linear relationship could be obtained when similar promoter-dxs constructs were placed in an engineered strain overexpressing downstream genes in the isoprenoid pathway (ispFD and idi). FIG. 3c illustrates a nearly linear response of lycopene production to varying levels of controlled dxs expression, suggesting that in the new genetic background, dxs was rate-limiting.

Since optimized protein expression may be a function of multiple gene products, in one embodiment, this invention provides libraries and methods of use thereof, wherein more than one gene of interest is under the control of the promoter, as described. In another embodiment, manipulation of other genes of interest may be effected, for use of the constructs of this invention, such as for example, introduction of the vectors described herein in cells genetically disrupted for specific genes involved in a given pathway targeted by the gene of interest. In another embodiment, the vectors are introduced into cells which are genetically engineered to overexpress a particular gene in a given pathway targeted by the gene of interest.

For example, in one embodiment of this invention, the metabolic pathway studied is that involved in carotenoid production. In one embodiment, such production utilizing the libraries of this invention, or according to the methods of this invention, may involved the transfer of carotenoid genes into heterologous organisms, resulting in optimal expression, as described herein, representing one embodiment of a means of obtaining optimal production of a compound of interest.

In one embodiment, the compound of interest is produced, as a result of optimal production of a gene product of interest. For example, a carotenoid may be optimized, via the libraries and methods of this invention, via optimizing a gene product, e.g. an enzyme involved in the processing of the desired product, for example, a carotenoid.

In one embodiment, genes from one organism may be expressed in another for both production, as well as evaluation of maximal production, of a compound of interest, as will be appreciated by one skilled in the art. For example, genes from *Erwina uredovora* and *Haematococcus pluvialis* will function together in *E. coli* (Kajiwara et al. Plant Mol. Biol. 29:343-352 (1995)). *E. herbicola* genes will function in *R. sphaeroides* (Hunter et al. J. Bact. 176:3692-3697 (1994)).

In another embodiment of this invention, the genetically engineered bacterium may belong to the *Acetobacter, Escherichia, Salmonella, Shigella, Erwina, Haematococcus, Rhodobacter, Myxococcus, Corynebacteria, Pseudomonas, Pyrococcus, Ruminococcus, Mycobacteria, Bacillus* genu. In another embodiment, the genetically engineered bacterium may be a methylotroph, or in another embodiment, a methanotroph such as *Methylomonas, Methylobacter, Mehtylococcus, Methylosinus, Methylocyctis, Methylomicrobium, Methanomonas, Methylophilus, Methylobacillus,* and *Methylobacterium*.

The term "methylotroph" refers, in one embodiment, to an organism capable of oxidizing organic compounds that do not contain carbon-carbon bonds. Where the methylotroph is able to oxidize methane ($CH_4$), the methylotroph is also a methanotroph. In one embodiment, the methylotroph uses methanol and/or methane as its primary carbon source.

In one embodiment, the methylotrophs and/or methanotrophs are C1 metabolizing bacteria. In one embodiment, the term "C1 metabolizing bacteria" refers to bacteria that have the ability to use a single carbon substrate as their sole source of energy and biomass.

In one embodiment, the term "C1 carbon substrate" refers to any carbon-containing molecule that lacks a carbon-carbon bond. Non-limiting examples are methane, methanol, formaldehyde, formic acid, formate, methylated amines (e.g., mono-, di-, and tri-methyl amine), methylated thiols, and carbon dioxide. In another embodiment, the C1 carbon substrates is selected from the group consisting of methanol and/or methane.

The term "methanotroph" or "methanotrophic bacteria" refers, in another embodiment, to a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas, Methylobacter, Methylococcus*, and *Methylosinus*. In one embodiment, the methanotrophic bacteria uses methane and/or methanol as its primary carbon source.

In one embodiment, the term "high growth methanotrophic bacterial strain" refers to a bacterium capable of growth with methane and/or methanol as the sole carbon and energy source and which possesses a functional Embden-Meyerhof carbon flux pathway, resulting in a high rate of growth and yield of cell mass per gram of C1 substrate metabolized (U.S. Pat. No. 6,689,601; hereby incorporated by reference). The specific "high growth methanotrophic bacterial strain" described herein is referred to as "*Methylomonas* 16a", "16a" or "*Methylomonas* sp. 16a", which terms are used interchangeably and which refer to the *Methylomonas* strain used in the present invention.

Techniques for the transformation of C1 metabolizing bacteria may parallel the general methodology that is utilized for other bacteria, which is well known to those of skill in the art.

Electroporation has been used successfully for the transformation of: *Methylobacterium extorquens* AM1 (Toyama, H., et al., FEMS Microbiol. Lett., 166:1 7 (1998)), *Methylophilus methylotrophus* AS1 (Kim, C. S., and T. K. Wood, Appl. Microbiol. Biotechnol., 48: 105 108 (1997)), and *Methylobacillus* sp. strain 12S (Yoshida, T., et al., Biotechnol. Lett., 23: 787 791 (2001)).

Bacterial conjugation, relying on the direct contact of donor and recipient cells, may also be used for the transfer of genes into C1 metabolizing bacteria. Bacterial conjugation processes may involve mixing together "donor" and "recipient" cells in close contact with one another. Conjugation occurs by formation of cytoplasmic connections between donor and recipient bacteria, with direct transfer of newly synthesized donor DNA into the recipient cells. The recipient in a conjugation accepts DNA through horizontal transfer from a donor bacterium. The donor in conjugative transfer may have a conjugative plasmid, conjugative transposon, or mobilizable plasmid.

In some cases, only a donor and recipient are required for conjugation. This occurs when the plasmid to be transferred is a self-transmissible plasmid that is both conjugative and mobilizable (i.e., carrying both tra genes and genes encoding the Mob proteins). In general, the process involves the following steps: 1.) Double-strand plasmid DNA is nicked at a specific site in oriT; 2.) A single-strand DNA is released to the recipient through a pore or pilus structure; 3.) A DNA relaxase enzyme cleaves the double-strand DNA at oriT and binds to a released 5' end (forming a relaxosome as the intermediate structure); and 4.) Subsequently, a complex of auxiliary proteins assemble at oriT to facilitate the process of DNA transfer.

A "triparental" conjugation may also be required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving C1 metabolizing bacteria include the work of: Stolyar et al. (Mikrobiologiya, 64(5): 686 691 (1995)); Motoyama, H. et al. (Appl. Micro. Biotech., 42(1): 67 72 (1994)); Lloyd, J. S. et al. (Archives of Microbiology, 171(6): 364 370 (1999)); Odom, J. M. et al. (U.S. Ser. No. 09/941,947 corresponding to WO 02/18617); U.S. Ser. No. 10/997,308; and U.S. Ser. No. 10/997,844; hereby incorporated by reference.

In one embodiment, the term "pathway" refers to metabolic pathways, wherein multiple proteins may play regulatory roles, such as, for example, different enzymes whose activity regulates formation of a particular product via, for example, cleavage or hydrogenation, or dehydrogenation, etc., or a precursor, or in another embodiment, of the product to an undesired form, etc.

In another embodiment, the term "pathway" may refer to proteins with somewhat related functions, such that when an overall response is required, the coordinated activity of the two produces a desired result. For example, the gene of interest may be a cytokine, wherein its regulated expression is provided in a host cell with a given HLA type, at a time of administration of a given vaccine, in order to produce maximal immunostimulation, and responsiveness.

In another embodiment, regulated expression of an antigenic protein or peptide is desired to produce a desired immune response. For example, and in one embodiment, low levels of protein/peptide expression may be desired for immunostimulation, while, in another embodiment, high levels of expression of the peptide/protein may be desired for immune tolerance to the protein, to the source from which the peptide is desired, or to a related peptide or protein. In some embodiments, expression of a particular cytokine in such a scenario may be desirable as well, which may bias the response, for example to one less associated with robust autoimmune responses, for example. In one embodiment, in autoimmune diseases, high levels of expression, concurrent with IL-4 expression may be desirable, in order to for example, tolerize the immune response to a given antigen. In another embodiment, high levels of expression of a particular autoimmune peptide or protein may be desired concurrent with expression of an antibody which blocks second signal delivery to a responding T cell, thereby tolerizing the responding T cell.

These are some examples of scenarios where multiple product expression is desired, wherein the ability to regulate the level of expression finds particular application. It is to be understood that any use of regulated expression, as determined using the libraries or via the methods of this invention are to be considered an embodiment of this invention, in any conceivable application or setting.

In another embodiment, the therapeutic protein comprises a transporter, such as an ion transporter, for example CFTR, or a glucose transporter, or other transporters whose deficiency, or inappropriate expression, results in a variety of diseases.

In another embodiment, the therapeutic protein comprises a tumor suppressor, or pro-apoptotic compound, which alters progression of cancer-related events.

In another embodiment, the therapeutic compound of the present invention may comprise an immunomodulating protein. In one embodiment, the immunomodulating protein comprises cytokines, chemokines, complement or components, such as interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, or complement components.

In another embodiment, a therapeutic compound of this invention may comprise a growth factor, or tissue-promoting factor. In one embodiment, the therapeutic compound is a bone morphogenetic protein, or OP-1, OP-2, BMP-5, BMP-6, BMP-2, BMP-3, BMP-4, BMP-9, DPP, Vg-1, 60A, or Vgr-1. In another embodiment, the therapeutic compound facilitates nerve regeneration or repair, and may include NGF, or other growth factors.

In another embodiment, the therapeutic molecule may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the $\alpha$ family, transforming growth factors of the $\beta$ family, gastrins, secretins, cholecystokinins, somatostatins, serotonins, substance P, transcription factors or combinations thereof.

In another embodiment, this invention provides a plurality of cells comprising the library of expression vectors of this invention.

In one embodiment, each cell comprises a vector of the library, which is stably integrated within the genome of the cell. In one embodiment, the cells do not endogenously express, or have been engineered such that they do not endogenously express the gene of interest.

In another embodiment, the gene is a reporter gene. In one embodiment, the reporter gene encodes a fluorescent protein. In one embodiment, the fluorescent protein is the jellyfish green fluorescent protein, or a mutant or variant thereof.

In another embodiment, the reporter gene confers drug resistance. In one embodiment, the reporter gene confers resistance to an antiobiotic, such as, for example, ampicilin, kanamycin, tetracycline, or others, as will be appreciated by one skilled in the art. In another embodiment, the antibiotic resistance genes may include those conferring resistance to neomycin (neo), blasticidin, spectinomycin, erythromycin, phleomycin, Tn917, gentamycin, and bleomycin. An example of the neomycin resistance gene is the neomycin resistance gene of transposon Tn5 that encodes for neomycin phosphotransferase 11, which confers resistance to various antibiotics, including G418 and kanamycin.

In another embodiment, the reporter is a chloramphenicol acetyl transferase gene (cat) and confers resistance to chloramphenicol.

In another embodiment, the selection systems used may include the herpes simplex virus thymidine kinase (Wigler et al., Cell, 11:223 (1977)), hypoxanthine-guanine phosphoribosyltransferase (Szybalska et al., Proc. Natl. Acad. Sci. USA, 48:202 (1992)), and adenine phosphoribosyltransferase (Lowy et al., Cell, 22:817 (1980)) genes employed in tk-, hgprt- or aprt-cells, respectively.

In another embodiment, antimetabolite resistance can be used by inclusion of the following genes: dhfr, which confers resistance to methotrexate (Wigler et al., Natl. Acad. Sci. USA, 77:357 (1980); O'hare et al., Proc. Natl. Acad. Sci. USA, 78:1527 (1981)); gpt, which confers resistance to mycophenolic acid (Mulligan et al., Proc. Natl. Acad. Sci. USA, 78:2072 (1981)); neo, which confers resistance to the aminoglycoside G418 (Clinical Pharmacy, 12:488-505; WU et al., Biotherapy, 3:87-95 (1991); Tolstoshev, Ann. Rev. Pharmacol. Toxicol., 32:573-596 (1993); Mulligan, Science, 260:926-932 (1993); and Morgan et al., Ann. Rev. Biochem., 62:191-217 (1993); Tibtech 11(5):155-215 (May 1993)); or hygro, which confers resistance to hygromycin (Santerre et al., Gene, 30:147 (1984)).

In another embodiment, the vectors may comprise two or more genes of interest.

Another aspect of the present invention provides a database comprising the nucleotide sequences of nucleic acid fragments of an expression library of the present invention in computer readable form. Such sequences may be used in virtual designs for some of the methods of this invention, in terms of optimizing production of a protein.

In one embodiment, the sequences and software for their analysis can be implemented on any conventional host computer system, such as those based on Intel® microprocessors and running Microsoft Windows operating systems. Other systems, such as those using the UNIX or LINUX operating system and based on IBM®, DEC® or Motorola® microprocessors are also contemplated. The sequences can be stored, and analysis can also be implemented to run on client-server systems and wide-area networks, such as the Internet.

Software to implement the system can be written in any well-known computer language, such as Java, C, C++, Visual Basic, FORTRAN or COBOL and compiled using any well-known compatible compiler.

The software of the invention normally runs from instructions stored in a memory on the host computer system. Such a memory can be a hard disk, Random Access Memory, Read Only Memory and Flash Memory. Other types of memories are also contemplated to function within the scope of the invention.

For each gene invovlved in ascertaining a parameter of interest, for example, for a metabolic pathway, all information, including potential yields, as a function of promoter sequence, or regulated expression of other genes involved in the pathway, etc. are gathered and compiled in a matrix. In one embodiment, algorithms may be developed, which indicate other genes whose regulated expression may result in optimization of a product yield, for example, and in one embodiment, or in another embodiment, optimization of immune reactivity, as described herein.

In one embodiment, the mutations in each promoter result in varying promoter strength, which, in one embodiment, may vary between up to 1000-fold. In one embodiment, methods for optimal production of a compound of interest, as described herein, may make use of constructs, wherein the gene of interest is expressed at the highest level obtained, or in another embodiment, a construct with less than the maximal yield may be used, which may produce optimal expression, in another embodiment, when the expression of additional genes involved in the production are regulated as well. Such regulation may comprise overexpression, or underexpression, or in another embodiment, inhibiting expression.

In one embodiment, this invention provides a method of determining an optimized level of gene expression for a gene of interest, the method comprising
  contacting a plurality of cells with a library of expression vectors, each vector comprising at least one gene of interest and a promoter operatively linked thereto, wherein each promoter comprises a nucleic acid, whose sequence is randomly mutated with respect to that of another in said library, and wherein relative changes in expression level of said gene of interest are a function of the mutation in said promoter sequence;
  detecting said relative changes in expression level; and
  identifying a cell from said plurality of cells with a desired expression level,
  thereby being a method of determining an optimized level of gene expression for a gene of interest.

In one embodiment, the vectors may comprise any embodiment as described herein, or any combination thereof, including, in other embodiments, comprising sequences which allow for stable integration of the promoter and the gene of interest in the genomes of the cells, where optimized production is to be determined.

In another embodiment, each vector in the library provides a consistent level of expression of the gene of interest, which, in another embodiment, is verified via at least two different methods. In one embodiment, the method or methods verify expression at a single cell level, and in another embodiment, may comprise fluorescent activated cell sorting analysis, fluorescence microscopy, or a combination thereof. In another embodiment, the detection of relative changes in expression is accomplished with the use of quantitative polymerase chain reaction. In another embodiment, the detection of relative changes in expression in the case where the at least one gene of interest encodes an enzyme is accomplished via determining the enzyme activity.

In another embodiment, optimized production of a compound of interest is evaluated, wherein the production of the compound is a function of the regulated expression of a gene of interest, or, in another embodiment, two or more genes of interest. In one embodiment, according to this aspect of the invention, the method may be conducted similarly to that set forth for determination of optimized gene expression of a gene of interest.

In one embodiment, the methods of this invention, when evaluating optimized production of a compound, which comprise vectors with tow or more genes encoding proteins of interest, involve method genes encoding proteins which are interrelated. In one embodiment, the two or more genes encode proteins involved in a metabolic pathway, or as described hereinabove, the two or more genes are interrelated in terms of their concerted effects on a particular pathway, as described and/or defined herein. In one embodiment, such genes may be overexpressed.

In another embodiment, the cells according to the methods of this invention, do not endogenously express, or have been engineered such that they do not endogenously express the gene or genes of interest. In another embodiment, the vectors comprise sequences which allow for stable integration of the promoter and the gene of interest in the genomes of the cells.

In another embodiment, the method further comprises identifying the promoter within the cell. In another embodiment, this invention provides a method of optimized protein delivery to a subject, comprising administering to a subject a vector comprising the promoter identified herein.

In another embodiment, this invention provides a cell with a desired expression level of a gene of interest, identified by a method of this invention. In one embodiment, the cell does not endogenously express, or has been engineered such that it does not endogenously express said gene of interest.

In another embodiment, this invention provides a method of optimized protein delivery to a subject, comprising administering to said subject a cell which expresses an optimized level of the protein, identified via a method of this invention.

In one embodiment, the expression of the gene of interest is homogeneous, at a single cell level. In one embodiment, reference to "homogeneous" refers to minimal clonal variability. In one embodiment, "minimal" refers to less than 20%, or in another embodiment, less than 15%, or in another embodiment, less than 10%, or in another embodiment, less than 5%, or in another embodiment, less than 1%, or in another embodiment, between 1-5% variability in expression.

In one embodiment, determination of homogeneous expression is accomplished via the use of two separate methods, which quantify expression. Such cross-validation was exemplified herein, via the use of flow cytometry and fluorescent microscopy, for determining GFP expression.

The effect of two endogenous genes (ppc and dxs) on two divergent phenotypes, namely, growth yield and lycopene production, which in one embodiment, represents some of the methods utilizing the libraries or cells of this invention, in optimizing gene expression, protein expression, or optimized gene or protein delivery, were exemplified herein.

A library of engineered promoters of varying strength obtained through mutagenesis of a constitutive promoter was exemplified herein. A multi-faceted characterization of the library permitted quantitative assessment correlating the effect of gene expression levels to improved growth and product formation phenotypes in *E. coli*. The promoter library concept was generalizable to eukaryotic organisms (*S. cerevisiae*), as exemplified herein. Accordingly, in one embodiment, the libraries and methods of this invention constitute an integral platform for functional genomics and metabolic engineering.

Carotenoid Production:

In one embodiment, the libraries and/or methods of this invention may be useful in optimizing carotenoid production.

In one embodiment, the term "carotenoid" refers to a class of hydrocarbons (carotenes) and their oxygenated derivatives (xanthophylls) consisting of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. All carotenoids may be formally derived from the acyclic C40H56 structure (Formula I below), having a long central chain of conjugated double bonds, by (i) hydrogenation. (ii) dehydrogenation, (iii) cyclization, or (iv) oxidation or any combination of these processes.

Formula I

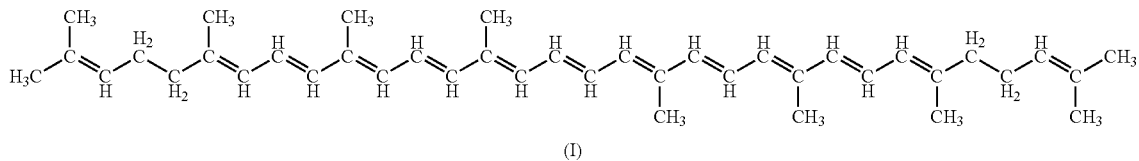

(I)

In another embodiment, carotenoids also include compounds that arise from certain rearrangements of the carbon skeleton (I), or by the (formal) removal of part of this structure.

In another embodiment, carotenoids are represented by the structure of the formula (II):

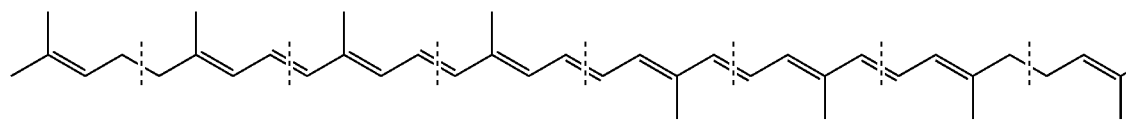

(IR)

where the broken lines indicate formal division into isoprenoid units.

Genes Involved in Carotenoid Production

Carotenoid synthesis is catalyzed by relatively small numbers of clustered genes in various microorganisms. For example, carotenoid synthesis is catalyzed by 11 different genes within 12 kb of DNA from *Myxococcus xanthus* and 8 genes within 9 kb of DNA from *Rhodobacter sphaeroides*. In some microorganisms, such as *Thermus thermophilus*, these genes are plasmid-borne.

The enzyme pathway involved in the biosynthesis of carotenoids can be conveniently viewed in two parts, the upper isoprenoid pathway providing for the conversion of pyruvate and glyceraldehyde-3-phosphate to isopentenyl pyrophosphate and the lower carotenoid biosynthetic pathway, which provides for the synthesis of phytoene and all subsequently produced carotenoids. The upper pathway is ubiquitous in many microorganisms.

IPP biosynthesis, a precursor produced in the upper isoprenoid pathway, occurs, in one embodiment, through the well-known acetate/mevalonate pathway. In another embodiment, an alternate mevalonate-independent pathway for IPP biosynthesis has been characterized in bacteria and in green algae and higher plants. In one embodiment, the first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. It's overexpression may enhance production, as exemplified herein.

The isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP, also referred to as ispD as a part of the isp gene cluster (SwissProtein Accession #Q46893).

The 2nd position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene is also referred to as ispE, also a part of the isp gene cluster (SwissProtein Accession #P24209). The product of ygbB gene converts 4-diphosphocytidyl-2C-methyl-D-erythritol 2-phosphate to 2C-methyl-D-erythritol 2,4-cyclodiphosphate in a CTP-dependent manner. This gene is also a part of the isp gene cluster, and is referred to as ispF (SwissProtein Accession #P36663), in another embodiment.

It is known that 2C-methyl-D-erythritol 2,4-cyclodiphosphate can be further converted into IPP to ultimately produce carotenoids in the carotenoid biosynthesis pathway. However, the reactions leading to the production of isopentenyl monophosphate from 2C-methyl-D-erythritol 2,4-cyclodiphosphate are not yet well-characterized. The enzymes encoded by the lytB and gcpE genes, in one embodiment, are thought to participate in the reactions leading to formation of isopentenyl pyrophosphate (IPP) and dimethylallyl pyrophosphate (DMAPP). In another embodiment, additional gene products are involved.

IPP may be isomerized, in another embodiment, to DMAPP via IPP isomerase, encoded by the idi gene, however participation of this enzyme is not necessary and may be bypassed vias the 2-C-methyl-D-erythritol 4-phosphate (MEP) pathway. In another embodiment, the MEP pathway branches before IPP synthesis and separately produces IPP and DMAPP via the lytB gene product.

The formation of phytoene is produced via the lower carotenoid biosynthetic pathway. The synthesis of phytoene occurs, in one embodiment, via isomerization of IPP to dimethylallyl pyrophosphate (DMAPP). This reaction, in another embodiment, is followed by a sequence of 3 prenyltransferase reactions. In one embodiment, two of these reactions are catalyzed by ispA, leading to the creation of geranyl pyrophosphate (GPP; a 10-carbon molecule) and farnesyl pyrophosphate (FPP; 15-carbon molecule). In one embodiment, the genes crtN1 and crtN2 convert farnesyl pyrophosphate to a 30-carbon pigment.

According to this aspect of the invention, and in one embodiment, the gene crtE, encoding GGPP synthetase is responsible for the 3rd prenyltransferase reaction, which may occur, leading to the synthesis of phytoene. This reaction adds IPP to FPP to produce a 20-carbon molecule, geranylgeranyl pyrophosphate (GGPP). A condensation reaction of two molecules of GGPP may then occur, according to this aspect of the invention, to form phytoene (PPPP), the first 40-carbon molecule of the lower carotenoid biosynthesis pathway. This enzymatic reaction is catalyzed by crtB, encoding phytoene synthase.

In one embodiment, lycopene, which imparts a "red"-colored spectra, is produced from phytoene through four sequential dehydrogenation reactions by the removal of eight atoms of hydrogen, catalyzed by the gene crtI (encoding phytoene desaturase). Intermediaries in this reaction are phtyofluene, zeta-carotene, and neurosporene.

In one embodiment, lycopene cyclase (crtY) converts lycopene to β-carotene, which in another embodiment, is converted to zeaxanthin via a hydroxylation reaction resulting from the activity of β-carotene hydroxylase (encoded by the crtZ gene). B-cryptoxanthin is an intermediate in this reaction, in one embodiment.

In another embodiment, β-carotene is converted to canthaxanthin by β-carotene ketolase encoded by the crtW gene, and echinenone in an intermediate in this reaction, in one embodiment. In another embodiment, canthaxanthin may be converted to astaxanthin by β-carotene hydroxylase encoded by the crtZ gene. In one embodiment, adonbirubrin is an intermediate in this reaction.

In another embodiment, zeaxanthin may be converted to zeaxanthin-β-diglucoside, via the activity of zeaxanthin glucosyl transferase (crtX). In one embodiment, zeaxanthin may be converted to astaxanthin by β-carotene ketolase encoded by crtW, crtO or bkt. In one embodiment, adonixanthin is an intermediate in this reaction.

In one embodiment, the carotenoids may include antheraxanthin, adonixanthin, astaxanthin, canthaxanthin, capsorubrin, β-cryptoxanthin echinenone, zeta-carotene, alpha-cryptoxanthin, diatoxanthin, 7,8-didehydroastaxanthin, fucoxanthin, fucoxanthinol, isorenieratene, lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-diglucoside, and zeaxanthin.

Optimization of Carotenoid Production

Since multiple pathways are required for carotenoid production, in one embodiment, genes impacting carotenoid biosynthesis in a given microorganism and/or cell may be individually regulated, via the use of the mutated promoters, as described herein, and optimization of production as a function of promoter strength may be determined, as described and exemplified herein. In another embodiment, several genes in combination may be regulated, to successfully produce higher yields of carotenoids. The phenotype may not be additive in nature, in one embodiment. In another embodiment, specific genes may be inactivated, or "knocked out" by methods well known in the art, while expression of other genes may be optimized, which in turn may optimize expression of, in one embodiment, carotenoid production. It is to be understood that such a scenario whereby multiple genes involved in a particular pathway, as described herein, may be similarly evaluated, such that optimal production of a compound of interest is achieved, by regulated expression of a particular gene involved in the pathway, or in another embodiment, a group of genes, and in another embodiment, gene inactivation and/or knockout of other genes involved in the pathway may also be affected, all of which are to be considered as part of this invention.

Carotenoids are terpenoids derived from an isoprene building block, isopentenyl pyrophosphate (IPP). Carotenoids are produced via the general isoprenoid biosynthetic pathway by bacteria, fungi and plants. These pigments protect organisms against photooxidative damage, as well as functioning as anti-tumor agents, free radical-scavenging anti-oxidants, and enhancers of the immune response. Additionally, they are used commercially in pigmentation of cultured fish and shellfish.

In one embodiment, the term "isoprenoid compound" refers to any compound which is derived via the pathway beginning with isopentenyl pyrophosphate (IPP) and formed by the head-to-tail condensation of isoprene units which may be, in one embodiment, of 5, or, in another embodiment, of 10, or, in another embodiment, of 15, or, in another embodiment, of 20, or, in another embodiment, of 30 or, in another embodiment, of 40 carbons in length. In another embodiment, isoprenoid compounds may comprise isoprenoid pigments, which in one embodiment, refers to a class of compounds, which typically have strong light absorbing properties.

The isoprenoid biosynthetic pathway can be divided, in one embodiment, into two portions: the upper isoprene pathway, which leads to the formation of IPP, and the lower carotenoid biosynthetic pathway, which converts IPP into long C30 and C40 carotenogenic compounds.

The terms "upper isoprenoid pathway" and "upper pathway" are used interchangeably and refer, in one embodiment, to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthase); the "dxr" gene (encoding 1-deoxyxylulose-5-phosphate reductoisomerase; also known as the ispC); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase; also known as ispF); the "lytB" gene (also known as ispH) involved in the formation of dimethylallyl diphosphate; the "gcpE" gene (also known as ispG) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

In one embodiment, the term "Dxs" refers to the 1-deoxyxylulose-5-phosphate synthase enzyme encoded by the dxs gene. In another embodiment, the term "Dxr" refers to the 1-deoxyxylulose-5-phosphate reductoisomerase enzyme encoded by the dxr gene. In another embodiment, the term "YgbP" or "IspD" refers to the 2C-methyl-D-erythritol cytidyltransferase enzyme encoded by the ygbP or ispD gene. In another embodiment, the terms ygbP or ispD, are used interchangeably. In another embodiment, the terms YgbP or IspD are used interchangeably in this application, to designate ygbP or ispD gene products.

As exemplified herein, optimized production of a carotenoid may be effected using the libraries and/or generated via the methods of this invention, wherein elevation of dxs expression, resulted in the highest level of isprenoid production, when ispFD and idi were also overexpressed.

Methods for the detection of the carotenoids produced in the cells or via the methods of this invention are well known in the art, and may comprise, in one embodiment, HPLC, Mass Spectroscopy, ELISA, RIA or Western blot analysis [see "Cell Biology: A Laboratory Handbook", Volumes I-III Cellis, J. E., ed. (1994); "Current Protocols in Immunology" Volumes I-III Coligan J. E., ed. (1994); Stites et al. (eds)].

In one embodiment, the carotenoids are dissolved in a supernatant or filtrate, and may be recovered from them. As a solvent for the extraction, any substance in which the present compound is soluble can be used. For example, and in other embodiments herein, organic solvents such as acetone, chloroform, dichloromethane, hexane, cyclohexane, methanol, ethanol, isopropanol, benzene, carbon disulfide, diethyl ether etc. may be used. The purification may be carried out by conventional procedures such as absorption, elution, dissolving and the like, alone or preferably in combination In another embodiment, mixtures of carotenoids are produced, such as for example, simultaneous production of astaxanthin, adonixanthin, β-carotene, echinenone, canthaxanthin and/or zeaxanthin and are present in a culture product. Accordingly, in an embodiment of the present invention, any one of the above-mentioned carotenoids can be singly obtained by the above-mentioned procedure. Alternatively, a mixture of the carotenoids also can be obtained. In this way, the process for carotenoid production of the present invention includes a process for production of an individual carotenoid and a process for production of a mixture of the carotenoids.

Astaxanthin and adonixanthin can be separated from each other by methods well known to one skilled in the art for mutual separation of carotenoids, such as adsorption/elusion column chromatography, differential extraction, counter current extraction or differential crystallization.

In another embodiment, this invention provides a method of optimized protein delivery to a subject, the method comprising administering to the subject a vector comprising a promoter identified via the methods of this invention. As described herein, and in one embodiment, this invention provides a means for determining optimized production of a compound, using the libraries of this invention. Once such optimized production is determined, the constructs which impart the optimized production may then be administered to a subject. In one embodiment, such optimized production may be accomplished in a cell or plurality of cells, which may, in another embodiment, be administered to a subject. In one embodiment, the construct may be delivered to a subject. In one embodiment, delivery of the cell or construct to a subject may be a means of cell or gene therapy, respectively, as will be understood to one skilled in the art.

In one embodiment, the cell with optimized expression, or contacted with a vector for optimized expression, etc., of this invention, does not endogenously express, or has been engineered such that it does not endogenously express the gene of interest. In one embodiment, such a cell may be engineered to express or overexpress a second gene of interest, or, in another embodiment, a variant or mutant of the first gene of interest, or in another embodiment, may express the gene of interest under the control of a promoter, identified in this invention, as providing a desired expression level of a gene or genes of interest, as described herein.

In another embodiment, such cells may be prokaryotic or eukaryotic, and may be expanded in culture. In one embodiment, such cells may be ex-vivo expanded, then reimplanted in a host, wherein the cells are modified in culture, prior to their implantation. In one embodiment, the cell may be a stem cell, or in another embodiment, a progenitor cell, or in another embodiment, a differentiated cell. In one embodiment, the cells which are to be implanted in a subject may be further engineered to comprise a protein which facilitates the homing of the cell to a desired location. Such proteins are recognized by one skilled in the art, and may comprise specific adhesion molecules, integrins, etc., which enable specific delivery to a site of interest. In another embodiment, specific delivery to a site may be accomplished via the means of delivery, such as, for example, direct injection to a site of interest, or, for example, delivery via route of administration to a desired site via particular formulation, such as, for example, aerosol formulation for lung delivery, or for example, formulation in a suppository for delivery to particular mucosal sites, or for example, topical formulation for delivery to a skin, etc.

It is to be understood that any delivery means for provision of the constructs, or cells of this invention, and/or to effect the methods of this invention, are to be considered as part of the invention.

The following are meant to provide materials, methods, and examples for illustrative purposes as a means of practicing/executing the present invention, and are not intended to be limiting.

EXAMPLES

Materials and Experimental Methods

Strains and Media
E. coli DH5α (Invitrogen) was used for routine transformations as described in the protocol. E. coli K12 (MG1655) and E. coli K12 PT5-dxs, PT5-idi, PT5-ispFD (provided by DuPont) were used for promoter engineering examples. In specified strains the lycopene expression was performed using the pAC-LYC plasmid (S. Z. Cunningham F X Jr, et al., Plant Cell 6, 1107-1121 (1994)) and assayed as described previously (H. Alper, et al., Metab Eng. 2005 May; 7(3):155-64). Assay strains were grown at 37° C. with 225 RPM orbital shaking in M9-minimal media (T. Maniatis, et al., Molecular cloning: a laboratory manual (Cold Spring Harbor Laboratory Press, Cold Spring Harbor, N.Y., 1982)) containing 5 g/L D-glucose. When necessary, the M9 media was supplemented with 0.1% casamino acids. All other strains and propagations were cultured at 37° C. in LB media. Media was supplemented with 68 µg/ml chloramphenicol, 20 µg/ml kanamycin, and 100 µg/ml ampicillin as necessary. Glucose monitoring was conducted using an r-Biopharm kit. Cell density was monitored spectrophotometrically at 600 nm. All PCR products and restriction enzymes were purchased from New England Biolabs and utilized Taq polymerase. M9 Minimal salts were purchased from US Biological and all remaining chemicals were from Sigma-Aldrich.

S. cerevisiae strain BY4741 (MATa; his3Δ1; leu2Δ0; met15Δ0; ura3Δ0) used in this study was obtained from EUROSCARF, Frankfurt, Germany. It was cultivated in YPD medium (10 g of yeast extract/liter, 20 g of Bacto Peptone/liter and 20 g glucose/liter). For yeast transformation, the Frozen-EZ Yeast Transformation II (ZYMO RESEARCH) was used. To select and grow yeast transformants bearing plasmids with URA3 as selectable marker, a yeast synthetic complete (YSC) medium was used containing 6.7 g of Yeast Nitrogen Base (Difco)/liter, 20 g glucose/liter and a mixture of appropriate nucleotides and amino acids (CSM-URA, Qbiogene) referred here as to YSC Ura⁻. Medium was supplemented with 1.5% agar for solid media. Yeast cells were routinely cultivated at 30° C. in Erlenmeyer flasks shaken at 200 rpm. For sorting single cells (TEF promoter mutations) by FACS into micro-titre plates, each well contained 200 µl YSC Ura⁻ supplemented with 10 mg/l ergosterol, 420 mg/l Tween 80 (K. Moller, et al., J Bacteriol 183, 2485-9 (April 2001)).

Library Construction

Nucleotide analogue mutagenesis was carried out in the presence of 20 µM 8-oxo-2'-deoxyguanosine (8-oxo-dGTP) and 6-(2-deoxy-β-D-ribofuranosyl)-3,4-dihydro-8H-pyrimido-[4,5-c][1,2]oxazin-7-one (dPTP) (M. Zaccolo, E. Gherardi, J Mol Biol 285, 775-83 (Jan. 15, 1999)). Using plasmid pZE-gfp(ASV) kindly provided by M. Elowitz as template (M. B. Elowitz, S. Leibler, Nature 403, 335-8 (Jan. 20, 2000)) along with the primers PL_sense_AatII: PRIMER SEQUENCE and PL_anti_EcoRI: CCGGAATTCGGT-CAGTGCGTCCTGCTGAT (SEQ ID NO: 1), 10 and 30 amplification cycles with the primers mentioned above were performed. The 151 bp PCR products were purified using the GeneClean Spin Kit (Qbiogene). Following digestion, the product was ligated overnight at 16° C. and transformed into library efficiency E. coli DH5α (Invitrogen). About 30,000 colonies were screened by eye from minimal media-casamino acid agar plates and 200 colonies, spanning a wide range in fluorescent intensity, were picked from each plate.

To create the TEF promoter mutation library for S. cerevisiae, the plasmid p416-TEF-yECitrine was used as a template for the error-prone PCR of TEF1 promoter using the primers ATTGGGACAACACCAGTGAATAATTCTTCACCTTTA-GACATTTTTCT (SEQ ID NO: 230) and ACGCCAAG-CGCGCAATTAACCCTCACTAAAGGGAACAAAAGCT-GGAGC (SEQ ID NO: 231). The mix of purified mutagenized PCR products was transformed into yeast together with p416-TEF which was cut with Sac I/Xba I before (in vivo cloning).

The CEN/ARS plasmid P416-TEF (D. Mumberg, R. Muller, M. Funk, *Gene* 156, 119-22 (Apr. 14, 1995)) containing the native TEF1 promoter from *S. cerevisiae*, the CYC1 terminator and URA3 gene as a selectable marker, was obtained from ATCC. The plasmid pKT140 was obtained from EUROSCARF. This plasmid contains the coding sequence of yECitrine, a yeast codon optimized version of the yellow fluorescent protein (M. A. Sheff, K. S. Thorn, *Yeast* 21, 661-70 (June 2004)) which was used as a reporter protein in this study. To clone the yECitrine gene downstream of the TEF promoter, the coding sequence of yECitrine was amplified via PCR from the plasmid pKT140 using the primer CGAGTTCTAGAAAAATGTCTAAAGGTGAAGAATTA-TTC (SEQ ID NO: 2) and TAGCGATCGATTTATTTGTA-CAATTCATCCATACC (SEQ ID NO: 3). The PCR product was cut with ClaI and XbaI and ligated to ClaI/XbaI restricted vector p416-TEF. The resulting plasmid is referred to as p416-TEF-yECitrine.

Library Characterization-Initial Characterization

About 20 µL of overnight cultures of library clones growing LB broth were used to inoculate 5 mL M9G medium supplemented with 0.1% w/v casamino acid (M9G/CAA) and the cultures were grown at 37° C. with orbital shaking. After 14 hours, a sample of the culture was centrifuged at 18,000×g for 2 minutes and the cells were resuspended in ice-cold water. Flow cytometry was performed on a Becton-Dickinson FACScan and the geometric mean of the fluorescence distribution of each clonal population was calculated. In order to ensure that bulk, population-averaged measurements could reflect the underlying single-cell behavior, only clones with clean, monovariate distributions of fluorescence were retained for further analysis. Twenty-seven clones were isolated in this way. Sequencing revealed that these 27 clones represented 22 unique promoter sequences.

Promoter Strength Metric

Shake flasks containing 50 mL of M9G/CAA medium were inoculated with 1% v/v of an overnight LB culture of a library clone. The culture turbidity ($A_{600\,nm}$) and fluorescence (Packard Fusion microplate fluorescence reader, Perkin-Elmer, Boston, Ma.) were monitored as a function of time. Fluorescence readings taken during the exponential growth phase were plotted as a function of turbidity. The best-fit slope to this line represents the exponential-phase steady-state concentration of GFP, $f_{SS}$. Because $f_{SS}$ is affected by the cell growth rate, oxygen-dependent maturation constant of GFP, and the protease-mediated degradation of GFP as well as the promoter-driven synthesis of new GFP, it is not a suitable metric for promoter strength. Instead, we used a previously published dynamic model (J. H. Leveau, S. E. Lindow, *J Bacteriol* 183, 6752-62 (December 2001)) that accounts for all of these factors. Under this model and under the assumption that the rate constant of protease-mediated degradation is the same for mature GFP as its precursor polypeptide, P, the rate of promoter-driven production of GFP, can be expressed as in Equation 1.

$$P = f_{SS}\mu\left(1 + \frac{\mu}{m}\right) + D\left(2 + \frac{\mu}{m}\right) \quad (1)$$

In Equation 1, µ is the growth rate, m is maturation constant for oxygen-dependent fluorophore activation of GFP, D is the first-order rate constant for protease-mediated degradation. Estimates of m and D of 1.5 $h^{-1}$ and 0.23 $h^{-1}$, respectively (B. P. Cormack, R. H. Valdivia, S. Falkow, *Gene* 173, 33-8 (1996); J. B. Andersen et al., *Appl. Environ. Microbiol.* 64, 2240-2246 (Jun. 1, 1998, 1998)), were as described. The parameters $f_{SS}$ and µ were measured separately for each member of the promoter library. P, in relative fluorescence units per absorbance unit per hour, was calculated from Equation 1 for each clone. Duplicate cultures were performed for each clone.

Transcriptional Analysis

Cultures inoculated as previously were grown for 3 hours and the total RNA was extracted from a 1.5 mL sample with a commercial kit (RNEasy, Qiagen Corp). All samples were diluted to a final concentration of 20 µg/mL and stored at −20° C. A commercial kit for RT-PCR (iScript One-Step RT-PCR Kit with SYBR Green, Bio-Rad) was used with a CCD-equipped thermal cycler (iCycler, Bio-Rad) for RT-PCR of the gfp transcript. Primers (sense-ATGGCTAGCAAAG-GAGAAGA (SEQ ID NO: 4) and antisense-ATCCATGC-CATGTGTAATCC (SEQ ID NO: 5)) were used at a final concentration of 100 nM and 20 ng of RNA was used as template in each 50 µL reaction. We performed duplicate cultures for each clone and duplicate extractions for each culture. The threshold cycles for each sample were calculated from the fluorescence data with proprietary software (Bio-Rad, Inc).

Chloramphenicol Resistance pZE-promoter-cat plasmids were created by PCR of the CAT gene from pACYC184 using primers CAT_Sense_MluI: CGACGCGTATTTCTGCCATTCATCCGCTTATTA-TCA (SEQ ID NO: 6) and CAT_Anti_KpnI: CGGGGTAC-CTTTCAGGAGCTAAGGAAGCTAAAATGGA (SEQ ID NO: 7) and ligated into the proper pZE-promoter construct which was previously digested by KpnI and MluI. Exponential-phase cultures grown in LB supplemented with kanamycin were plated onto LB agar supplemented with kanamycin and various concentrations of chloramphenicol ranging from 0 to 500 µg/ml. After overnight incubation at 37° C., the lowest concentration of chloramphenicol that inhibited the growth of a clone was recorded.

TEF Promoter Library Characterization

Measuring of specific fluorescence of TEF promoter library in *S. cerevisiae* was performed using cells harvested from the logarithmic phase during growth in shake flasks. Fluorescence of yECitrine was measured using a fluorescence spectrometer (HITACHI F-2500) with an excitation wavelength of 502 nm and an emission wavelength of 532 nm. The specific fluorescence is referred here to the ratio of fluorescence level measured and the optical density at 600 nm measured in the same cuvette.

Promoter Delivery Construction

Promoter replacements were conducted using PCR product recombination (K. A. Datsenko, B. L. Wanner, *PNAS* 97, 6640-6645 (Jun. 6, 2000, 2000)) using the pKD46 plasmid expressing the lambda red recombination system and pKD13 as the template for PCR. Promoter replacements were verified through colony PCR using the k1, k2 and kt primers along with the verification primers listed below. To create the cassette for promoter replacement, two fragments were amplified via PCR. Fragment 1 contained the promoter with primer homology to the upstream region of the endogenous promoter. Fragment 2 contained the kanamycin maker from pKD13 and had homology to an area downstream of the endogenous promoter or gene. These two fragments had an internal homology to each other of 25 basepairs to allow for self-annealing and subsequent amplification of a single cassette which was used (~100 ng) for the transformation. For the case of dxs, the entire gene was amplified and used as a third fragment which was annealed with the previous two. This provided higher recombination efficiency due to the increased homology region. The following sets of primers were used in the construction of these fragments:

```
ppc fragment-ppc-pze Sense:
GTTTGATAGCCCTGTATCCTTCACGTCGCATTGGCG    (SEQ ID NO: 8)
CGAATATGCTCGGCATCTTCCTTTCTCCTCTTTAAT
GAATTCGG pze-pkd13 shunt:
GAAGCAGCTCCAGCCTACACTCCGACGTCTAAGAAA    (SEQ ID NO: 9)
CCATTATTA pkd13 sense:
GTGTAGGCTGGAGCTGCTTC                    (SEQ ID NO: 10)

pkd13-ppc anti:
CATTTCCATAAGTTACGCTTATTTAAAGCGTCGTGA    (SEQ ID NO: 11)
ATTTAATGACGTAATCCGTCGACCTGCAGTTCGA verification:
CCGATCCCTGGCTATGAATGC                   (SEQ ID NO: 12)

dxs fragment-dxs-pze Sense:
TGGGTGGAGTCGACCAGTGCCAGGGTCGGGTATTTG    (SEQ ID NO: 13)
GCAATATCAAAACTCATCACTCCTCTTTAATGAATT
CGG pze-pkd13 shunt:
GAAGCAGCTCCAGCCTACACTCCGACGTCTAAGAAA    (SEQ ID NO: 14)
CCATTATTA pkd13 sense:
GTGTAGGCTGGAGCTGCTTC                    (SEQ ID NO: 15)

pkd13-dxs anti:
ACTCGATACCTCGGCACTGGAAGCGCTAGCGGACTA    (SEQ ID NO: 16)
CATCATCCAGCGTAATAAAATCCGTCGACCTGCAGT
TCGA dxs sense:
ATGAGTTTTGATATTGCCAAA                   (SEQ ID NO: 17)

dxs anti:
TTATGCCAGCCAGGCCTTG                     (SEQ ID NO: 18)

verification:
GTCAGAGCGTCGCGAATAGCCAGAC               (SEQ ID NO: 19)

Promoter Sequencing
Promoters were sequenced using
primers
PL_Left_seq:
AGATCCTTGGCGGCAAGAAA                    (SEQ ID NO: 20)
and PL_Right_seq:
GCCATGGAACAGGTAGTTTTCCAG                (SEQ ID NO: 21)
```

Example 1

Figure 2:
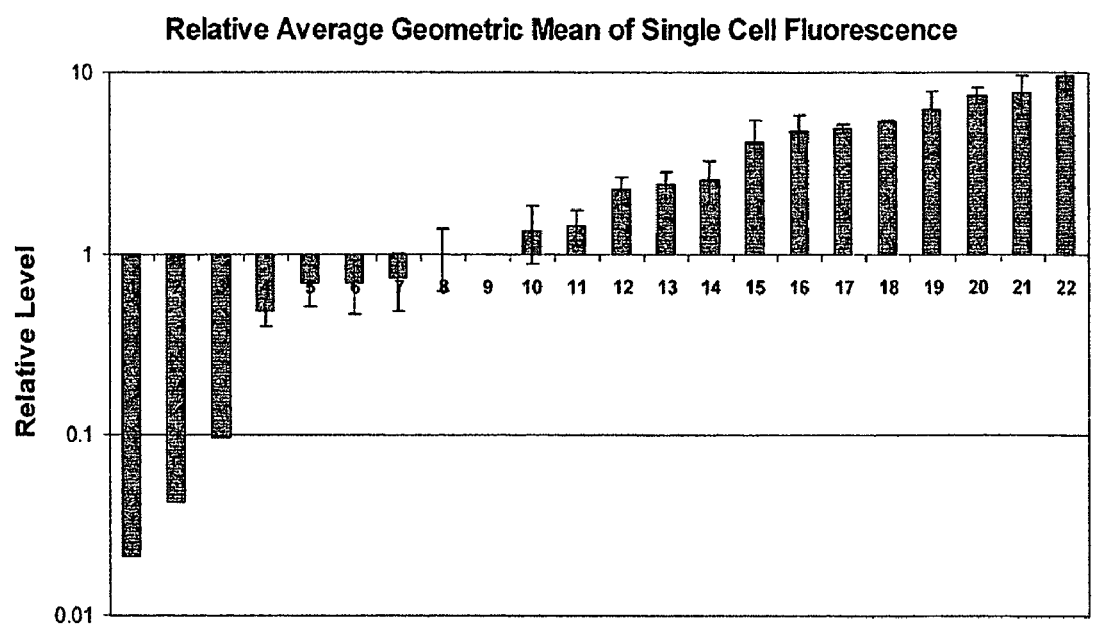
FIG. 2 depicts functional promoter library analysis using flow cytometry. The relative average geometric mean fluorescence of the members of the library exhibited a nearly 3 log fold range after 14 hours in a minimal media with 0.1% Casamino acids.

Construction of Constitutive Functional Promoters with Relatively Homogenous Single Cell Expression A derivative of the constitutive bacteriophage $P_L$-λ promoter was mutated through error-prone PCR, cloned into a reporter plasmid upstream of a low-stability GFP gene, and screened in *E. coli* based on the fluorescence signal in a glucose minimal medium, as described in the methods section, herein. Nearly 200 promoter mutants were selected which spanned a wide range of GFP fluorescence. Many of these initially screened promoters exhibited large variations in fluorescence between several trials or did not have an acceptable single-cell level homogeneity. Twenty-two mutants were finally chosen to form a functional promoter library based on reproducible and homogeneous single-cell fluorescence distributions as measured by flow cytometry, and FIG. 1 illustrates the process of creating and subsequently selecting these promoters. The relative average geometric means of single cell fluorescence obtained for the mutants is displayed in FIG. 2.

Figure 3:
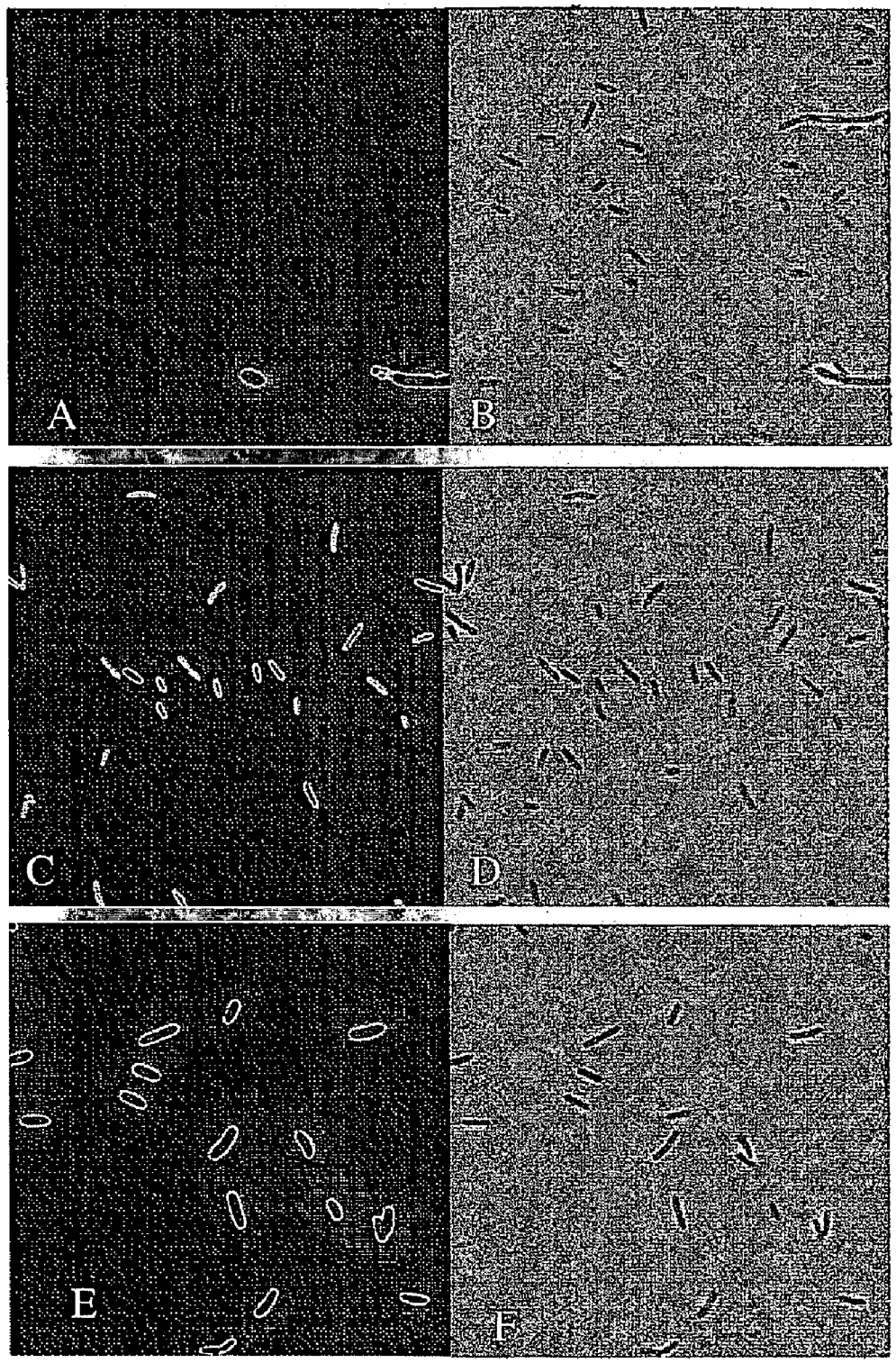
FIG. 3 is a series of micrographs of bacterial cultures bearing promoter-GFP reporter plasmids observed by both bright field (B, D, F) light field and fluorescence microscopy (A, C, E) using a Nikon E800 microscope equipped with a cooled CCD camera. A large proportion of screened clones had highly heterogeneous distribution of fluorescence. Only clones with comparatively homogenous GFP expression were chosen for further analysis.

Cultures bearing promoter-GFP reporter plasmids were grown to exponential phase in a glucose minimal medium supplemented with casamino acids, and a large proportion of screened clones had highly heterogeneous distribution of fluorescence, as determined via fluorescence microscopy (FIG. 3). Only clones with comparatively homogenous GFP expression were chosen for further analysis.

A multi-faceted characterization of each library member was conducted. The promoter strength in the library strains (in units of GFP fluorescence per cell per hour) was determined by measuring culture fluorescence and using a dynamic equation balancing GFP production and degradation (J. H. Leveau, S. E. Lindow, *J Bacteriol* 183, 6752-62 (December 2001)).

Figure 4:
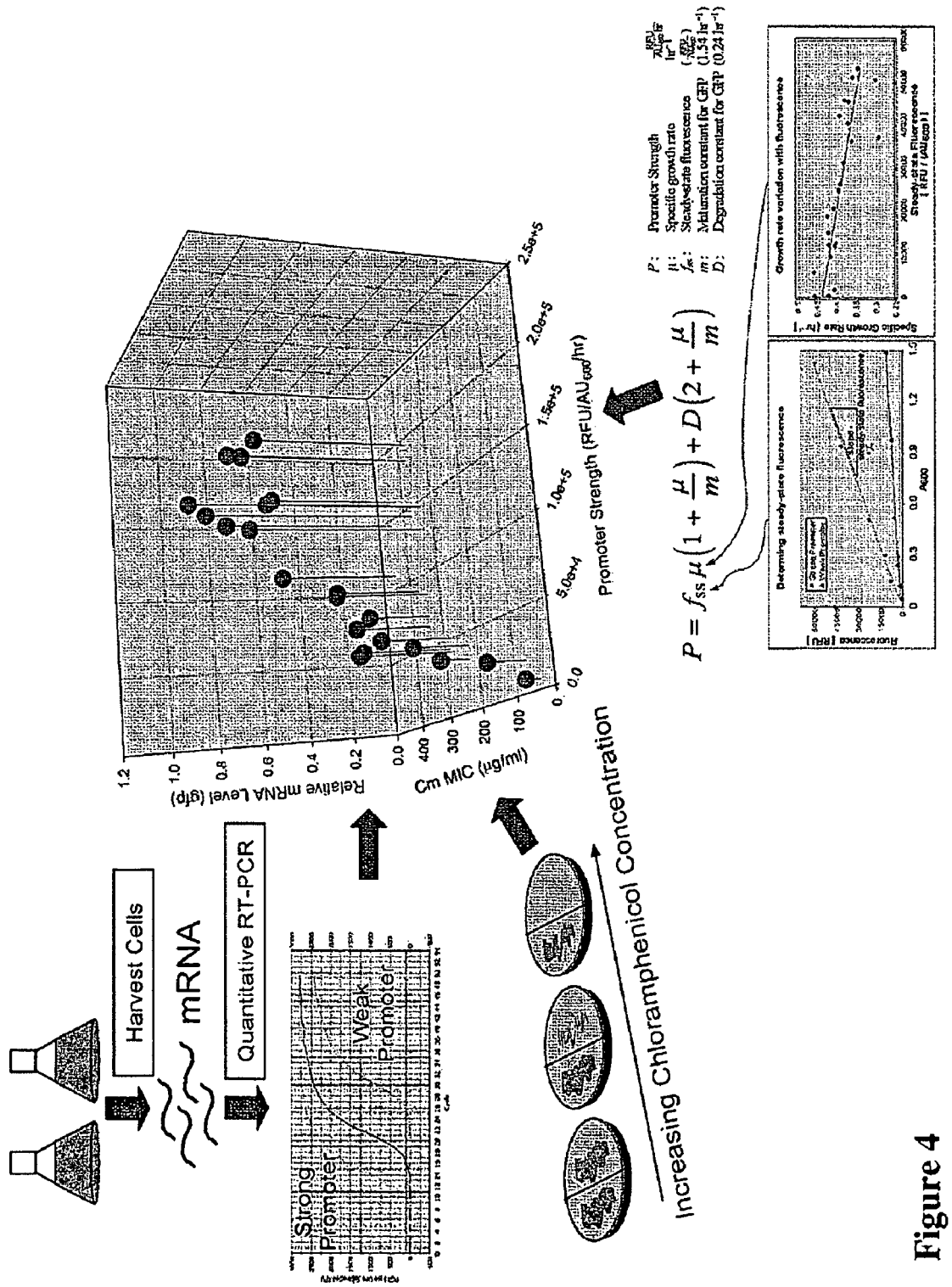
FIG. 4 demonstrates the characterization of the promoter library. Several orthogonal metrics were employed to characterize the promoter library and ensure the consistent behavior of all its members for various genes and culturing conditions. We show here three metrics that were chosen to quantify transcription of the promoters: (1) The dynamics of GFP production based on fluorescence, (2) measurement of the relative mRNA transcript levels in the cultures, and (3) testing of the MIC for chloramphenicol in an additional library of constructs where the promoter drove the expression of CAT. The overall strong correlation between the various metrics suggests a broad-range utility of the promoter library for a variety of genes and conditions.

Through replicate culturing, the promoter strength of the library members was found to span a 196-fold range with a mean spacing of 29% between adjacent members (FIG. 4). To characterize the promoter library directly at the transcriptional level, the relative mRNA levels of gfp transcripts in the above cultures were determined by quantitative RT-PCR. The high correlation between fluorescence and mRNA level (FIG. 4) confirmed that expression was transcriptionally controlled. The data was obtained where GFP fluorescence levels were modulated by the level of oxygen. In this way, selection for promoters, which had differential expression in high and low oxygen conditions was accomplished.

The mRNA level spanned a 325-fold range with a mean spacing of 32% between adjacent members. An "average promoter strength metric" was then assigned for each promoter by averaging the scaled mRNA and fluorescence data (Table 1).

TABLE 1

Characteristics of Promoters

| Promoter Name | Promoter Sequence | SEQ ID NO: | Promoter Strength | Relative mRNA | Cm MIC | Average Promoter Metric |
|---|---|---|---|---|---|---|
| AA | CAATTCCGACGTCTAAGA AACCATTATTATTATGAC ATTAACCTATAAAAATAG GCGTATCACGAGGCCCTT CCGTCTTCACCTCGAGTC CCTATCAGTGATAGATTG ACATCCCTATCAGTGATA GAAATACTGAGCACATCA GCAGGACGCACTGACC | 22 | 40,942.21 | 0.236732 | 2 | 0.218905 |

TABLE 1-continued

Characteristics of Promoters

| Promoter Name | Promoter Sequence | SEQ ID NO: | Promoter Strength | Relative mRNA | Cm MIC | Average Promoter Metric |
|---|---|---|---|---|---|---|
| B | CAATTCCGACGTCTAAGA AGCCATTATTATCATGAC ATTAACCTATAAAAGTAG GCGTGTCACAAGGCCCTT TCGTCTTCACCTCGAGTC CCTATCAGCGATAGAGAT TGACATCCCTATCAGTGA CCGAGATACTGAGCACAT CAGCAGGACGCACTGACC | 23 | 143,258.01 | 0.906126 | 372 | 0.815062 |
| BB | CAATTCCGACGTCTAAGA GACCATTATTATCGTGAC ATTAACCTATAAGAACAG GCGTGTCACGAGGCCCTT TCGTCTTCACCTCGAGTC CCTATCAGTGACAGAGAT TGACACCCTATCAGTGA TAGAGATACTGAGCACAT CAGCAGGACGCACTGACC | 24 | 85,320.056 | 0.407102 | 338 | 0.417495 |
| E | CAATTCCGACGCCTAAGA AACCATTATTATCATGAC ATTAGCCTATAAAAATAG GCGTACCACGAGGCCCTT TCGTCTTCACCTCGAGTC CCTATCAGTGATAGAGAT TGACACCCTATCAGTGA TAGAGATACTGAGCACAT CAGCAGGACGCACTGACC | 25 | 183,693.69 | 0.743061 | 375 | 0.83686 |
| F | CAATTCCGACGTCTAAGA AACCATTGTTATCGTGAC ATTAACCTATAANANTAG GCGTATCACGAGGCCCTT TCGCCTTCACCTCGAGTC CCTATCAGYGATAGAGAC CGACACCCCTATCAGTGA TAGGGATACTGGGCACAT CAGCAGGACGCACTGACC | 26 | 194,748.86 | 0.686715 | 372 | 0.836938 |
| II | CAATCCGACGTCTAAGAA ACCATTATTATCATGACA TTAACCTATAAAAATAGG CGTATCACGAGGCCCTTT CGTCTTCACCTCGAGTCC CTATCAGTGATAGACATG GACATCCCTATCAGTGAT AGAGATACTGAGCACATC AGCAGGACGCACTGACC | 27 | 5,781.541 | 70.063856 | 34 | 0.042617 |
| JJ | CAATTCCGACGTCTAAGA AACCATTATTATCATGAC ATTAACCTATAAAAATAG GCGTATCACGAGGCCCTT TCGTCTTCACCTCGAGTC CCTATCAGTGATAGAGAT TGACCTCCCTATCAGTGA TAGAGATACTGAGCACAT CAGCAGGACGCACTGACC | 28 | 18,896.294 | 0.159416 | 68 | 0.123911 |
| K | CAATTCCGACGTCTAAGA AACCATTATTATCATGAC ATTAACCTATAAAAATAG GCGTATCACGAGGCGCTC TCGTCTTCACCTCGAGTC CCTATCAGTGATAGGGAT TGACATCCCTATCAGTGA TAGAGACACTGGGCACAT CAGCAGGACGCACTGACC | 29 | 50,376.463 | 0.29891 | 282 | 0.274103 |

TABLE 1-continued

Characteristics of Promoters

| Promoter Name | Promoter Sequence | SEQ ID NO: | Promoter Strength | Relative mRNA | Cm MIC | Average Promoter Metric |
|---|---|---|---|---|---|---|
| L | CAATTCCGACGTCTAAGA AACCATTGTTATCATGAC ATTAACCTATAAAAATAG GCGTATCACGAGGCCCTT TCGTCTTCACCTCGAGTC CCTATCAGTGATAGAGAT TGACACCCTATCAGTGA CAGAGATACTGAGCACAT CAGCAGGACGCACTGACC | 30 | 29,869.65 | 0.757858338 | | 0.706716 |
| N | CAATTCCGACGTCTAAGA AACCATTATTATCATGAC ATTAACCTATAAAAATAG GCGTATCACGAGGCCCTT TCGTCTTCACCTCGAGTC CCTATCAGTGATAGAGAT TGACACCCTATCAGTGC TAGAGATACTGAGCACAT CAGCAGGACGCACTGACC | 31 | 90,494.778 | 0.366629372 | | 0.410482 |
| OO | CAATTCCGACGTCTAAGG AAACCATTATCATGACAT CAACCTATAAAAATAGGC GTATCACGAGGCCCTCTC GTCTCCACCTCAAGCTCC CTATCTAGTGATAGCGAT TGACATCCCTATCAGTGA CGGAGATATTGAGCACAT CAGCAGGACGCACTGACC | 32 | 996.99754 | 0.003075 | 17 | 0 |
| P | CAATTCCGACGTCTAGGA AACCGTTATATCATGACG CCGACCTATAAAGATAGG CGCGTCNCGAGGCCCTTC CGCCTTCACCTCGNGCTC CCTATCAGTAATAGAGAT TGACACCCTGTCAGTGA TAGGGATACTGAGCACAT CAGCAGGACGCACTGACC | 33 | 160,631.4 | 0.575729425 | | 0.69426 |
| P<sub>LTetO1</sub> | CAATTCCGACGTCTAAGA AACCATTATTATCATGAC ATTAACCTATAAAAATAG CCGTATCACGAGGCCCTT TCGTCTTCACCTCGAGTC CCTATCAGTGATAGAGAT TGACATCCCTATCAGTGA TAGAGATACTGAGCACAT CAGCAGGACGCACTGACC | 34 | 45,806.85 | 1 | 338 | 0.868513 |
| Q | CAATTCCGACGTCTAAGA AACCATTATTATCATGAC ATTAACCTATAAAAATAG GCGTATCACGAGGCCCTT TCGTCTTCACCTCGAGTC CCTATCAGTGATAGAGAT TGACATCCCTATCAGTGA TAGGGATACTGAGCACAT CAGCAGGACGCACTGACC | 35 | 95,662.5 | 0.736003450 | | 0.863916 |
| R | CAATTCCGACGTCTGAGA AGCCATTATTATCATGAC ATTAACCTATAAAAGTAG CCGTATCACGAGGCCCTT TCGTCTTCACCTCAAGCC CCTATCAGTGATAGAGAT TGACATCCCTATCAGTGA TAGAGACACTGAGCACAT CAGCAGGACGCACTGACC | 36 | 32,141.611 | 0.126381225 | | 0.141241 |

TABLE 1-continued

Characteristics of Promoters

| Promoter Name | Promoter Sequence | SEQ ID NO: | Promoter Strength | Relative mRNA | Cm MIC | Average Promoter Metric |
|---|---|---|---|---|---|---|
| S | CAATTCCGACGTCTAAGA AACCATTATTATCATGAC ATTAACCTATAAAAATAG GCGTATCACGAGGCCCTT TCGTCTTCACCTCGAGTC CCTATCAGTGATAGAGAT TGACATCCCTATCAGTGA TAGAGACACTGAGCACAT CAGCAGGACGCACTGACC | 37 | 41,376.671 | 0.393587 | 282 | 0.298443 |
| T | CAATTCCGACGTCTAAGA AGCCATTACTATCATGAC ATTAACCTATAGGAATAG GCGTATCACGGGGCCCTT CCGCCTTCACCTCGGATC CCTGTCAGTGCTAGAGAT TGACATCCCTACCGGTGA TAAAGATACTGAGCACAT CAGCAGGACGCACTGACC | 38 | 63,080.517 | 0.333052 | 338 | 0.323638 |
| U | CAATTCCGACGTCTAAGA AACCATTATTATCATGAC ACTAACCTATAAAAATAG GCGCATCACGAGGCCCTT TCGTCTCCACCTCAAGCT CCCTATCAGTGATAGAGA TTGACATCCCCGCCGGTG ATAGAGACACTGAGCACA TCAGCAGGACGCACTGAC C | 39 | 43,264.021 | 0.376762 | 282 | 0.294854 |
| V | CAATTCCGACGTCTGAGA GGCCATTATTATCGTGGC ATTGGCCTATAAAGGCAG GCGTGTCACGAGACCCTC TCGTCTCCGCCTCGGGTC CCTATCAATGGTAGAGAT TGACATCCCATCAGTGGT GGAGATACTGAGCACATC AGCAGGACGCACTGACC | 40 | 161,088.47 | 0.574349 | 450 | 0.694738 |
| W | CAATTCCGACGTCTAAGA AACCATTATTATCATGAC ATTAACCTATAAAAATAG GCGTATCACGAGGCCCTT TCGTCTTCACCTCGAGTC CCTATCAGTGATAGAGAT TGACATCCCTATCAGTGA TAGAGATACTGAGCACAT CAGCAGGACGCACTGACC | 41 | 109,462.28 | 0.525424 | 450 | 0.538349 |
| Y | CAATTCCGACGTCTAAGA AACCATTATTATCATGAC ATTAACCTATAAAAATAG GCGTATCACGAGGCCCTT TCGTCTTCACCTCGAGTC CCTATCAGTGATAGGGAT TGACATCCCTATCAGTGA TAGAGACACTGAGCACAT CAGCAGGACGCACTGACC | 42 | 70,234.541 | 0.273757 | 338 | 0.312272 |
| Z | CAATCCGACGTCTAAGAA ACCATTATTATCATGACA TTAGCCTATAAAAATAGG CGTATCACGAGGCCCTTT CGCCTTCACCTCGAGTCC CTATCGGTGACAGAGGTT GACATCCCTATCGGTGAT AGAGATACTGAGCACATC AGCAGGACGCACTGACC | 43 | 146,023.14 | 0.75968 | 450 | 0.748905 |

To verify the constitutive nature of all the promoters, each was redeployed into a new construct driving the reporter gene cat. Cultures bearing these constructs were assayed for resistance to chloramphenicol on a rich, solid-phase medium. The MIC spanned a 26-fold range. FIG. 4 displays the high correlation between these metrics of promoter performance. These data indicate that the library exhibits a high dynamic range which behaves similarly regardless of the gene being regulated. Moreover, these conditions test the promoter library in contrasting medium and growth environments (liquid minimal medium vs. solid complex medium) further underscoring the constitutive nature of the library promoters.

The following Table provides the sequence information for the 200 promoters which were sequenced, and screened for expression level differences.

TABLE 2

Promoters

| Promoter No. | Promoter Sequence | SEQ ID NO: |
|---|---|---|
| 1 | TTTGCNGGGCTTCCCAACCTTACCA-GAGGGCGCCCCAGCTGGCAATTCCCACGTCTAAGAAACCATTATTATCATGACATTAACCCG-CAAAAATAGGCGTATCACGAGGCCCCTTCGTCTTCACCTCGAGTCCCTATCAGTGATAGAAAT-TGACATCCCTATCAGCGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 44 |
| 2 | TTNNNANGGCTTCCCAACCTTACCA-GAGGGCGCCCCAGCTGGCAATTCCGACGTCTAAGAAACCATTATTATCATGACATTAAC-CTATAAAAACAGGCGTATCACGAGGCCCTTTCGTCTTCACCTCGAGTCCCTATCAGTGATAGAGAT-TGACATCCCTATCAGTGATAGAGACACTGAGCACATCAGCAGGACGCACTCACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 45 |
| 3 | TTTGCNGGGCTTCCCAACCTTACCA-GAGGGCGCCCCAGCTGGCAATTCCGACGTCTAAGAAACCATTATTATCATGACGTTAAC-CTATAAAAATAGGCGTATCACGAGGCCCTTTCGTCTTCACCTCCAGTCCCTATCAGTGATAGAGAT-TGACATCCCTATCAGTGATAGAAATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGCTGAAGGT-GATGCAACATACGGAAAACTTACCCTTAANTTTA | 46 |
| 4 | TTNNNNNGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGCGATAGAGAT-TGACATCCCTATCAGTGATAGGGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 47 |
| 5 | TTNNNNNGGCTTCCCAACCTTACCA-GAGGGCGCCCCAGCTGGCAATTCCGACGTCTAAGAAACCATTATTGTCATGACACTAACCTAT-GAAAACAGGCGTATCACGAGGCCCTTTCGTCTTCGCCTTGAGTCCCTATCAGTGATAGAGAT-TGACATCCCTATCAGTGATAGAGACACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGCAGAGGGTGAAGGT-GATGCAACATACGGAAAACTTACCCTTAANTTTA | 48 |

TABLE 2-continued

Promoters

| Promoter No. | Promoter Sequence | SEQ ID NO: |
|---|---|---|
| 6 | TTTGCNGGGCTTCCCAACCTTACCA-<br>GAGGGCGCCCCAGCTGGCAATTCCGACGTCTAAGAAA<br>CCATTATTATCATGACATTAACCTATAA-<br>GAGTAGGCGTATCACGAGGCCCTTTCGTCCTCAC<br>CTCGAGTCCCTATCAGTGGTAGAGAT-<br>TGACACCCCTATCAGTGATAGAGATACTGAGCACAT<br>CAGCAGGACGCACGACCGAATTCAT-<br>TAAAGAGGAGAAAGGTACCCCATGCGTAAAGGAGAAG<br>AACTTTTCACTGGAGTTGTCCCAATTCT-<br>TGTTGAATTAGATGGTGATGTTAATGGGCACAAA<br>TTTTCTGTCAGTGGAGAGGGTGAAGGTGATGCAACATACGGAAAACTTACCCCTTAANTTTA | 49 |
| 7 | TTTNNNNGGCTTCCCAACCTTACCA-<br>GAGGGCGCCCCAGCTGGCAATTCCGACGTCTGAGAAA<br>CCATTATTATCATGACATCAACCTATAA-<br>GAATAGGCGTATCACGAGGCCCTTTCGTCTTCAC<br>CTCGAGTCCCTATCAGTGGCAGAGAT-<br>TGACACCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 50 |
| 8 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAGATAGGCGTATCACGAGGCCCTTTCGTCTTCAC<br>CTCGAGTCCCTATCAGTGATAGAGAT-<br>TGACATCCCTATCAGTGATAGGGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTACATGGTGATGTTAATGGGCACAA<br>ATTTTCTGTCAGTGGAGAGGGTGAAGGT-<br>GATGCAACATACGGAAAACTTACCCTTAANTTTA | 51 |
| 9 | TTNNNNNGGCTTCCCAACCTTTCCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 52 |
| 10 | TTTGCNGGGCTTCCCAACCTTACCA-<br>GAGGGCGCCCCAGCTGGCAATTCCGACGTCTAAGGGA<br>TCATTATTACCATGACATTAAC-<br>CTATAAAGATAGGCGTATCACGAGGCCCTTTCGTCTTCAC<br>CTCGAGTCCCTATCAGTGATAGAGAT-<br>TGACATCCCTATCAGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAAATTTA | 53 |
| 11 | TTTGCNGGGCTTCCCAACCTTACCA-<br>GAGGGCGCCCCAGCTGGCAATTCCGACGTCTAGGAAA<br>CCATTATTATCATGACATCAAC-<br>CTATAAAAATAGGCGTGCCACGAGGCCCTTTCGTCTTCAC<br>CTCGGGTCCCTATCAGTGATAGAGAT-<br>TGACATCCCTACCAGTGATAGGGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGCAGAGGGTGAAGGT-<br>GATGCAACATACGGAAAACTTACCCTTAANTTTA | 54 |

TABLE 2-continued

Promoters

| Promoter No. | Promoter Sequence | SEQ ID NO: |
|---|---|---|
| 12 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 55 |
| 13 | TTNNNNNGGCTTCCCAACCTTACCA-<br>GAGGGCGCCCCAGCTGGCAATTCCGACGTCTAAGAAA<br>CCATTATTATCATGACATTAACCTAT-<br>GAAAATAGGCGTATCACGAGGCCCTTCCGTCTTCAC<br>CTCGAGTCCCTATCAGTGATAGAGAT-<br>TGACACCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTCTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 56 |
| 14 | TTTGCNGGGCTTCCCAACCTTACCA-<br>GAGGGCGCCCCAGCTGGCAATTCCGACGTCTAAGAAA<br>CCATTATTATCATGACATTAACCTATA-<br>GAAACAGGCGTATCGCGAGGCCCTTTCGTCTTCAC<br>CTCGAGTCCCTATCAGTGATAGAGAT-<br>TGACATCCCTATCAGTGATAGAAATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 57 |
| 15 | TTNNNNGGGCTTCCCAACCTTACCA-<br>GAGGGCGCCCCAGCTGGCAATTCCGACGTCTAGGAAA<br>CCATTATTATCATGGCATTAAC-<br>CTATAAAAGTAGGCGTATCACGAGGCCCTTTCGTCTTCAC<br>CTCGAGTCCCTATCAGTGGTAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 58 |
| 16 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGGGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 59 |
| 17 | TTTGCNGGGCTTCCCAACCTTACCA-<br>GAGGGCGCCCCAGCTGGCAATTCCGACGTCTAAGAAA<br>CCATTATTATCATGACATTAACCTG-<br>TAAAAATAGGCGTACCGCGAGGCCCCTTCGTCTTCAC<br>CTCGGGTCCCTATCGGTGATAGAGAT-<br>TGACACCCCTATTAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 60 |

TABLE 2-continued

Promoters

| Promoter No. | Promoter Sequence | SEQ ID NO: |
|---|---|---|
| 18 | TTTGCNGGGCTTCCCAACCTTACCA-<br>GAGGGCGCCCCAGCTGGCAATTCCGACGTCTAAGAAA<br>CCACTATTACCATGACATTAAC-<br>CTATAAAAATAGGCGTATCACGAGGCCCTTTCGTCTTCAC<br>CTCGAGTCCCTATCAGTGATAGAGAT-<br>TGACGCCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 61 |
| 19 | TTTGCNNGGCTTCCCAACCTTACCA-<br>GAGGGCGCCCCAGCTGGCAATTCCGACGTCTAAGAAA<br>CCATTATTATCGTGGCATTAAC-<br>CTATAAAGATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 62 |
| 20 | TTNNNNNGGCTTCCCAACCTTACCA-<br>CAGGGCGCCCCAGCTGGCAATTCCGACGTCTAAGAAA<br>CCATTATTATCATGACATTAAC-<br>CTATAAAAATAGGCGCATCACGAGGCCCTTTCGTCTTCAC<br>CTCGAGTCCCTATCAGTGATAGAGAT-<br>TGACACCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAATCTTACCCTTAANTTTA | 63 |
| 21 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 64 |
| 22 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCGGTGATAGAGAGACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 65 |
| 23 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTCTCGTCTTCAC<br>CTCGAGTCCCTATCAGTGATAGAGAT-<br>TGACATCCCTATCAGCGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA<br>TTTGCNGGGCTTCCCAACCTTACCA-<br>GAGGGCGCCCCAGCTGGCAATTCCGACGTCTAAGGAA | 66 |

TABLE 2-continued

Promoters

| Promoter No, | Promoter Sequence | SEQ ID NO: |
|---|---|---|
| | CCATTATTATCATGACATTAAC-<br>CTATAAAAATAGGCGTATCACGAGGCCCTTTCGTCTCCAC<br>CTCGAGTCCCTATCAGTGATAGAGAT-<br>TGACGTCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | |
| 24 | TTTGCNGGGCTTCCCAACCTTACCA-<br>GAGGGCGCCCCAGCTGGCAATTCCGACGTCTAAGAAA<br>CCATTATTATCATGACATTAACCTG-<br>TAAAAATAGGCGTACCACGAGGCCCCTTCGTCCTTAC<br>CCCGAGTCCCTGCCAGTGATAGAGAT-<br>TGACATCCCCATCACTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 67 |
| 25 | TTNNNNNGGCTTCCCAACCTTACCA-<br>GAGGGCGCCCCAGCTGGCAATTCCGACGTCTAAGAAA<br>CCATTATTATCATGACACTAAC-<br>CTATAAAAATAGGCGCATCACGAGGCCCTTTCGTCTTCAC<br>CTCGAGTCCCTATCAGTGATAGAGAT-<br>TGACATCCCTATCAGTGATAGAGACACTGAGCACAT<br>CAGCAGGACGCACTGACGGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 68 |
| 26 | TTNNNNGGGCTTCCCAACCTTACCA-<br>GAGGGCGCCCCAGCTGGCAATTCCGACGCCTACGAAG<br>CCATTGTTATCATGACATTAAC-<br>CTATAAAGACAGGCGTATCACGAGGCCCCTTCGCGTTCAC<br>CCCGGGTCCCTATCAGTGATAGAGAT-<br>TGACATCCCTATCGGTGATAGAGACACTGGGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 69 |
| 27 | TTTGCNNGGCTTCCCAACCTTACCA-<br>GAGGGCGCCCCAGCTGGCAATTCCGACGTCTAAGGAA<br>CCATTATTATCATGACATTAAC-<br>CTATAAAAGTAGGCATACCATGAGGCCCTCCCGCCTTCAC<br>CTCGAGTCCTTATCAGTGGTAGAGGT-<br>TGACGCCCCTATCGGCGATGGAGATACTGGGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAT<br>ATTTTCTGTCAGTGGAGAGGGTGAAGGT-<br>GATGCAACATACGGAAAACTTACCCTTAANTTTA | 70 |
| 28 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCACGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 71 |

TABLE 2-continued

Promoters

| Promoter No, | Promoter Sequence | SEQ ID NO: |
|---|---|---|
| 30 | TTNNNNNGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATCGTGATGTTAATGGGCACAAATTTTCTGTCAGTGGAGAGGGTGAAGGT-GATGCAACATACGGAAAACTTACCCTTAANTTTA | 72 |
| 31 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 73 |
| 32 | TTNNNNNGGCTTCCCAACCTTACCA-GAGGGCGCCCCAGCTGGCAATTCCGACGTCTAAGAGACCATTATTATCATGACATTAAC-CTATAAAAATAGGCGTATCACGAGGCCCTTTCGTCTTCACCTCGAGTCCCTATCAGTGGTAGAGAT-TGACATCCCTATCAGTGATAGAGATACTGAGCACATCAGCAGGACGCACTGACCGAATTCAT-TAAAGAGGAGAAAGGTACCGCATCCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 74 |
| 33 | TTNGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATA-GAGATACTGAGCACATCAGCAGGACGCACTGACCGAATTCATTAAAGAGGAGAAAGGTACCGCATGCG-TAAAGGAGAAGAAATTTTCACTGGAGTTGTCCCAATTCTTGTTGAATTAGATGGTGATGT-TAATGGGCACAAATTTTCTGTCAGTGGAGAGGGTGAAGGTGATGCAACATACGGAAAACTTACCCTTAAATTTA | 75 |
| 34 | TTNNNNNGGCTTCCCAACCTTACCA-GAGGGCGCCCCAGCTGGCAATTCCGACGTCTGAGAAACCATTATTGTCATGACATTAAC-CTATAAAGATAGGCGTATCACGAGGCCCTTTCGTCTTCACCTCGAGTCCCTATCAGTGATAGAGAT-TGACATGCCTATCAGTGGTAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 76 |
| 35 | TTNNNNNGGCTTCCCAACCTTACCA-GAGGGCGCCCCAGCTGGCAATTCCGACGTCTAGGAAACCATTATTGTCATGACATTAACCTATAA-GAATAGGCGTATCACGAGGCCCTTTCGTCCTCACCCCGGGTCCCTATCAGTGATAGAGAT-TGACATCCCTACCAGTGATAAAGATACTGGGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 77 |

TABLE 2-continued

Promoters

| Promoter No. | Promoter Sequence | SEQ ID NO: |
|---|---|---|
| 36 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGCCCCTATCAGTGATAGAGAT-<br>TGACACCCCTACCAGTGACAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATCTTAATGGGCACAA<br>ATTTTCTGTCAGTGGAGAGGGTGAAGGT-<br>GATGCAACATACGGAAAACTTACCCTTAANTTTA<br>>134 | 78 |
| 37 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 79 |
| 38 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTAAGAG-<br>GAGAAAGGTACCGCATGCGTAAAGGAGAAGAACT<br>TTTCACTGGAGTTGTCCCAATTCTTGT-<br>TGAATTAGATGGTGATGTTAATGGGCACAAATTTT<br>CTGTCAGTGGAGAGGGTGAAGGTGATGCAACATACGGAAAACTTACCCTTAANTTTA | 80 |
| 39 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCSTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTCAAGGT-<br>GATGCAACATACGGAAAACTTACCCTTAANTTTA | 81 |
| 40 | TTNNNANGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 82 |
| 41 | TTTGCNGGGCTTCCCAACCTTACCA-<br>GAGGGCGCCCCAGCTGGCAATTCCGACGTCTAAGAAA<br>CCATTATTATCATGACATTAACCTA-<br>CAAAGATAGGCGTATCATGGGGCCCTTTCGTCTTCAC<br>CTCGAGTCCCTATCAGTGATAGAGAT-<br>TGACACCCCTATCAGTGACAGAGATACTGGGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 83 |

TABLE 2-continued

Promoters

| Promoter No. | Promoter Sequence | SEQ ID NO: |
|---|---|---|
| 42 | TTNNNNNGGCTTCCCAACCTTACCA-GAGGGCGCCCCAGCTGGCAATTCCGACGTCTAAGAAACCACTATTACCATGACATTAAC-CTATAAAAATAGGCGTATCACGAGGCCCTTTCGTCTTCACCTCGAGTCCCTATCAGTGACAGAGAT-TGACACCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 84 |
| 43 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 85 |
| 44 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 86 |
| 45 | TTNNNNNGGCTTCCCAACCTTAGCA-GAGGGCGCCCCAGCTGGCAATTCCGACGTCTAAGAAACCATTATTATCATGACATTGACCTA-CAAAAGTAGGCGTATCACGAGGCCCTTTCGTCTTCACCTCGAGTCCCTATCAGTGATAGAGAT-TGACATCCCTATCAGTGATAGAAATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 87 |
| 46 | TTNNNNNGGCTTCCCAACCTTACCA-GAGGGCGCCCCAGCTGGCAATTCCGACGTCTAAGAAACCATTATTATCATGACATTAAC-CTATAAAAACAGGCGTATCACGAGGCCCTTTCGTCTTCACCTCGGGTCCCTATCAGTGATAGAGAT-TGACATCCCTATCAGTGATAGAGACACTGAGCGCATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 88 |
| 47 | TNNNNNNNNNTTTGCNGGGCTTCCCAAC-CTTACCAGAGGGCGCCCCAGCTGGCAATTCCGACGTCTAAGAAACCATTATTATCATGACAT-TAACCTATAGAAATAGGCGTATCACGAGGCCCTCTCGTCTCCACCTCGAGCCCCTGTCAG-TAATAGGGATTGACACCCCTACCAGTGATAGAGACACTGAGCACATCAGCAGCACGCACTGAC-CGAATTCATTAAAGACGAGAAAGGTACCGCATGCGTAAAGGAGAAGAACTTTTCACTGGAGT-TGTCCCAATTCTTGTTGAATTAGATGGTGATGTTAATGGGCACAAATTTTCTGTCAGTG-GAGAGGGTGAAGGTGATGCAACATACGGAAAACTTACCCTTAANTTTA | 89 |

TABLE 2-continued

Promoters

| Promoter No. | Promoter Sequence | SEQ ID NO: |
|---|---|---|
| 48 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGCTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-CATGCAACATACGGAAAACTTACCCTTAANTTTA | 90 |
| 49 | CGCGTAAAGAAGAACAGCTTGT-CACGCGTTTTGTGCCAATTCTTGATGAACGAGGCGGTCTGGTCAATCGGGATAAATGTCGCCTGAGTGGATAGGGTGAAGGTGATACAACATGCCGAA | 91 |
| 50 | TTNNNNNGGCTTCCCAACCTTACCA-GAGGGCGCCCCAGCTGGCAATTCCGACGTCTAAGGGGCCATTATTATCATGACGCTAACCTGT-GAAGCTAGGCGTATCACGAGGCCCTTCCGTCTTCGCCTTGAGTCCCTATTAGTGATAGAGGT-TGACGCCCCTATCAGTGGTAGAGATACTGGGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 92 |
| 51 | CAAATTTTCGGTAAGTG-GAAGGGGCGTGGGTGATGCAACAGCAGGAAACCTGCTGGATAGCTCTANANNNNCNNNNNNNNGNNTGNNNNNT | 93 |
| 52 | TTTNNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATA-GAGATACTGAGCACATCAGCAGGACGCACTGACCGAATTCATTAAAGAGGAGAAAGGTACCGCATGCG-TAAAGGAGAAGAACTTTTCACTGGAGTTGCCCAATTCTTGTTGAATTAGATGGTGATGT-TAATGGGCACAAATTTTCTGTCAGTGGAGAGGGTGAAGGTGATGCAACATACGGAAAACTTACCCTTAANTTTA | 94 |
| 53 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 95 |
| 54 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 96 |
| 55 | TTNNANGGCTTCCCAACCTTACCAGAGGGCGCCCCAGCTGGCAATTCCGACGTCTAAGAAGCCATTATTATCATGGCATTAAC-CTATAAAAATAGGCGTATCACGAGGCCCTTTCGTCTTCACCCCGAGTCCCTATCAGTGATAGAGAT-TGACATCCCTATCAGTGATAGAGGTACTGAGCACAT | 97 |

TABLE 2-continued

Promoters

| Promoter No. | Promoter Sequence | SEQ ID NO: |
|---|---|---|
| | CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | |
| 56 | TTNNNANGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 98 |
| 57 | TTCCGACGTCTAAGAAACCATTATTAT-<br>CATGACATTAACCTATAAAAATAGGCGTATCACGA<br>GGCCCTTTCGTCTTCACCTCGAGTC-<br>CCTATCAGTGATAGAGATACTGAGCACATCAGCAGGA<br>CGCACTGACCGAATTCATTAAAGAG-<br>GAGAAAGGTACCGCATGCGTAAAGGAGAAGAACTTTT<br>CACTGGAGTTGTCCCAATTCTTGT-<br>TGAATTAGATGGTGATGTTAATGGGCACAAATTTTCTG<br>TCAGTGGAGAGGGTGAAGGTGATGCAACATACGGAAAACTTACCCTTAANTTTATNNNC | 99 |
| 58 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTANNTNNNNNA | 100 |
| 59 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCCCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGACAGGGTGAA<br>GGTGATGCAACATACGGAAAACTTACCCTTAANTTTA | 101 |
| 60 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 102 |
| 61 | TTNNNANGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 103 |

TABLE 2-continued

Promoters

| Promoter No. | Promoter Sequence | SEQ ID NO: |
|---|---|---|
| 62 | TTTGCNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 104 |
| 63 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 105 |
| 64 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCCAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 106 |
| 65 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGACAT-<br>ACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 107 |
| 66 | ANTTTGCNNGGCTTCCCAACCTTACCA-<br>GAGGGCGCCCCAGCTGGCAATTCCGACGTCTAAGA<br>AACCATTATTATCATGACATTAAC-<br>CTATAAAAATAGGCGTATCACGAGGCCCTTTCGTCTTC<br>ACCTCGAGTCCCTATCAGTGATACA-<br>GATACTGAGCACATCAGCAGGACGCACTGACCGAATT<br>CATTAAAGAGGAGAAAGGTACCGCAT-<br>GCGTAAAGGAGAAGAACTTTTCACTGGAGTTGTCCC<br>AATTCTTGTTGAATTAGATGGTGATGT-<br>TAATGGGCACAAATTTTCTGTCAGTGGAGGGTG<br>AAGGTGATGCAACATACGGAAAACTTACCCTTAANTTTA | 108 |
| 67 | TTNNNNNGGCTTCCCAACCTTACCA-<br>GAGGGCGCCCCAGCTCGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGC-<br>CTAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 109 |
| 68 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC | 110 |

TABLE 2-continued

Promoters

| Promoter No. | Promoter Sequence | SEQ ID NO: |
|---|---|---|
| | CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | |
| 69 | TTNNNANGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 111<br>111 |
| 70 | AANNNNNTNNNNNNNANTTTGCNGGGCT-<br>TCCCAACCTTACCAGAGGGCGCCCCAGCTGGCAA<br>TTCCGACGTCTAAGAAACCATTATTAT-<br>CATGACATTAACCTATAAAAATAGGCGTATCACGA<br>GGCCCTTTCGTCTTCACCTCGAGTC-<br>CCTATCAGTGATAGAGATACTGAGCACATCAGCAGGA<br>CGCACTGACCGAATTCATTAAAGAG-<br>GAGAAAGGTACCGCATGCGTAAAGGAGAAGAACTTTT<br>CACTGGAGTTGTCCCAATTCTTGT-<br>TGAATTAGATGGTGATGTTAATGGGCACAAATTTTCTG<br>TCAGTGGAGAGGGTGAAGGTGATGCAACATACGAAAACTTACCCTTAANTTTA | 112 |
| 71 | GNNNTNNNNNNNANTTTGCNGGGCTTC-<br>CCAACCTTACCAGAGGGCGCCCCAGCTGGCAATTC<br>CGACGTCTAAGAAACCATTATTATCAT-<br>GACATTAACCTATAAAAATAGGCGTATCACGAGGC<br>CCTTTCGTCTTCACCTCGAGTCCCTAT-<br>CAGTGATAGAGATACTGAGCACATCAGCAGGACGC<br>ACTGACCGAATTCATTAAAGAG-<br>GAGAAAGGTACCGCATGCGTAAAGGAGAAGAACTTTTCAC<br>TGGAGTTGTCCCAATTCTTGTTGAATTA-<br>GATGGTGATGTTAATGGGCACAAATTTTCTGTCA<br>GTGGAGAGGGTGAAGGTGATGCAACAT-<br>ACGGAAAACTTACCCTTAAATTTATNNNCNNNNNN<br>NNNNNNC | 113 |
| 72 | TTTGCNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 114 |
| 73 | TTNNNNNNNNTTNNNANGGCTTCCCAAC-<br>CTTACCAGAGGGCGCCCCAGCTGGCAATTCCGAC<br>GTCTAAGAAACCATTATTATCATGACAT-<br>TAACCTATAAAAATAGGCGTATCACGAGGCCCTT<br>TCGTCTTCACCTCGAGTCCCTATCAGT-<br>GATAGAGATACTGAGCACATCAGCAGGACGCACTG<br>ACCGAATTCATTAAAGAGGAGAAAGG-<br>TACCGCATGCGTAAAGGAGAAGAACTTTTCACTGGA<br>GTTGTCCCAATTCTTGTTGAATTAGATG-<br>GTGATGTTAATGGGCACAAATTTTCTGTCAGTGG<br>AGAGGGTGAAGGTGATGCAACATACGGAAAACTTACCCTTAANTTTA | 115 |
| 74 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT | 116 |

TABLE 2-continued

Promoters

| Promoter No, | Promoter Sequence | SEQ ID NO: |
|---|---|---|
| | CAGCAGGACGCACTGACCGAATTAT-<br>TAAAGAGGAGAAAGGTACCGCATGCGTAAAGGAGAAG<br>AACTTTTCACTGGAGTTGTCCCAATTCT-<br>TGTTGAATTAGATGGTGATGTTAATGGGCACAAA<br>TTTTCTGTCAGTGGAGAGGGTGAAGGTGATGCAACATACGGAAAACTTACCCTTAANTTTA | |
| 75 | CNNNNNANTTTGCNGGGCTTCCCAACCT-<br>TACCAGAGGGCGCCCCAGCTGGCAATTCCGACGT<br>CAACCTATAAAAATAGGCGTATCACGAG-<br>GCCCTCTCGTCTTCACCTCGAGTCCCTATCAGTG<br>ATAGAGATTGACACCCCTATCAGTGATA-<br>GAGATACTGAGCACATCAGCAGGACGCACTGACC<br>GAATTCATTAAAGAGGAGAAAGGTACCG-<br>CATGCGTAAAGGAGAAGAACTTTTCACTGGAGTT<br>GTCCCAATTCTTGTTGAATTAGATGGT-<br>GATGTTAATGGGCACAAATTTTCTGTCAGTGGAGA<br>GGGTGAAGGTGATGCAACATACGGAAAACTTACCCTTAANTTTA | 117 |
| 76 | AANNNNNNNNNNNNNNTTTGCNGGGCT-<br>TCCCAACCTTACCAGAGGGCGCCCCAGCTGGCAA<br>TTCCGACGTCTAAGAAACCATTATTAT-<br>CATGACATTAACCTATAGAAACAGGCGTATCACGA<br>GGCCCTTTCGTCTTCACCTCGAGTTC-<br>CTATCAGTGATAGAGACTGACATCCCTATCAGTGAT<br>AGAGATACTGAGCACATCAGCAGGACG-<br>CACTGACCGAATTCATTAAAGAGGAGAAAGGTACC<br>GCATGCGTAAAGGAGAA-<br>GAACTTTTCACTGGAGTTGTCCCAATTCTTGTTGAATTAGATGGT<br>GATGTTAATGGGCACAAATTTTCTGT-<br>CAGTGGAGAGGGTGAAGGTGATGCAACATACGGAAA<br>ACTTACCCTTAANTTTA | 118 |
| 77 | TTTGCNGGGCTTCCCAACCTTACCA-<br>GAGGGCGCCCCAGCTGGCAATTCCGACGTCTAAGAAG<br>CCATTATTGTCATGACATTAAC-<br>CTATAAAGATAGGCGTATTACGAGGCCCTCTCGTCTTCAC<br>CTCGAGTCCCTATCGGTGATAGAGAT-<br>TGACATCCCTGTCAGTGGCAGGGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGCGCACAA<br>ATTTTCTGTCAGTGGAGAGGGTGAAGGT-<br>GATGCAACATACGGAAAACTTACCCTTAANTTTA | 119 |
| 78 | TTNNNNNGGCTTCCCAACCTTACCA-<br>GAGGGCGCCCCAGCTGGCAATTCCGACGTCTAAGAAA<br>CCATTATTATCATGACATTAGC-<br>CTATAAAAATAGGCGTATCACGAGGCCCTTTCGTCTTCAC<br>CTCGAGCCCCTACCAGTGACAGACGT-<br>TGACGTCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 120 |
| 79 | ANNNNNNNNNNTTTGCNGGGCTTC-<br>CCAACCTTACCAGAGGGCGCCCCAGCTGGCAATTCCGA<br>CGTCTAAGAAACCATTATTATCATGA-<br>CATTAACCTATAAAGATAGGCGTATCACGAGGCCCT<br>TCCGTCTTCACCTCGAGTCCCTATCAGT-<br>GATAGAGGTTGACGTCCCTATCAGTGGTAGAGAT<br>ACTGAGCACATCAGCAGGACGCACTCAC-<br>CGAATTCATTAAAGAGGAGAAAGGTACCGCATGC<br>GTAAAGGAGAAGAACTTTTCACTGGAGT-<br>TGTCCCAATTCTTGTTGAATTAGATGGTGATGTT<br>AATGGGCACAAATTTTCTGTCAGTG-<br>GAGAGGGTGAAGGTGATGCAACATACGGAAAACTTAC<br>CCTTAANTTTA | 121 |
| 80 | TTTGCNGGGCTTCCCAACCTTACCA-<br>GAGGGCGCCCCAGCTGGCAATTCCGACGTCTAAGGGG<br>TCATTATTATCATGACGCTAACCTGT-<br>GAAGGTAGGCGTATCACGAGGCCCTTCCGTCTTCGC<br>CTTGAGTCCCTATTAGTGATAGAGGT-<br>TGACGCCCTATCAGTGGTAGAGATACTGGGCACAT | 122 |

TABLE 2-continued

Promoters

| Promoter No. | Promoter Sequence | SEQ ID NO: |
|---|---|---|
| | CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | |
| 81 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACACCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 123 |
| 82 | TTTGCNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTACCACGAGGCCCTTTCGTCTTCAC<br>CTCGAGTCCCTACCAGTGATAGAGAT-<br>TGACATCCCTATCAGTGATAGAAATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 124 |
| 83 | TTTGCAGGGCTTCCCAACCTTACCA-<br>GAGGGCGCCGCAGCTGGCAATTCCGACGTCTAAGGAA<br>CCATTATTATCATGACATTAAC-<br>CTATAAAAATAGGCGTATCACGAGGCCCTTTCGTCTTCAC<br>CTCGAGTCCCTATCAGTGGTAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTCAATTAGATGGTGATGTTAATGGGCACAA<br>ATTTTCTGTCAGTGGAGAGGGTGAAGGT-<br>GATGCAACATACGGAAAACTTACCCTTAANTTTA | 125 |
| 84 | TTNNNNNGGCTTCCCAACCTTACCA-<br>GAGGGCGCCCCAGCTGGCAATTCCGACGTCTAAGAAA<br>CCATTATTATTATGACATTAAC-<br>CTATAAAAATAGGCGTATCACGAGGCCCTTCCGTCTTCAC<br>CTCGAGTCCCTATCAGTGATAGAGAT-<br>TGACATCCCTATCAGTGATAGAAATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 126 |
| 85 | TTNNNNNGGCTTCCCAACCTTACCA-<br>GAGGGCGCCCCAGCTGGCAATTCCGACGTCTAAGAAG<br>CCATTATTATCATGACATTAAC-<br>CTATAAAAGTAGGCGTGTCACAAGGCCCTTTCGTCTTCAC<br>CTCGAGTCCCTATCAGCGATAGAGAT-<br>TGACATCCCTATCAGTGACCGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 127 |
| 86 | TTNNNNNGGCTTCCCAACCTTACCA-<br>GAGGGCGCCCCAGCTGGCAATTCCGACGTCTAAGAGA<br>CCATTATTATCGTGACATTAACCTATAA-<br>GAACAGGCGTGTCACGAGGCCCTTTCGTCTTCAC<br>CTCGAGTCCCTATCAGTGACAGAGAT-<br>TGACACCCCTATCAGTGATAGAGATACTGAGCACAT | 128 |

TABLE 2-continued

Promoters

| Promoter No. | Promoter Sequence | SEQ ID NO: |
|---|---|---|
| | CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | |
| 87 | TTTGCNGGGCTTCCCAACCTTACCA-<br>GAGGGCGCCCCAGCTGGCAATTCCGACGTCTAAGAAA<br>CCATTATTACCATGCCATTAAC-<br>CTATAAAAATAGGCGTATCACGAGGCCCTTTCGCCTTCAC<br>CTCGAGTCCCTATCAGTGATAGAGAT-<br>TGACACCCCTATCACTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 129 |
| 88 | TTNNNNNGGCTTCCCAACCTTACCA-<br>GAGGGCGCCCCAGCTGGCAATTCCGACGCCTAAGAAA<br>CCATTATTATCATGACATTAGC-<br>CTATAAAAATAGGCGTACCACGAGGCCCTTTCGTCTTCAC<br>CTCGAGTCCCTATCAGTGATAGAGAT-<br>TGACACCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 130 |
| 89 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGACT-<br>GACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 131 |
| 90 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACACCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 132 |
| 91 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTCTCGTCTTCAC<br>CTCGAGTCCCTATCAGTGATAGGGAT-<br>TGACATCCCTATCAGTGATAGAGACACTGGGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 133 |
| 92 | TTNNNNNGGCTTCCCAACCTTACCA-<br>GAGGGCGCCCCAGCTGGCAATTCCGACGTCTAAGAAA<br>CCATTGTTATCATGACATTAAC-<br>CTATAAAAATAGGCGTATCACGAGGCCCTTTCGTCTTCAC<br>CTCGAGTCCCTATCAGTGATAGAGAT-<br>TGACACCCCTATCAGTGACAGAGATACTGAGCACAT | 134 |

TABLE 2-continued

Promoters

| Promoter No. | Promoter Sequence | SEQ ID NO: |
|---|---|---|
| | CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTACATGGTGATGTTAATGGGCACAA<br>ATTTTCTGTCAGTGGAGAGGGTGAAGGT-<br>GATGCAACATACGGAAAACTTACCCTTAAATTTA | |
| 93 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTGTCTTCAC<br>CTCGAGCCCCTATCAGTGATAGAGAT-<br>TGACACCCGTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAAATTTA | 135 |
| 94 | TTNNNNNGGCTTCCCAACCTTACCA-<br>GAGGGCGCCCCAGCTGGCAATTCCGACGTCTAAGAAA<br>CCATTACTATCATGACATTAAC-<br>CTATAAAAGTAGGCGTATCACGAGGCCCTTTCGTCTTCAC<br>CTCGAGTCCCTATCAGTGATAGAGAT-<br>TGACATCTCTATCAGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 136 |
| 95 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACACCCTATCAGTGCTAGAGATACTGAGCACAT<br>CAGCAGGACGCACTGACCGATTCAT-<br>TAAAGAGGAGAGGTACCGCATGCGTAAAGGAGCACAT<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 137 |
| 96 | TTNNNNNGGCTTCCCAACCTTACCA-<br>GAGGGCGCCCCAGCTGGCAATTCCGACGTCTAAGAAA<br>CCATTATTATCATGACATTAACCCAT-<br>AAAAATAGGCGTATCATGAGGCCCTTTCGTCTTCAC<br>CTCGAGTCCCTATCAGTGATAGAGAT-<br>TGACACCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 138 |
| 97 | TTTGCNNGGCTTCCCAACCTTACCA-<br>GAGGGCGCCCCAGCTGGCAATTCCGACGTCTAGGAAA<br>CCGTTATTATCATGACGCCAAC-<br>CTATAAAGATAGGCGTGTCACGAGGCCCTTTCGCCTTCAC<br>CTCGAGCCCCTATCAGTGATAGAGAT-<br>TGACACCCCTGTCAGTGATAGGGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGATTAGATGGTGATGTTAATGGGCACAAA<br>ATTTTCTGTCAGTGGAGAGGGTGAAGGT-<br>GATGCAACATACGGAAAACTTACCCTTAAATTTA | 139 |
| 98 | TTTGCNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGGGATACTGAGCACAT | 140 |

TABLE 2-continued

Promoters

| Promoter No, | Promoter Sequence | SEQ ID NO: |
|---|---|---|
| | CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | |
| 90 | TTNNNNNGGCTTCCCAACCTTACCA-<br>GAGGGCGCCCCAGCTGGCAATTCCGACGTCTGAGAAG<br>CCATTATTATCATGACATTAAC-<br>CTATAAAAGTAGGCGTATCACGAGGCCCTTTCGTCTTCAC<br>CTCAAGCCCCTATCAGTGATAGAGAT-<br>TGACATCCCTATCAGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAAATTTA | 141 |
| 91 | TTNGNANGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 142 |
| 92 | TTNNNNGGGCTTCCCAACCTTACCA-<br>GAGGGCGCCCCAGCTGGCAATTCCGACGTCTAAGAAG<br>CCATTACTATCATGACATTAACCTATAG-<br>GAATAGGCGTATCACGGGGCCCTTCCGCCTTCAC<br>CTCGGATCCCTGTCAGTGCTAGAGAT-<br>TGACATCCCTACCGGTGATAAAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAAATTTA | 143 |
| 93 | TTNNNNNGGCTTCCCAACCTTACCA-<br>GAGGGCGCCCCAGCTGGCAATTCCGACGTCTAAGAAA<br>CCATTATTATCATGACACTAAC-<br>CTATAAAAATAGGCGCATCACGAGGCCCTTTCGTCTCCAC<br>CTCAAGCCCCTATCAGTGATAGAGAT-<br>TGACATCCCCGCCGGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 144 |
| 94 | TTNNNNNGGCTTCCCAACCTTACCA-<br>GAGGGCGCCCCAGCTGGCAATTCCGACGTCTGAGAGG<br>CCATTATTATCGTGGCATTGGC-<br>CTATAAAGGCAGGCGTGTCACGAGACCCTCTCGTCTCCGC<br>CTCGGGTCCCTATCAATGGTAGAGAT-<br>TGACATCCCCATCAGTGGTGGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAAATTTA | 145 |
| 95 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT | 146 |

TABLE 2-continued

Promoters

| Promoter No, | Promoter Sequence | SEQ ID NO: |
|---|---|---|
| | CAGCAGGACGCACTGACCGAATTAT-<br>TAAAGAGGAGAAAGGTACCGCATGCGTAAAGGAGAAG<br>AACTTTTCACTGGAGTTGTCCCAATTCT-<br>TGTTGAATTAGATGGTGATGTTAATGGGCACAAA<br>TTTTCTGTCAGTGGAGAGGGTGAAGGTGATGCAACATACGGAAAACTTACCCTTAANTTTA | |
| 95 | TTTGCNGGGCTTCCCAACCTTACCA-<br>GAGGGCGCCCCAGCTGGCAATTCCGACGTCTAAGAAA<br>CCATTATTATCATGACGTTAACCTATAA-<br>GAATAGGCGTATCACGAGGCCCTTTCGTCTTCAC<br>CTCGAGTCCCTATCGGTGACAGAGAT-<br>TGACATCCCTATCAGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 147 |
| 97 | TTTGCNGGGCTTCCCAACCTTACCA-<br>GAGGGCGCCCCAGCTGGCAATTCCGACGTCTAAGGAA<br>CTATTATTATCATGACATTAAC-<br>CTATAAAAATAGGCGTATCACGAGGCCCCTTCGTCTTCAC<br>CTCGAGTCCCTATCAGTGATAGAGAT-<br>TGACATCCCTATCAGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 148 |
| 98 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGGGAT-<br>TGACATCCCTATCAGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAAATTTA | 149 |
| 99 | ATTCCGACGTCTAAGAAACCATTATTAT-<br>CATGACATTAACCTATAAAAATAGGCGTATCACG<br>AGGCCCTTTCGTCTTCACCTCGAGTC-<br>CCTATCGGTGATAGAGATTGACATCCCTATCGGTGA<br>TAGAGATACTGAGCACATC | 150 |
| 100 | TTTGCNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 151 |
| 101 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAACACGCGTATCACGAGGCCCTTTCGTCTTCAC<br>CTCGGGTCCCTATCAGTGATAGAGAT-<br>TGACATCCCTATCAGTGATAGAGACACTGAGCGCAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 152 |

TABLE 2-continued

Promoters

| Promoter No. | Promoter Sequence | SEQ ID NO: |
|---|---|---|
| 102 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTACCACGAGGCCCTTTCGTCTTCACCTCGAGTCCCTATCAGTGATAGAGAT-TGACATCCCTATCAGTGATAGAGACACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 153 |
| 103 | TTTGCNGGGCTTCCCAACCTTACCA-GAGGGCGCCCCAGCTGGCAATTCCGACGTCTGAGAAACCATTATTATCATGACATTAGC-CTATAAAAATAGGCGTATCACGGGGCCCTCTCGTCTTCACCTCAAGTCCCTACCAGTGATAGAGATA-GACATCCCTATCAGTGATAGAGACACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 154 |
| 104 | TTTGCNGGGCTTCCCAACCTTACCA-GAGGGCGCCCCAGCTGGCAATTCCGACGTCTAAGAAACCATTATTATCATGGCATTAAC-CTATAAAAATAGGCGTATCGCGAGGCCCTTTCGTCTTCACCTCGAGTCCCTATCAGTGATAGAGAT-TGACACCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 155 |
| 105 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGGTAAAGAT-TGACATCCCTATCAGTGATAGGGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGCTGAAGGT-GATGCAACATACGGAAAACTTACCCTTAAATTTA | 156 |
| 106 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTACCAGTGACAGGGAT-TGACATCCCCATCAGTGATAGAGAGACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 157 |
| 107 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 158 |

TABLE 2-continued

Promoters

| Promoter No. | Promoter Sequence | SEQ ID NO: |
|---|---|---|
| 108 | TTTGCNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTACCACGAGGCCCTTTCGTCTTCAC<br>CTCGAGTCCCTATCAGTGATAGAGAT-<br>TGACATCCCTATCAGTGATAGAGACACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 159 |
| 109 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 160 |
| 110 | TTTGCNNGGCTTCCCAACCTTACCA-<br>GAGGGCGCCCCAGCTGGCAATTCCGACGTCTAAGAAA<br>CCGTTATTATCATGACATTAGC-<br>CTATAAAAATAGGCGTATCACGAGGCCCTTCCGTCTTCAC<br>CTCGAGTCCCTATCAGTGATAGAGGT-<br>TGACACCCCTATCAGTGACAGAGATACTGAGCACAT<br>CAGCAGGACGCACTCACCGAATTCAT-<br>TAAAGAGGAGALAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 161 |
| 111 | TTTGCNNGGCTTCCCAACCTTACCA-<br>GAGGGCGCCCCAGCTGGCAATTCCGACGTCTAAGAAA<br>CCGTTATTATCATGACATTAGC-<br>CTATAAAAATAGGCGTATCACGAGGCCCTTCCGTCTTCAC<br>CTCGAGTCCCTATCAGTGATAGAGGT-<br>TGACACCCCTATCAGTGACAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 162 |
| 112 | TTTGCNNGGCTTCCCAACCTTACCA-<br>GAGGGCGCCCCAGCTGGCAATTCCGACGTCTAAGAAA<br>CCGTTATTATCATGACATTAGC-<br>CTATAAAAATAGGCGTATCACGAGGCCCTTCCGTCTTCAC<br>CTCGAGTCCCTATCAGTGATAGAGGT-<br>TGACACCCCTATCAGTGACAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 163 |
| 113 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 164 |

TABLE 2-continued

Promoters

| Promoter No. | Promoter Sequence | SEQ ID NO: |
|---|---|---|
| 114 | TTNNNNNGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAACAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 165 |
| 115 | TTNNNNNGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 166 |
| 116 | TTNNNNNGGCTTCCCAACCTTACCA-GAGGGCGCCCCAGCTGGCAATTCCGACGTCTAAGAGACCATTATTATCATGACATTGAC-CTATAAAAATAGACGTACCACGAGGCCCTTTCGTCTTCACCTCGAGTCCCTATCAGTGGTAGAGAT-TGACATCCCTATCGGTGGTAGAGATAGTGAGCACATCACCACGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 167 |
| 117 | TTNNNNNGGCTTCCCAACCTTACCA-GAGGGCGCCCCAGCTGGCAATTCCGACGTCTAAGAAACCATTATTATCATGACGTTAAC-CTATAAAAATAGGCGTATCACGAGGCCCTTTCGTCTTCACCTCGAGTCCCTATCAGTGATAGAGAT-TGACACCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 168 |
| 118 | TTNNNNGGGCTTCCCAACCTTACCA-GAGGGCGCCCCAGCTGGCAATTCCGACGTCTAAGAAACCATTATTATCATGACACTAACCTATAA-GAATAGGCGTATCACGAGGCCCTTTCGTCTTCACCTCGAGTCCCTATCAGTGATAGAGAT-TGACATCCCTATCAGTGATAGAGACACTGAGCACATCAGCACGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 169 |
| 119 | TTTGCNNGGCTTCCCAACCTTACCA-GAGGGCGCCCCAGCTGGCAATTCCGACGTCTAAGAAACCATTATTATCATGACATCAACCTATA-GAAATAGGCGTGTCACGAGGCCCTTTCGTCTTCACCTCGAGTCCCTATCAGTGGCAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAAATTTA | 170 |

TABLE 2-continued

Promoters

| Promoter No, | Promoter Sequence | SEQ ID NO: |
|---|---|---|
| 120 | TTTGCNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 171 |
| 121 | TTTGCNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGGGGCCCTTTCGTCTTCAC<br>CTCGAGTCCCTATCAGTGATAGAGGT-<br>TGACATCCCTATCAGTGATAGAAATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 172 |
| 122 | TTTGCNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGAGCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 173 |
| 123 | TTNNNANGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GACTTTTCACTGGAGTTGTCCCAATTCT-<br>TGTTGAATTAGATGGTGATGTTAATGGGCACAAA<br>ATTTTCTGTCAGTGGAGAGGGTGAAGGT-<br>GATGCAACATACGGAAAACTTACCCTTAANTTTA | 174 |
| 124 | TTNNNNGGGCTTCCCAACCTTACCA-<br>GAGGGCGCCCCAGCTGGCAATTCCGACGTCTAAGGAA<br>CCATTATTATCATGACATTAAC-<br>CTATAAAAGTAGGCGTATCACGAGGCCCTTTCGCCTTCAC<br>CTCGAGTCCCTATCAGTGATAGAGAT-<br>TGACACCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 175 |
| 125 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACACCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 176 |

TABLE 2-continued

Promoters

| Promoter No. | Promoter Sequence | SEQ ID NO: |
|---|---|---|
| 126 | CTGGCAATTCCGACGTCTAAGAAACCAT-TATTATCATGACATTAACCTATAAAAGTAGGCAT ACCATGAGGCCCTCCCGCCTTCACCTC-GAGTCCTTATCAGTGGTAGAGGTTGACGCCCCTAT CGGCGATGGAGATACTGGGCACATCAG-CAGGACGCACTGACCGAATTCATTAAAGAGGAGAA AGGTACCGCATGCGTAAAGGAGAA-GAACTTTTCACTGGAGTTGTCCCAATTCTTGTTGAATT AGATGGTGATGTTAATGGGCA-CAAATTTTCTGTCAGTGGAGAGGGtGAAGGTGATGCATCAT ACGGAAAACTTACCCTTAANTTTA | 177 |
| 127 | TTTGCNGGGCTTCCCAACCTTACCA-GAGGGCGCCCCAGCTGGCAATTCCGACGTCTAAGAAA CCATTATTATCATGACATTAAC-CTATAAAAGTAGGCGTATCACGAGGCCCTTTCGTCTTCAC CTCGGGTCCCTATCAGTGATAGAGAT-TGACGTCCCTATCAGTGATAGAGATACTGAGCACAT CAGCAGGACGCACTGACCGAATTCAT-TAAAGAGGAGAAAGGTACCGCATGCGTAAAGGAGAA GAACTTTTCACTGGAGTTGTCCCAAT-TCTTGTTGAATTAGATGGTGATGTTAATGGGCACAA ATTTTCTGTCAGTGGAGAGGGTGAAGGT-GATGCAACATACGGAAAACTTACCCTTAANTTTA | 178 |
| 128 | CTGGCAATTCCGACGTCTAAGAAACCAT-TATTATCATGACATTAACCTATAAAAACAGGCGT ATCACGAGGCCCTTCCGTCTTCACCTC-GAGTCCCTATCAGTGATAGAGATTGACATCCCTAT CAGTGATGGAGACACTGAGCACATCAG-CAGGACGCACTGACCGAATTCATTAAAGAGGAGAA AGGTACCGCATGCGTAAAGGAGAA-GAACTTTTCACTGGAGTTGTCCCAATTCTTGTTGAATT AGATGGTGATGTTAATGGGCA-CAAATTTTCTGTCAGTGGAGAGGGTGAAGGTGATGCAACAT ACGGAAAACTTACCCTTAANTTTA | 179 |
| 129 | TTTGCNNGGCTTCCCAACCTTACCA-GAGGGCGCCCCAGCTGGCAATTCCGACGTCTAAGAAA CCACTATTACCACGACATTAACCTATA-GAGATAGGCGCATCACGAGGCCCTTTCGTCTTCAC CTCGAGTCCCTATCAGTGACAGAGAT-TGACATCCCTATTAGTGATAGAGATACTGAGCACAT CAGCAGGACGCACTGACCGAATTCAT-TAAAGAGGAGAAAGGTACCGCATGCGTAAAGGAGAA GAACTTTTCACTGGAGTTGTCCCAAT-TCTTGTTGAATTAGATGGTGATGTTAATGGGCACAA ATTTTCTGTCAGTGGAGAGGGTGAAGGT-GATGCAACATACGGAAAACTTACCCTTAANTTTA | 180 |
| 130 | TTTGCNNGGCTTCCCAACCTTACCA-GAGGGCGCCCCAGCTGGCAATTCCGACGTCTAAGAAA CCATTATTATCATGACATTAAC-CTATAAAAATAGGCGTATCACGAGGCCCTTTCGTCTTCAC CTCGAGTCCCTATCAGTGATA-GAGATACTGAGCACATCAGCAGGACGCACTGACCGAATTCA TTAAAGAGGAGAAAGGTACCGCATGCG-TAAAGGAGAAGAACTTTTCACTGGAGTTGTCCCAA TTCTTGTTGAATTAGATGGTGATGT-TAATGGGCACAAATTTTCTGTCAGTGGAGAGGGTGAA GGTGATGCAACATACGGAAAACTTACCCTTAANTTTA | 181 |
| 131 | TTNNNANGGCTTCCCAACCTTACCA-GAGGGCGCCCCAGCTGGCAATTCCGACGTCTAAGAAA CCATTATTATCATGACATTAAC-CTATAAAAATAGGCGTATCACGAGGCCCTTTCGTCTTCAC CTCGAGTCCCTATCAGTGATA-GAGATACTGAGCACATCAGCAGGACGCACTGACCGAATTCA TTAAAGAGGAGAAAGGTACCGCATGCG-TAAAGGAGAAGAACTTTTCACTGGAGTTGTCCCAA TTCTTGTTGAATTAGATGGTGATGT-TAATGGGCACAAATTTTCTGTCAGTGGAGAGGGTGAA GGTGATGCAACATACGGAAAACTTACCCTTAANTTTA | 182 |
| 132 | CCCAGCTGGCAATTCCGACGTCTAA-GAAACCATTATTATCATGACATTAACCTATAAAAATA GGCGTATCACGAGGCCCTTTCGTCT-TCACCTCGAGTCCCTATCAGTGATAGAGATACTGAGC | 183 |

TABLE 2-continued

Promoters

| Promoter No, | Promoter Sequence | SEQ ID NO: |
|---|---|---|
| | ACATCAGCAGGACGCACTGACCGAAT-<br>TCATTAAAGAGGAGAAAGGTACCGCATGCGTAAAGG<br>AGAAGAACTTTTCACTGGAGTTGTC-<br>CCAATTCTTGTTGAATTAGATGGTGATGTTAATGGGC<br>ACAAATTTTCTGTCAGTGGAGAGGGT-<br>GAAGGTGATGCAACATACGGAAAACTTACCCTTAAN<br>TTTA | |
| 133 | CGCCCCAGCTGGCAATTCCGACGTCTAA-<br>GAAACCATTATTATCATGACATTAACCTATAAAA<br>ATAGGCGTATCACGAGGCCCTTTCGTCT-<br>TCACCTCGAGTCCCTATCAGTGATAGAGATACTG<br>AGCACATCAGCAGGACGCACTGAC-<br>CGAATTCATTAAAGAGGAGAAAGGTACCGCATGCGTAA<br>AGGAGAAGAACTTTTCACTGGAGTTGTC-<br>CCAATTCTTGTTGAATTAGATGGTGATGTTAATG<br>GGCACAAATTTTCTGTCAGTG-<br>GAGAGGGTGAAGGTGATGCAACATACGGAAAACTTACCCTT<br>AANTTTA | 184 |
| 134 | TGGCAATTCCGACGTCTAAGAAACCAT-<br>TATTATCATGACATTAACCTATAAAAATAGGCGTA<br>TCACGAGGCCCTTTCGTCTTCACCTC-<br>GAGTCCCTATCAGTGATAGAGATACTGAGCACATCA<br>GCAGGACGCACTGACCGAATTCATTAAA-<br>GAGGAGAAAGGTACCGCATGCGTAAAGGAGAAGA<br>ACTTTTCACTGGAGTTGTCCCAATTCT-<br>TGTTGAATTAGATGGTGATGTTAATGGGCACAAAT<br>TTTCTGTCAGTGGAGAGGGTGAAGGTGATGCAACATACGGAAAACTTACCCTTAANTTTA | 185 |
| 135 | CCCCAGCTGGCAATTCCGACGTCTAA-<br>GAAACCATTATTATCATGACATTAACCTATAAAAAT<br>AGGCGTATCACGAGGCCCTTTCGTCT-<br>TCACCTCGAGTCCCTATCAGTCATAGAGATACTGAG<br>CACATCAGCAGGACGCACTGACCGAAT-<br>TCATTAAAGAGGAGAAAGGTACCCCATGCGTAAAG<br>GAGAAGAACTTTTCACTGGAGTTGTC-<br>CCAATTCTTGTTGAATTAGATGGTGATGTTAATGGG<br>CACAAATTTTCTGTCAGTGGAGAGGGT-<br>GAAGGTGATGCAACATACGGAAAACTTACCCTTAA<br>NTTTA | 186 |
| 136 | TTCCGACGTCTAAGAAACCATTATTAT-<br>CATGACATTAACCTATAAAAATAGGCGTATCACGA<br>GGCCCTTTCGTCTTCACCTCGAGTC-<br>CCTATCAGTGATAGAGATACTGAGCACATCAGCAGGA<br>CGCACTGACCGAATTCATTAAAGAG-<br>GAGAAAGGTACCGCATGCGTAAAGGAGAAGAACTTTT<br>CACTGGAGTTGTCCCAATTCTTGT-<br>TGAATTAGATGGTGATGTTAATGGGCACAAATTTTCTG<br>TCAGTGGAGAGGGTGAAGGTGATGCAACATACGGAAAACTTACCCTTAANTTTA | 187 |
| 137 | TTNNNANGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATA-<br>GAGATACTGAGCACATCAGCAGGACGCACTGACCGAATTCA<br>TTAAAGAGGAGAAAGGTACCGCATGCG-<br>TAAAGGAGAAGAACTTTTCACTGGAGTTGTCCCAA<br>TTCTTGTTGAATTAGATGGTGATGT-<br>TAATGGGCACAAATTTTCTGTCAGTGGAGAGGGTGAA<br>GGTGATGCAACATACGGAAAACTTACCCTTAANTTTA | 188 |
| 138 | CCCAGCTGGCAATTCCGACGTCTAA-<br>GAAACCATTATTATCATGACATTAACCTATAAAATA<br>GGCGTATCACGAGGCCCTTTCGTCT-<br>TCACCTCGAGTCCCTATCAGTGATAGAGATACTGAGC<br>ACATCAGCAGGACGCACTGACCGAAT-<br>TCATTAAAGAGGAGAAAGGTACCGCATGCGTAAAGG<br>AGAAGAACTTTTCACTGGAGTTGTC-<br>CCAATTCTTGTTGAATTAGATGGTGATGTTAATGGGC<br>ACAAATTTTCTGTCAGTGGAGAGGGT-<br>GAAGGTGATGCAACATACGGAAAACTTACCCTTAAN<br>TTTA | 189 |

TABLE 2-continued

Promoters

| Promoter No. | Promoter Sequence | SEQ ID NO: |
|---|---|---|
| 139 | TTTGCNGGGCTTCCCAACCTTACCA-GAGGGCGCCCCAGCTGGCAATTCCGACGTCTAAGAAACCATTATTATCATGACATTAACCTGTA-GAAGTAGGCGTATCACGAGGCCCTTTCGCCTTCACCTCGAGTCCCTATTAGTGATAGAGGT-TGACACCCCTATCAGTGGTAGGGATACTGAGCGCATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTCAAGGT-CATGCAACATACGGAAAACTTACCCTTAANTTTA | 190 |
| 140 | TTTGCNNGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 191 |
| 141 | TTTGCNGGGCTTCCCAACCTTACCAGAG-GCCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 192 |
| 142 | TTNNNTTNNNANGGCTTCCCAACCTTAC-CACAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATA-GAGATTGACATCCCTATCAGTGATAGAGATACTGAGCACATCAGCAGGACGCACTGACCGAAT-TCATTAAAGAGGAGAAAGGTACCGCATGCGTAAAGGAGAAGAACTTTTCACTGGAGTTGTC-CCAATTCTTGTTGAATTAGATGGTGATGTTAATGGGCACAAATTTTCTGTCAGTGGAGAGGGT-GAAGGTGATGCAACATACGGAAAACTTACCCTTAANTTTA | 193 |
| 143 | TTTGCNNGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 194 |
| 144 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 195 |

TABLE 2-continued

Promoters

| Promoter No. | Promoter Sequence | SEQ ID NO: |
|---|---|---|
| 145 | TTNNNNNGGCTTCCCAACCTTACCA-GAGGGCGCCCCAGCTGGCAATTCCGACGTCTAAGAAACCATTATTATCATGACATTAAC-CTATAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 196 |
| 146 | TTNNNNNGGCTTCCCAACCTTACCA-GAGGGCGCCCCAGCTGGCAATTCCGACGTCTAAGAAACCATTATTATCATGACATTAAC-CTATAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 197 |
| 147 | TTTNNNNGGCTTCCCAACCTTACCA-GAGGGCGCCCCAGCTGGCAATTCCGACGTCTAAGAAACCACCATTATCATGACATTAACCTATA-GAAGTAGGCGTATCACGAGGCCCTTTCGTCTTCACCTCGAGTCCCTATTAGTGATAGAGAT-TGACACCCTACCAGTGGTAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAAATTTA | 198 |
| 148 | TTNNNNNGGCTTCCCAACCTTACCA-GAGGGCGCCCCAGCTGGCAATTCCGACGTCTAAGGGATCATTATTACCATGACATTAAC-CTATAAAGATAGGCGTATCACGAGGCCCTTTCGTCTTCACCTCGAGTCCCTATCAGTGATAGAGAT-TGACATCCCTATCAGTGATAGAGACACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 199 |
| 149 | TTTGCNGGGCTTCCCAACCTTACCA-GAGGGCGCCCCAGCTGGCAATTCCGACGTCTAAGAAACCATTATTATCATGACATTAAC-CTATAAAATAGGCGTATCACGAGGCCCTCTCGTCTTCACCCCGAGTCCCTATCAGTGATGGAGAT-TGACACCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 200 |
| 150 | TTTGCNGGGCTTCCCAACCTTACCA-GAGGGCGCCCCAGCTGGCAATTCCGACGTCTAAGAAACCATTATTATCATGACATTAAC-CTATAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 201 |

TABLE 2-continued

Promoters

| Promoter No. | Promoter Sequence | SEQ ID NO: |
|---|---|---|
| 151 | TTNNNNNGGCTTCCCAACCTTACCA-GAGGGCGCCCCAGCTGGCAATTCCGACGTCTAAGAAACCGTTATTATCATGACATTAAC-CTATAAAATAGGCGTATCACGAGGCCCTTTCGTCTTCACCTCGAGTCCCTATCAGTGATAGAGAT-TGACATCCCTATCAGTGATAGAGACACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 202 |
| 152 | TTNNNNGGGCTTCCCAACCTTACCA-GAGGGCGCCCCAGCTGGCAATTCCGACGTCTAAGAAACCATTATTATCATGACATTAAC-CTATAAAATAGGCGTATCACGAGGCCCTTTCGTCTTCACCTCGAGTCCCTATCAGTGATAGAGAT-TCACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 203 |
| 153 | TTNNNNNGGCTTCCCAACCTTACCA-GAGGGCGCCCCAGCTGGCAATTCCGACGTCTAAGAAACCATTATTATCATGACATTAACCTATA-GAAATAGGCGTATCACGAGGCCCCTTCGTCTTCACCTCGAGCCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 204 |
| 154 | TTNNNNNGGCTTCCCAACCTTACCA-GAGGGCGCCCCAGCTGGCAATTCCGACGTCTAAGGGACCATTATTACCATAGCATTAGC-CTATAAAGATAGGCGCACCACGGGGCCCTTTCGCCTTCACCCCGGGTCCCTATCAACGACAGAGAT-TGACACCCCTATCAGTGATAGAGATACTGGGCGCATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 205 |
| 155 | TTNNNNNGGCTTCCCAACCTTACCA-GAGGGCGCCCCAGCTGGCAATTCCGACGTCTAAGAAACCATTATTATCATGACATTAAC-CTATAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 206 |
| 156 | TTNNNNNGGCTTCCCAACCTTACCA-GAGGGCGCCCCAGCTGGCAATTCCGACGTCTAAGAAACCATTATTATCATGACATTAAC-CTATAAAATAGGCGTATCACGAGGCCCTTTCGTCTTCACCTCGAGTCCCTATCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 207 |

TABLE 2-continued

Promoters

| Promoter No. | Promoter Sequence | SEQ ID NO: |
|---|---|---|
| 157 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 208 |
| 158 | TTTGCNGGGCTTCCCAACCTTACCA-<br>GAGGGCGCCCCAGCTGGCAATTCCGACGTCTGAGAAA<br>CCATTACTGTCATGACATTAACCTACAA-<br>GAATAGGCGTATCACGAGGCCCCTTCGTCCTCAC<br>CTCGAGTCCCTATCAGTGATAGAGAT-<br>TGACATCCCTACCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 209 |
| 159 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 210 |
| 160 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 211 |
| 161 | CATCGTCGCAGCGAGTCCCTGTCAAT-<br>GATCGAGATTGACATCCCGGTCAGTCAGCCTGCGCC<br>TCAGCCCATCGCCAGGAATGCCATACCGACAGAATTAAAGTCCGGAAAGGTACCGCAT | 212 |
| 162 | TTNNNANGGCTTCCCAACCTTACCA-<br>GAGGGCGCCCCAGCTGGCAATTCCGACGTCTAAGGAA<br>CCATTATTATCATGGCATTAACCTATA-<br>GAAGTAGGCGTATCACGAGGCCCTTTCGTCTTCAC<br>CTCGAGTCCCTATCAGTGATAGAGGT-<br>TGACGTCCCTATCAGCGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 213 |
| 163 | TTTGCNGGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGGTAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA | 214 |

TABLE 2-continued

Promoters

| Promoter No, | Promoter Sequence | SEQ ID NO: |
|---|---|---|
| | GAACTTTTCACTGGAGTTGTCCCAAT-<br>TCTTGTTGAATTAGATGGTGATGTTAATCGGCACAA<br>ATTTTCTGTCAGTGGAGAGGGTGAAGGT-<br>GATGCAACATACGGAAAACTTACCCTTAANTTTA | |
| 164 | TTNNNNNGGCTTCCCAACCTTACCA-<br>GAGGGCGCCCCAGCTGGCAATTCCGACGTCTAAGAAA<br>TCATTATTATCATGACATTAACCTATA-<br>GAAATAGGCGTATCACGAGGCCCTTTCGTCCTCAC<br>CTCGAGTCCCTATCAGTGATAGAGAT-<br>TGACATCCCTATCAGTGGTAGAGATACTGAGCACAT<br>CAGCAGGACCCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 215 |
| 165 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGACAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 216 |
| 166 | TTTGCNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTAT-<br>TAAAGAGGAGAAAGGTACCGCATGCGTAAAGGAGAAG<br>AACTTTTCACTGGAGTTGTCCCAATTCT-<br>TGTTGAATTAGATGGTGATGTTAATGGGCACAAA<br>TTTTCTGTCAGTGGAGAGGGTGAAGGTGATGCAACATACGGAAAACTTACCCTTAANTTTA | 217 |
| 167 | TTNNNNNGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 218 |
| 168 | TTNNNANGGCTTCCCAACCTTACCA-<br>GAGGGCGCCCCAGCTGGCAATTCCGACGTCTAAGAAA<br>CCATTATTATCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAACGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 219 |
| 169 | TTTGCNNGGCTTCCCAACCTTACCA-<br>GAGGGCGCCCCAGCTGGCAATTCCGACGTCTAAGGAA<br>CCATTATTATCGTGACATTAAC-<br>CTATAAAAATAGGCGTATCACGAGGCCCTTTCGCCTCCAC<br>CTCGAGTCCCTACCAGTGATAGGGAT-<br>TGACATCCCTATCAGTGATAGAAATACTGAGCACAT<br>CAGCAGGACGCACTGACCGAATTCAT-<br>TAAAGAGGAGAAAGGTACCGCATGCGTAAAGGAGAA | 220 |

TABLE 2-continued

Promoters

| Promoter No. | Promoter Sequence | SEQ ID NO: |
|---|---|---|
| | GAACTTTTCACTGGAGTTGTCCCAAT-TCTTGTTGAATTAGATGGTGATGTTAATGGGCACAAATTTTCTGTCAGTGGAGAGGGTGAAGGT-CATGCAACATACGGAAAACTTACCCTTAANTTTA | |
| 170 | TTNNNNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGGTAGAGATACTGAGCACATCAGCAGGACGCACTGACCGAATTCAT-TAAAGAGGAGAAAGGTACCGCATCCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 221 |
| 171 | TTNNNNGGGCTTCCCAACCTTACCA-GAGGGCGCCCCAGCTGGCAATTCCGACGTCTAAGAAACCACTATTATCATGACATTAACCTATAA-GAGTAGGCGTATCACGAGGCCCTTTCGTCTTCACCTCGAGTCCCTGTCAGTGATAGAGAT-TGACATCCCTATCAGTGATAGAGATACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 222 |
| 172 | TTTGCNGGGCTTCCCAACCTTACCA-CAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATA-GAGATACTGAGCACATCAGCAGGACGCACTGACCGAATTCATTAAAGAGGAGAAAGGTACCGCATGCG-TAAAGGAGAAGAACTTTTCACTGGAGTTGTCCCAATTCTTGTTGAATTAGATGGTGATGT-TAATGGGCACAAATTTTCTGTCAGTGGAGAGGGTGAAGGTGATGCAACATACGGAAAACTTACCCTTAANTTTA | 223 |
| 173 | TTTGCNGGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAGACACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 224 |
| 174 | TTNNNNGGCTTCCCAACCTTACCA-GAGGGCGCCCCAGCTGGCAATTCCGACGTCTAAGAAACCATTATTATCATGACATTAAC-CTATAAAAATAGGCGTATCACGAGGCCCTTTCGTTTTCACCTCGAGTCCCCATCAGTGACAGAGAT-TGACATCCCTATCAGTGATAGAGACACTGAGCACATCAGCAGGACGCACTGACCGAATTCAT-TAAAGAGGAGAAAGGTACCGCATGCGTAAAGGAGAAGAACTTTTCACTGGAGTTGTCCCAAT-TCTTGTTGAATTAGATGGTGATGTTAATGGGCACAAATTTTCTGTCAGTGGAGAGGGTGAAGGT-GATGCAACATACGGAAAACTTACCCTTAANTTTA | 225 |
| 175 | TTTGCNGGGCTTCCCAACCTTACCA-GAGGGCGCCCCAGCTGGCAATTCCGACGTCTAAGGGACCATTATTATCATGACATTAAC-CTATAAAAATAGGCGTATCACGAGGCCCTTTCGTCTTCACCTCGAGTCCCTATCAGTGATAGAGAT-TGACATCCCTATCAGTGATAGAAATACTGAGCACATCAGCAGGACGCACTGACCGAATTCAT-TAAAGAGGAGAAAGGTACCGCATGCGTAAAGGAGAA | 226 |

TABLE 2-continued

Promoters

| Promoter No, | Promoter Sequence | SEQ ID NO: |
|---|---|---|
| | GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | |
| 176 | TTNNNNNGGCTTCCCAACCTTACCA-<br>GAGGGCGCCCCAGCTGGCAATTCCGACGTCTAAGAAA<br>CCATTATCATCATGACATTAAC-<br>CTATAAAAATAGGCGTATCACGAGGCCCTTTCGTCTTCAC<br>CTCGAGTCCCTATCAGTGACAGAGAT-<br>TGACATCCCTATCAGTGGTAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 227 |
| 177 | TTNNNNNGGCTTCCCAACCTTACCA-<br>GAGGGCGCCCCAGCTGGCAATTCCGACGTCTGAGAAA<br>CCATTATTATCATAACATTAAC-<br>CTATAAAGATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAT<br>ATTTTCTGTCAGTGGAGAGGGTGAAGGT-<br>GATGCAACATACGGAAAACTTACCCTTAAATTTA | 228 |
| 178 | TTTGCNGGGCTTCCCAACCTTACCA-<br>GAGGGCGCCCCAGCTGGCAATTCCGACGTCTAAGGAA<br>CCATTATTGTCATGACATTAAC-<br>CTATAAAAATAGGCGTATCACGAGGCCCTTTCGTCTTCAC<br>CTCGAGTCCCTATCAGTGATAGAGAT-<br>TGACATCCCTATCAGTGATAGAGATACTGAGCACAT<br>CAGCAGGACGCACTGACCGAATTCAT-<br>TAAAGAGGAGAAAGGTACCGCATGCGTAAAGGAGAA<br>GAACTTTTCACTGGAGTTGTCCCAAT-<br>TCTTGTTGAATTAGATGGTGATGTTAATGGGCACAA<br>ATTTTCTGTCAGTGGAGAGGGTGAAGGT-<br>GATGCAACATACGGAAAACTTACCCTTAANTTTA | 229 |

Example 2

Transcriptional Control of Genetic Effects on a Cellular Phenotype

To investigate whether the promoter library allowed for precise transcriptional control of specific genetic effects on a cellular phenotype, chromosomal promoter delivery into the region upstream of a targeted gene was investigated. In this case, the native promoter was replaced with one from the library, and thereby the inherent regulation modality was changed. This method facilitated assessment of genetic control due to its (a) accuracy, resulting from the comparison to a null expression level (i.e. gene knockout), and, (b) quantitative nature derived from the average promoter strength metric defined above for the library members. Furthermore, the use of an integrated system allowed the bypass of any instabilities and inherent mutation rates associated with the over-expression of endogenous genes using plasmid-based systems.

Figure 5A:
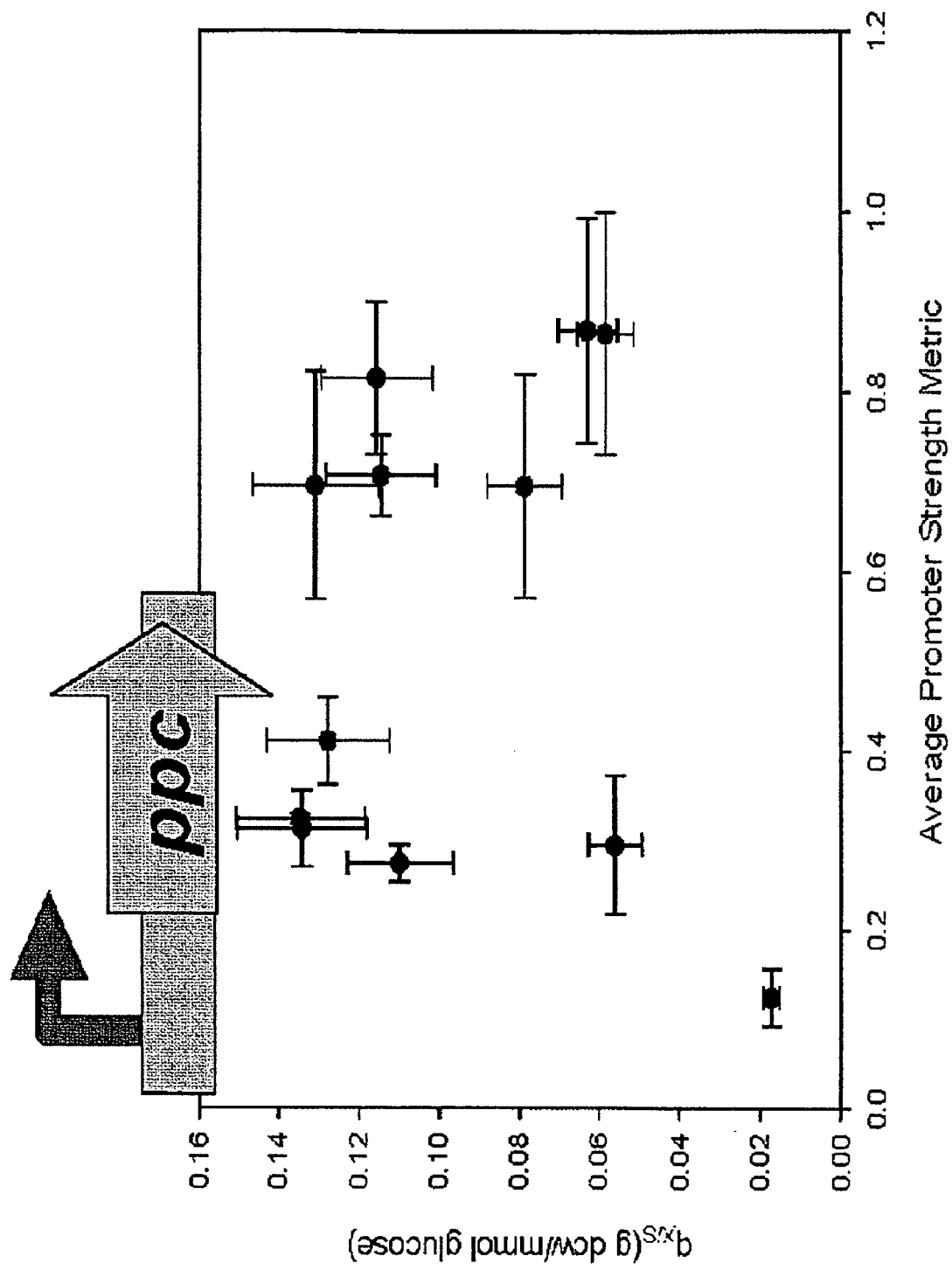
FIG. 5 demonstrates implementation of the promoter library for introducing genetic control. The phenotypes associated with integrating the promoters into the chromosome were tested using three genes. (A) Selected promoters were integrated into the promoter region of ppc and strains were cultured in M9-minimal media with only glucose as the carbon source. While the knockout of ppc is lethal in glucose media, there is a clear maximum yield from glucose and thus an optimal expression level of ppc. (B) Selected promoters were integrated in front of the dxs gene in a recombinant wild-type strain of E. coli and strains were later assayed for the production of lycopene. A clear maximum in lycopene production was obtained. From the wild-type production level, the native dxs promoter strength can be inferred to be around 0.26 according to our metric. (C) Selected promoters were integrated in front of the dxs gene in a recombinant strain also overexpressing ispFD and idi. In this case, the linear response of lycopene yield to the promoter strength illustrates a rate limiting behavior of dxs across all tested promoter strengths.

The utility of the promoter library was tested by investigating the effect of two endogenous genes (ppc and dxs) on two divergent phenotypes, namely, growth yield and lycopene production. First, we investigated the growth yield from glucose as a function of the expression level of the ppc gene in Escherichia coli. This gene expresses phosphoenol pyruvate carboxylase, a key anaplerotic enzyme. A ppc knockout is lethal for E. coli in glucose minimal medium. Furthermore, overexpression of this gene has been shown to improve the growth yield on glucose. To fully characterize the growth yield from glucose as a function of the expression level of the ppc gene, varying-strength promoter-ppc constructs were cultured while biomass and glucose concentrations were periodically monitored. FIG. 5A presents the exponential-phase biomass yields as a function of the average promoter strength metric. It is evident that increasing ppc levels have a positive effect on the biomass yield only to a certain point. This increase reaches a plateau, and further increases in the ppc level have a negative effect on the biomass yield. This decrease can be attributed to the burden of large expression of ppc or the creation of a futile cycle in metabolism. Nevertheless, these results illustrate an optimum in the expression level of ppc that is above that found from endogenous expression.

Figure 5B:
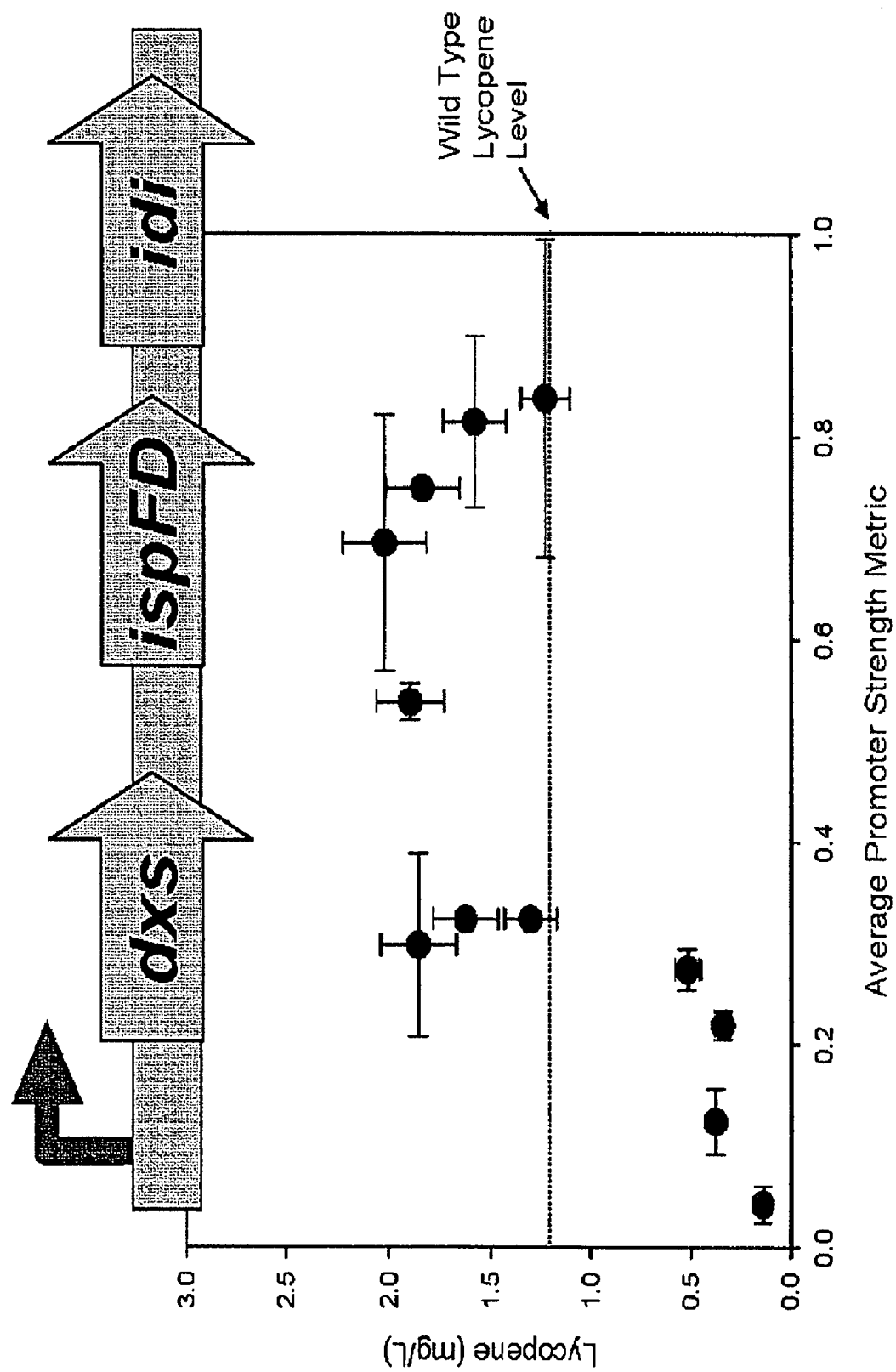

Kinetic control of metabolic pathways is often distributed and dependent on the expression level of several genes within the pathway. Promoter delivery experiments also allowed for quantification of this control. In this second case, volumetric productivity of lycopene accumulation in glucose medium was investigated as a function of the expression levels of the dxs gene in a wild-type and an engineered *E. coli* strain. The gene dxs is responsible for the condensation of glyceraldehyde-3-phosphate and pyruvate into one molecule of 1-deoxy-D-xylulose-5-phosphate (DXP), and has been implicated in controlling the flux through the isoprenoid pathway leading to lycopene. FIG. 5B shows the lycopene production in these dxs constructs in a wild-type (K12) background. Elevating dxs expression increases lycopene accumulation only until a certain point. Beyond this optimum, increased dxs expression is detrimental for lycopene production, presumably due to the inadequate activity of downstream enzymes in the isoprenoid pathway and resulting toxic buildup of DXP. The strength of the native dxs promoter can be inferred from this analysis as is illustrated on the graph.

Figure 5C:
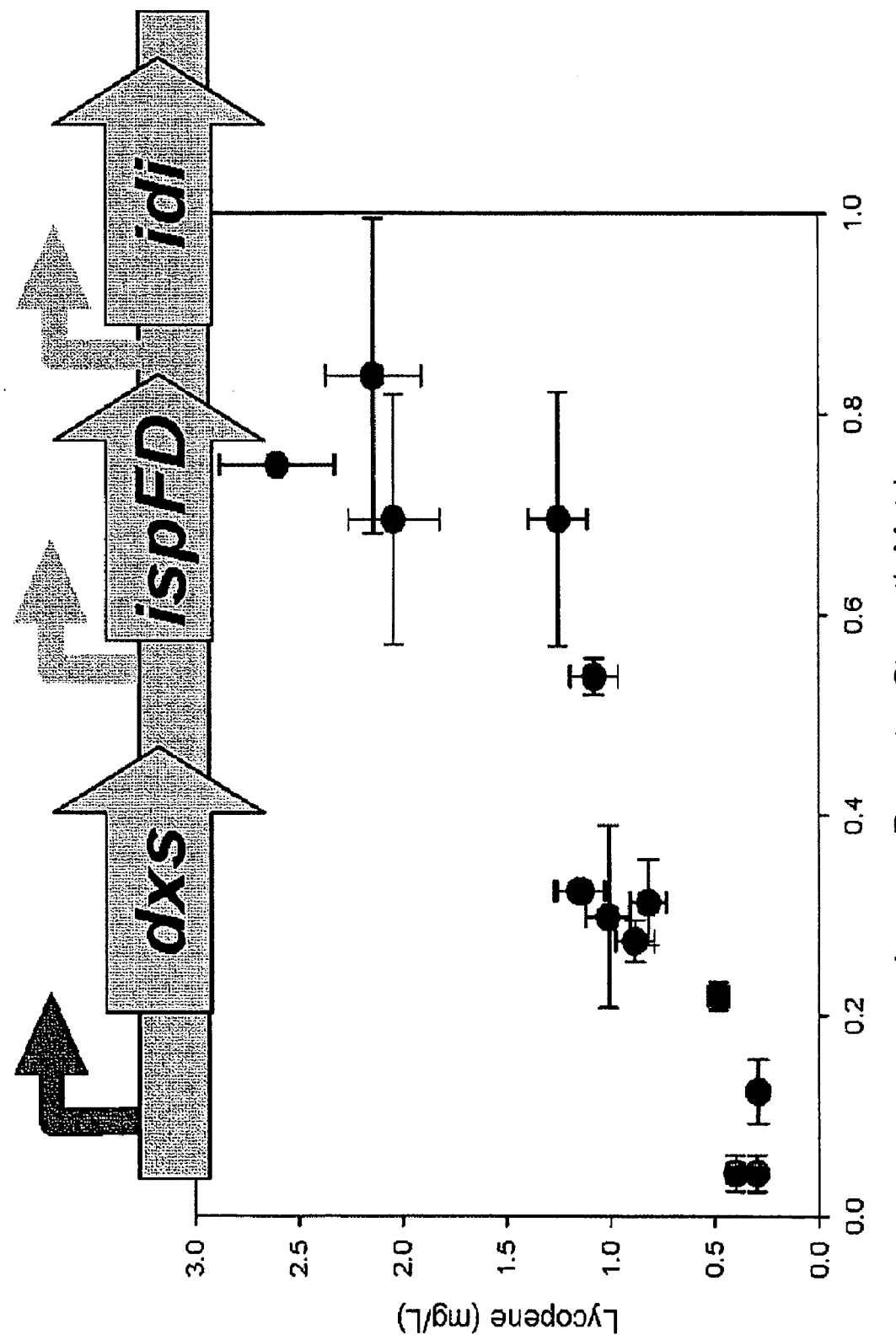

A linear relationship was obtained, however, when similar promoter-dxs constructs were placed in an engineered strain overexpressing downstream genes in the isoprenoid pathway (ispFD and idi). FIG. 5C illustrates a nearly linear response of lycopene production to varying levels of controlled dxs expression, suggesting that in the new genetic background, dxs has become rate-limiting. A linear response to an enzyme concentration is expected for rate-controlling genes exhibiting a high flux control coefficient for a given pathway. Furthermore, we note that cell density in both strains was greatly reduced in the constructs harboring low strength promoters, which was expected, as dxs is an essential gene. This quantitative evaluation of genetic control was possible due to the comprehensive characterization of the promoter strength of all library members.

Example 3

Engineered Promoters Control Gene Expression in Multiple Organisms

Figure 6:
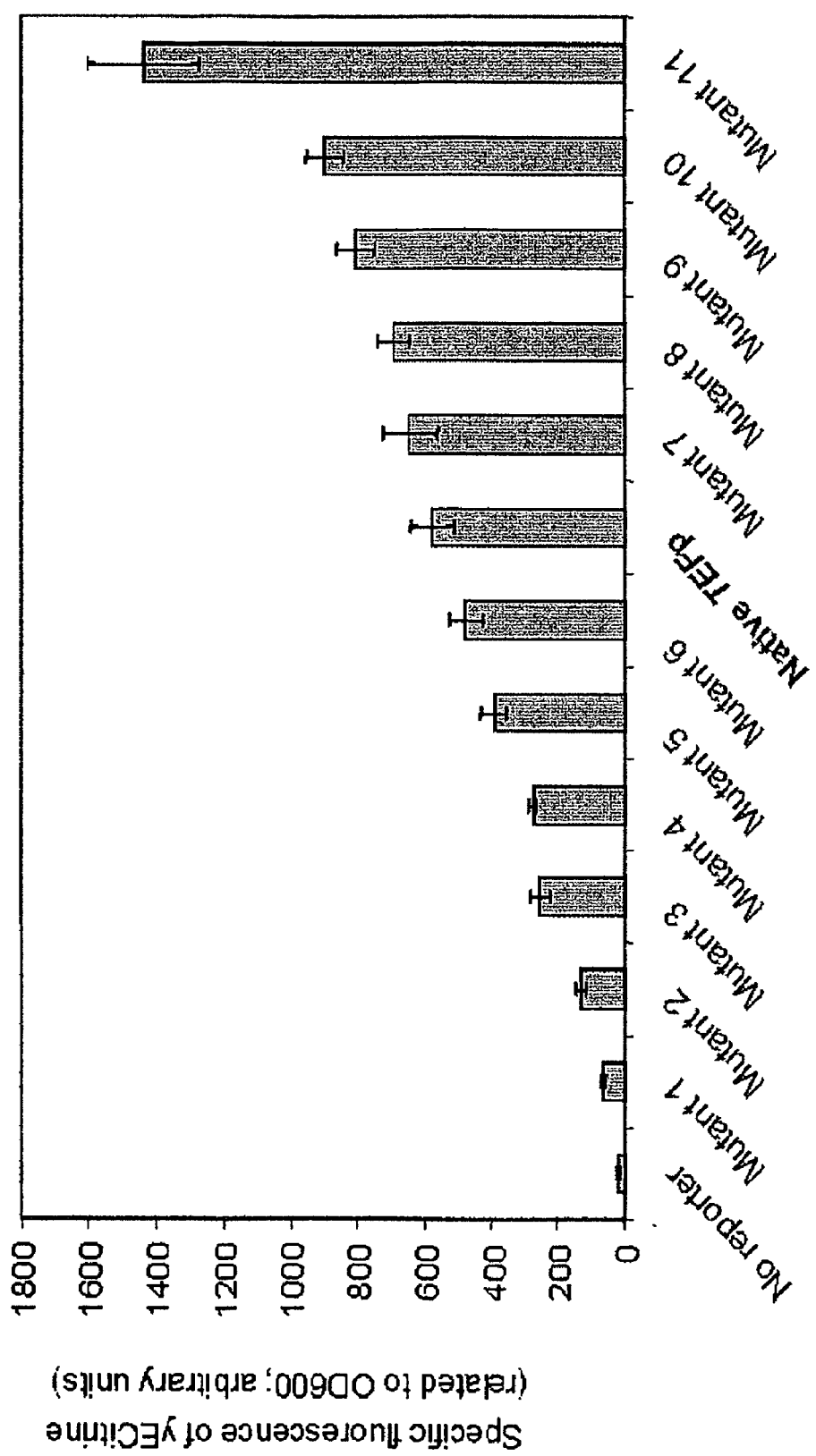
FIG. 6 demonstrates the extension of promoter engineering to other systems. The basic concepts in this paper are further extended to a eukaryotic system (S. cerevisiae) using the TEF1 promoter. A similar wide range of yECitrine fluorescence is obtained from selected clones of the original promoter library. These results along with other current work indicate the ability to select for promoters responsible for tuning precise genetic control.

The described procedure for engineering promoters to finely tune gene expression is generalizable to other organisms. By screening a library of TEF1 promoter mutants, also created by error-prone PCR, a promoter collection was obtained which drove a wide dynamic range of YFP production in *Saccharomyces cerevisiae* (FIG. 6). Thus, the promoter engineering paradigm can yield libraries of promoters for precise genetic control despite the profound differences in bacterial and eukaryotic transcription mechanisms.

It is also possible to create libraries of conditional promoters, active only under specified conditions. The selection methodology to create conditional genetic control elements which are conditionally responsive to environmental perturbations (e.g. oxygen level) included (data not shown).

The Examples hereinabove provide a general framework for the precise, quantitative control of gene expression in vivo. The strategy employed allowed (1) achievement of any desired expression level for a specific gene, (2) optimization of gene expression for maximal (or minimal) pathway function, and (3) a means for the analysis of the distribution of genetic control on pathway behavior. In two disparate examples pathway function was shown to exhibit well-defined extrema with respect to levels of gene expression. The existence of these extrema evinces the need for precise gene-dosage studies for the full understanding of pathway behavior. The creation and detailed characterization of a promoter library as described here is a facile and robust means to such an end.

What is claimed is:

1. An isolated nucleic acid comprising a mutated $PL_{teto-1}$ promoter, wherein said mutated $PL_{teto-1}$ promoter has a sequence comprising SEQ ID NO:34 with a mutation selected from the group consisting of:
   a) a replacement of a T with a C at nucleotide position 12, 38, 39, 46, 52, 58, 60, 72, 73, 76, 79, 89, 99, 102, 108, 109, 114, 118, 120, 121, 127, or 133;
   b) a replacement of an A with G at nucleotide position 12, 15, 16, 18, 19, 20, 26, 32, 35, 37, 39, 40, 41, 48, 49, 50, 51, 53, 59, 65, 81, 87, 94, 97, 101, 105, 107, 119, 122, 126, 128, 130 or 138;
   c) a replacement of a C with A at nucleotide position 21;
   d) a replacement of an A with C at nucleotide position 23, 62, 87, 101, 105, 113, 126, or 128;
   e) a replacement of a T with A at nucleotide position 24;
   f) a replacement of a C with T at nucleotide position 31 or 135;
   g) a replacement of an A with T at nucleotide position 49, 51, 62, or 87;
   h) a replacement of a G with A at nucleotide position 64, 67, 86, 98, 100, 125, 129 or 131;
   i) a replacement of a T with G at nucleotide 109;
   j) a deletion of T at nucleotide position 24;
   k) a deletion of T at nucleotide position 25;
   l) a deletion of T at nucleotide position 28;
   m) an insertion of C between nucleotide positions 88 and 89;
   n) an insertion of T between nucleotide positions 96 and 97;
   and any combination thereof.

2. A library of expression vectors, each vector comprising an isolated nucleic acid comprising:
   i. at least one gene of interest; and
   ii. a promoter operatively linked thereto;
   wherein each promoter in said library comprises a mutated $PL_{teto-1}$ promoter which is mutated with respect to that of another in said library, wherein each promoter in said library has a sequence consisting of SEQ ID NO:34 with mutations selected from the group consisting of:
a) a replacement of T with a C at nucleotide position 12, 38, 39, 46, 52, 58, 60, 72, 73, 76, 79, 89, 99, 102, 108, 109, 114, 118, 120, 121, 127, or 133;
b) a replacement of A with G at nucleotide position 12, 15, 16, 18, 19, 20, 26, 32, 35, 37, 39, 40, 41, 48, 49, 50, 51, 53, 59, 65, 81, 87, 94, 97, 101, 105, 107, 119, 122, 126, 128, 130 or 138;
c) a replacement of C with A at nucleotide position 21;
d) a replacement of A with C at nucleotide position 23, 62, 87, 101, 105, 113, 126, or 128;
e) a replacement of T with A at nucleotide position 24;
f) a replacement of C with T at nucleotide position 31 or 135;
g) a replacement of A with T at nucleotide position 49, 51, 62, or 87;
h) a replacement of G with A at nucleotide position 64, 67, 86, 98, 100, 125, 129 or 131;
i) a replacement of T with G at nucleotide position 109;
j) a deletion of T at nucleotide position 24;
k) a deletion of T at nucleotide position 25;
l) a deletion of T at nucleotide position 28;
m) an insertion of C between nucleotide positions 88 and 89;
n) an insertion of T between nucleotide positions 96 and 97;
and any combination thereof.

3. The library of claim 2, wherein said vector comprises two or more genes of interest.

4. The library of claim 2, wherein said promoter is constitutive.

5. The library of claim 2, wherein said vector is suitable for expression in a prokaryote.

6. The library of claim 2, wherein said vector is suitable for expression in a eukaryote.

7. The library of claim 2, wherein said vector comprises sequences which allow for stable integration of said promoter and said gene of interest in a genome of a cell into which said vector is introduced.

8. The library of claim 2, wherein said gene is a reporter gene.

9. The library of claim 8, wherein said reporter gene encodes a fluorescent protein.

10. The library of claim 8, wherein said reporter gene confers drug resistance.

11. The library of claim 2, wherein said at least one gene of interest encodes an enzyme.

12. The library of claim 11, wherein said enzyme is involved in a metabolic pathway.

13. The library of claim 2, wherein mutations in each promoter result in varying promoter strength.

14. The library of claim 13, wherein promoter strength may vary between 100-200-fold.

15. A plurality of cells comprising the library of claim 2.

16. The plurality of cells of claim 15, wherein each cell comprises a vector of said library, which is stably integrated within the genome of said cell.

17. The plurality of cells of claim 16, wherein said cells are prokaryotes.

18. The plurality of cells of claim 17, wherein said prokaryotes belong to the *Escherichia, Methylomonas, Methylobacter, Methylococcus, Methylosinus, Salmonella, Erwinia, Haematococcus, Rhodobacter, Myxococcus, Corynebacterium, Pseudomonas* or *Bacillus* genus.

19. The plurality of cells of claim 15, wherein said cells are eukaryotes.

20. The plurality of cells of claim 19, wherein said cells are yeast or mammalian cells.

21. The plurality of cells of claim 15, wherein said cells do not endogenously express, or have been engineered such that they do not endogenously express said at least one gene of interest.

22. The plurality of cells of claim 15 or 21, wherein said vector comprises two or more genes of interest.

23. The plurality of cells of claim 22, wherein said two or more genes of interest encode a protein involved in the carotenoid biosynthetic pathway.

24. The plurality of cells of claim 23, wherein said cells are engineered to overexpress a gene encoding a protein involved in the carotenoid biosynthetic pathway.

25. A method of determining an optimized level of gene expression for a gene of interest, the method comprising:
i. contacting a plurality of cell with the library of expression vectors of claim 1, wherein relative changes in expression level of said gene of interest are a function of the mutation in said promoter sequence;
ii. detecting said relative changes in expression level; and
iii. identifying a cell from said plurality of cells with a desired expression level,
thereby being a method of determining an optimized level of gene expression for a gene of interest.

26. The method of claim 25, wherein said detecting is accomplished utilizing quantitative polymerase chain reaction.

27. The method of claim 25, wherein said detecting is accomplished via determining enzyme activity.

28. The method of claim 25, wherein said promoter is constitutive.

29. The method of claim 25, wherein said cells do not endogenously express, or have been engineered such that they do not endogenously express said gene of interest.

30. The method of claim 25, wherein said library of expression vectors comprises sequences which allow for stable integration of said promoter and said gene of interest in the genome of said cells.

31. The method of claim 25, further comprising identifying the promoter within said cell.

32. The method of claim 25, wherein said gene is a reporter gene.

33. The method of claim 32, wherein said reporter gene encodes a fluorescent or luminescent protein.

34. The method of claim 32, wherein said reporter gene confers drug resistance.

35. The method of claim 25, wherein said gene of interest encodes an enzyme.

36. The method of claim 35, wherein said enzyme is involved in a metabolic pathway.

37. The method of claim 25, wherein said gene of interest encodes a protein involved in the carotenoid biosynthetic pathway.

38. The method of claim 37, wherein said cells are engineered to overexpress a gene encoding a protein involved in the carotenoid biosynthetic pathway.

39. The method of claim 25, wherein said library of expression vectors comprises two or more genes of interest.

40. The method of claim 39, wherein said two or more genes encode proteins which are interrelated.

41. The method of claim 39, wherein said two or more genes encode proteins involved in a metabolic pathway.

42. The method of claim 39, wherein one of said two or more genes is overexpressed.

43. The method of claim 25, wherein each said vector is suitable for expression in a prokaryote.

44. The method of claim 25, wherein said cells are prokaryotes.

45. The method of claim 44, wherein said prokaryotes belong to the *Escherichia, Methylomonas, Methylobacter, Methylococcus, Methylosinus, Salmonella, Erwinia, Haematococcus, Rhodobacter, Myxococcus, Corynebacterium Pseudomonas* or *Bacillus* genus.

46. The method of claim 25, wherein each said vector is suitable for expression in a eukaryote.

47. The method of claim 25, wherein said cells are eukaryotes.

48. The method of claim 47, wherein said cells are yeast or mammalian cells.

49. The method of claim 25, wherein each vector in said library provides a consistent level of expression of said gene of interest.

50. The method of claim 49, wherein said consistent level of expression is verified via at least two different methods.

51. The method of claim 50, wherein one of said at least two different methods verifies expression at a single cell level.

52. The method of claim 50, wherein said methods comprise fluorescent activated cell sorting analysis, fluorescence microscopy, or a combination thereof.

* * * * *

SEQUENCE LISTING

```
<160> NUMBER OF SEQ ID NOS: 231

<210> SEQ ID NO 1
<211> LENGTH: 29
<212> TYPE: DNA
<213> ORGANISM: Artificial
<220> FEATURE:
<223> OTHER INFORMATION: plasmid primer

<400> SEQUENCE: 1
ccggaattcg gtcagtgcgt cctgctgat                                       29

<210> SEQ ID NO 2
<211> LENGTH: 38
<212> TYPE: DNA
<213> ORGANISM: Artificial
<220> FEATURE:
<223> OTHER INFORMATION: plasmid primer

<400> SEQUENCE: 2
cgagttctag aaaaatgtct aaaggtgaag aattattc                             38

<210> SEQ ID NO 3
<211> LENGTH: 35
<212> TYPE: DNA
<213> ORGANISM: Artificial
<220> FEATURE:
<223> OTHER INFORMATION: plasmid primer
```

-continued

```
<400> SEQUENCE: 3
tagcgatcga tttatttgta caattcatcc atacc                                   35

<210> SEQ ID NO 4
<211> LENGTH: 20
<212> TYPE: DNA
<213> ORGANISM: Artificial
<220> FEATURE:
<223> OTHER INFORMATION: primers for GFP

<400> SEQUENCE: 4
atggctagca aaggagaaga                                                    20

<210> SEQ ID NO 5
<211> LENGTH: 20
<212> TYPE: DNA
<213> ORGANISM: Artificial
<220> FEATURE:
<223> OTHER INFORMATION: antisense primer for GFP

<400> SEQUENCE: 5
atccatgcca tgtgtaatcc                                                    20

<210> SEQ ID NO 6
<211> LENGTH: 36
<212> TYPE: DNA
<213> ORGANISM: Artificial
<220> FEATURE:
<223> OTHER INFORMATION: plasmid primer

<400> SEQUENCE: 6
cgacgcgtat ttctgccatt catccgctta ttatca                                  36

<210> SEQ ID NO 7
<211> LENGTH: 37
<212> TYPE: DNA
<213> ORGANISM: Artificial
<220> FEATURE:
<223> OTHER INFORMATION: plasmid primer

<400> SEQUENCE: 7
cggggtacct ttcaggagct aaggaagcta aaatgga                                 37

<210> SEQ ID NO 8
<211> LENGTH: 80
<212> TYPE: DNA
<213> ORGANISM: Escherichia coli

<400> SEQUENCE: 8
gtttgatagc cctgtatcct tcacgtcgca ttggcgcgaa tatgctcggc atcttccttt        60
ctcctcttta atgaattcgg                                                    80

<210> SEQ ID NO 9
<211> LENGTH: 45
<212> TYPE: DNA
<213> ORGANISM: Escherichia coli

<400> SEQUENCE: 9
gaagcagctc cagcctacac tccgacgtct aagaaaccat tatta                        45

<210> SEQ ID NO 10
<211> LENGTH: 20
<212> TYPE: DNA
<213> ORGANISM: Escherichia coli
```

```
<400> SEQUENCE: 10
gtgtaggctg gagctgcttc                                              20

<210> SEQ ID NO 11
<211> LENGTH: 70
<212> TYPE: DNA
<213> ORGANISM: Escherichia coli

<400> SEQUENCE: 11
catttccata agttacgctt atttaaagcg tcgtgaattt aatgacgtaa tccgtcgacc  60
tgcagttcga                                                         70

<210> SEQ ID NO 12
<211> LENGTH: 21
<212> TYPE: DNA
<213> ORGANISM: Escherichia coli

<400> SEQUENCE: 12
ccgatccctg gctatgaatg c                                            21

<210> SEQ ID NO 13
<211> LENGTH: 75
<212> TYPE: DNA
<213> ORGANISM: Escherichia coli

<400> SEQUENCE: 13
tgggtggagt cgaccagtgc cagggtcggg tatttggcaa tatcaaaact catcactcct  60
ctttaatgaa ttcgg                                                   75

<210> SEQ ID NO 14
<211> LENGTH: 45
<212> TYPE: DNA
<213> ORGANISM: Escherichia coli

<400> SEQUENCE: 14
gaagcagctc cagcctacac tccgacgtct aagaaaccat tatta                  45

<210> SEQ ID NO 15
<211> LENGTH: 20
<212> TYPE: DNA
<213> ORGANISM: Escherichia coli

<400> SEQUENCE: 15
gtgtaggctg gagctgcttc                                              20

<210> SEQ ID NO 16
<211> LENGTH: 76
<212> TYPE: DNA
<213> ORGANISM: Escherichia coli

<400> SEQUENCE: 16
actcgatacc tcggcactgg aagcgctagc ggactacatc atccagcgta ataaatccg   60 tcgacctgca gttcga                                                  76

<210> SEQ ID NO 17
<211> LENGTH: 21
<212> TYPE: DNA
<213> ORGANISM: Escherichia coli

<400> SEQUENCE: 17
atgagttttg atattgccaa a                                            21
```

```
<210> SEQ ID NO 18
<211> LENGTH: 19
<212> TYPE: DNA
<213> ORGANISM: Escherichia coli

<400> SEQUENCE: 18
ttatgccagc caggccttg                                              19

<210> SEQ ID NO 19
<211> LENGTH: 25
<212> TYPE: DNA
<213> ORGANISM: Escherichia coli

<400> SEQUENCE: 19
gtcagagcgt cgcgaatagc cagac                                       25

<210> SEQ ID NO 20
<211> LENGTH: 20
<212> TYPE: DNA
<213> ORGANISM: Artificial
<220> FEATURE:
<223> OTHER INFORMATION: plasmid primers

<400> SEQUENCE: 20
agatccttgg cggcaagaaa                                             20

<210> SEQ ID NO 21
<211> LENGTH: 24
<212> TYPE: DNA
<213> ORGANISM: Artificial
<220> FEATURE:
<223> OTHER INFORMATION: plasmid primers

<400> SEQUENCE: 21
gccatggaac aggtagtttt ccag                                        24

<210> SEQ ID NO 22
<211> LENGTH: 162
<212> TYPE: DNA
<213> ORGANISM: Artificial
<220> FEATURE:
<223> OTHER INFORMATION: mutant sequence of bacteriophage lambda tet0
      promoter

<400> SEQUENCE: 22
caattccgac gtctaagaaa ccattattat tatgacatta acctataaaa ataggcgtat     60
cacgaggccc ttccgtcttc acctcgagtc cctatcagtg atagagattg acatccctat    120
cagtgataga aatactgagc acatcagcag gacgcactga cc                       162

<210> SEQ ID NO 23
<211> LENGTH: 162
<212> TYPE: DNA
<213> ORGANISM: Artificial
<220> FEATURE:
<223> OTHER INFORMATION: mutant sequence of bacteriophage lambda tet0
      promoter

<400> SEQUENCE: 23
caattccgac gtctaagaag ccattattat catgacatta acctataaaa gtaggcgtgt     60
cacaaggccc tttcgtcttc acctcgagtc cctatcagcg atagagattg acatccctat    120
cagtgaccga gatactgagc acatcagcag gacgcactga cc                       162
```

```
<210> SEQ ID NO 24
<211> LENGTH: 162
<212> TYPE: DNA
<213> ORGANISM: Artificial
<220> FEATURE:
<223> OTHER INFORMATION: mutant sequence of bacteriophage lambda tetO
      promoter

<400> SEQUENCE: 24
caattccgac gtctaagaga ccattattat cgtgacatta acctataaga acaggcgtgt    60
cacgaggccc tttcgtcttc acctcgagtc cctatcagtg acagagattg acacccctat   120
cagtgataga gatactgagc acatcagcag gacgcactga cc                      162

<210> SEQ ID NO 25
<211> LENGTH: 162
<212> TYPE: DNA
<213> ORGANISM: Artificial
<220> FEATURE:
<223> OTHER INFORMATION: mutant sequence of bacteriophage lambda tetO
      promoter

<400> SEQUENCE: 25
caattccgac gcctaagaaa ccattattat catgacatta gcctataaaa ataggcgtac    60
cacgaggccc tttcgtcttc acctcgagtc cctatcagtg atagagattg acacccctat   120
cagtgataga gatactgagc acatcagcag gacgcactga cc                      162

<210> SEQ ID NO 26
<211> LENGTH: 162
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 26
caattccgac gtctaagaaa ccattgttat cgtgacatta acctataana ntaggcgtat    60
cacgaggccc tttcgccttc acctcgagtc cctatcagyg atagagaccg acacccctat   120
cagtgatagg gatactgggc acatcagcag gacgcactga cc                      162

<210> SEQ ID NO 27
<211> LENGTH: 161
<212> TYPE: DNA
<213> ORGANISM: Artificial
<220> FEATURE:
<223> OTHER INFORMATION: mutant sequence of bacteriophage lambda tetO
      promoter

<400> SEQUENCE: 27
caatccgacg tctaagaaac cattattatc atgacattaa cctataaaaa taggcgtatc    60
acgaggccct ttcgtcttca cctcgagtcc ctatcagtga tagagatgga catccctatc   120
agtgatagag atactgagca catcagcagg acgcactgac c                       161

<210> SEQ ID NO 28
<211> LENGTH: 162
<212> TYPE: DNA
<213> ORGANISM: Artificial
```

```
<220> FEATURE:
<223> OTHER INFORMATION: mutant sequence of bacteriophage lambda tetO
      promoter

<400> SEQUENCE: 28
caattccgac gtctaagaaa ccattattat catgacatta acctataaaa ataggcgtat        60
cacgaggccc tttcgtcttc acctcgagtc cctatcagtg atagagattg acctccctat       120
cagtgataga gatactgagc acatcagcag gacgcactga cc                         162

<210> SEQ ID NO 29
<211> LENGTH: 162
<212> TYPE: DNA
<213> ORGANISM: Artificial
<220> FEATURE:
<223> OTHER INFORMATION: mutant sequence of bacteriophage lambda tetO
      promoter

<400> SEQUENCE: 29
caattccgac gtctaagaaa ccattattat catgacatta acctataaaa ataggcgtat        60
cacgaggccc tctcgtcttc acctcgagtc cctatcagtg atagggattg acatccctat       120
cagtgataga gacactgggc acatcagcag gacgcactga cc                         162

<210> SEQ ID NO 30
<211> LENGTH: 162
<212> TYPE: DNA
<213> ORGANISM: Artificial
<220> FEATURE:
<223> OTHER INFORMATION: mutant sequence of bacteriophage lambda tetO
      promoter

<400> SEQUENCE: 30
caattccgac gtctaagaaa ccattgttat catgacatta acctataaaa ataggcgtat        60
cacgaggccc tttcgtcttc acctcgagtc cctatcagtg atagagattg acaccccat       120 cagtgacaga gatactgagc acatcagcag gacgcactga cc                         162

<210> SEQ ID NO 31
<211> LENGTH: 162
<212> TYPE: DNA
<213> ORGANISM: Artificial
<220> FEATURE:
<223> OTHER INFORMATION: mutant sequence of bacteriophage lambda tetO
      promoter

<400> SEQUENCE: 31
caattccgac gtctaagaaa ccattattat catgacatta acctataaaa ataggcgtat        60
cacgaggccc tttcgtcttc acctcgagtc cctatcagtg atagagattg acaccccat       120 cagtgctaga gatactgagc acatcagcag gacgcactga cc                         162

<210> SEQ ID NO 32
<211> LENGTH: 162
<212> TYPE: DNA
<213> ORGANISM: Artificial
<220> FEATURE:
<223> OTHER INFORMATION: mutant sequence of bacteriophage lambda tetO
      promoter

<400> SEQUENCE: 32
caattccgac gtctaaggaa accattatca tgacatcaac ctataaaaat aggcgtatca        60
cgaggccctc tcgtctccac ctcaagctcc ctatctagtg atagcgattg acatccctat       120
cagtgacgga gatattgagc acatcagcag gacgcactga cc                         162
```

```
<210> SEQ ID NO 33
<211> LENGTH: 162
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t

<400> SEQUENCE: 33
caattccgac gtctaggaaa ccgttatatc atgacgccga cctataaaga taggcgcgtc     60
ncgaggccct tccgccttca cctcgngctc cctatcagta atagagattg acaccctgt    120 cagtgatagg gatactgagc acatcagcag gacgcactga cc                      162

<210> SEQ ID NO 34
<211> LENGTH: 162
<212> TYPE: DNA
<213> ORGANISM: Artificial
<220> FEATURE:
<223> OTHER INFORMATION: mutant sequence of bacteriophage lambda tet0
      promoter

<400> SEQUENCE: 34
caattccgac gtctaagaaa ccattattat catgacatta acctataaaa ataggcgtat     60
cacgaggccc tttcgtcttc acctcgagtc cctatcagtg atagagattg acatccctat    120
cagtgataga gatactgagc acatcagcag gacgcactga cc                      162

<210> SEQ ID NO 35
<211> LENGTH: 162
<212> TYPE: DNA
<213> ORGANISM: Artificial
<220> FEATURE:
<223> OTHER INFORMATION: mutant sequence of bacteriophage lambda tet0
      promoter

<400> SEQUENCE: 35
caattccgac gtctaagaaa ccattattat catgacatta acctataaaa ataggcgtat     60
cacgaggccc tttcgtcttc acctcgagtc cctatcagtg atagagattg acatccctat    120
cagtgatagg gatactgagc acatcagcag gacgcactga cc                      162

<210> SEQ ID NO 36
<211> LENGTH: 162
<212> TYPE: DNA
<213> ORGANISM: Artificial
<220> FEATURE:
<223> OTHER INFORMATION: mutant sequence of bacteriophage lambda tet0
      promoter

<400> SEQUENCE: 36
caattccgac gtctgagaag ccattattat catgacatta acctataaaa gtaggcgtat     60
cacgaggccc tttcgtcttc acctcaagcc cctatcagtg atagagattg acatccctat    120
cagtgataga gacactgagc acatcagcag gacgcactga cc                      162

<210> SEQ ID NO 37
<211> LENGTH: 162
<212> TYPE: DNA
<213> ORGANISM: Artificial
```

```
<220> FEATURE:
<223> OTHER INFORMATION: mutant sequence of bacteriophage lambda tet0
      promoter

<400> SEQUENCE: 37
caattccgac gtctaagaaa ccattattat catgacatta acctataaaa ataggcgtat      60
cacgaggccc tttcgtcttc acctcgagtc cctatcagtg atagagattg acatccctat     120
cagtgataga dacactgagc acatcagcag gacgcactga cc                        162

<210> SEQ ID NO 38
<211> LENGTH: 162
<212> TYPE: DNA
<213> ORGANISM: Artificial
<220> FEATURE:
<223> OTHER INFORMATION: mutant sequence of bacteriophage lambda tet0
      promoter

<400> SEQUENCE: 38
caattccgac gtctaagaag ccattactat catgacatta acctatagga ataggcgtat      60
cacggggccc ttccgccttc acctcggatc cctgtcagtg ctagagattg acatccctac     120
cggtgataaa gatactgagc acatcagcag gacgcactga cc                        162

<210> SEQ ID NO 39
<211> LENGTH: 163
<212> TYPE: DNA
<213> ORGANISM: Artificial
<220> FEATURE:
<223> OTHER INFORMATION: mutant sequence of bacteriophage lambda tet0
      promoter

<400> SEQUENCE: 39
caattccgac gtctaagaaa ccattattat catgacacta acctataaaa ataggcgcat      60
cacgaggccc tttcgtctcc acctcaagct ccctatcagt gatagagatt gacatccccg     120
ccggtgatag agacactgag cacatcagca ggacgcactg acc                       163

<210> SEQ ID NO 40
<211> LENGTH: 162
<212> TYPE: DNA
<213> ORGANISM: Artificial
<220> FEATURE:
<223> OTHER INFORMATION: mutant sequence of bacteriophage lambda tet0
      promoter

<400> SEQUENCE: 40
caattccgac gtctgagagg ccattattat cgtggcattg gcctataaag gcaggcgtgt      60
cacgagaccc tctcgtctcc gcctcgggtc cctatcaatg gtagagattg acatccccat     120
cagtggtgga gatactgagc acatcagcag gacgcactga cc                        162

<210> SEQ ID NO 41
<211> LENGTH: 162
<212> TYPE: DNA
<213> ORGANISM: Artificial
<220> FEATURE:
<223> OTHER INFORMATION: mutant sequence of bacteriophage lambda tet0
      promoter

<400> SEQUENCE: 41
caattccgac gtctaagaaa ccattattat catgacatta acctataaaa ataggcgtat      60
cacgaggccc tttcgtcttc acctcgagtc cctatcagtg atagagattg acatccctat     120
cagtgataga gatactgagc acatcagcag gacgcactga cc                        162
```

```
<210> SEQ ID NO 42
<211> LENGTH: 162
<212> TYPE: DNA
<213> ORGANISM: Artificial
<220> FEATURE:
<223> OTHER INFORMATION: mutant sequence of bacteriophage lambda tetO
      promoter

<400> SEQUENCE: 42
caattccgac gtctaagaaa ccattattat catgacatta acctataaaa ataggcgtat      60
cacgaggccc tttcgtcttc acctcgagtc cctatcagtg atagggattg acatccctat     120
cagtgataga gacactgagc acatcagcag gacgcactga cc                        162

<210> SEQ ID NO 43
<211> LENGTH: 162
<212> TYPE: DNA
<213> ORGANISM: Artificial
<220> FEATURE:
<223> OTHER INFORMATION: mutant sequence of bacteriophage lambda tetO
      promoter

<400> SEQUENCE: 43
caattccgac gtctaagaaa ccattattat catgacatta gcctataaaa ataggcgtat      60
cacgaggccc tttcgccttc acctcgagtc cctatcggtg acagaggttg acatccctat     120
cggtgataga gatactgagc acatcagcag gacgcactga cc                        162

<210> SEQ ID NO 44
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 44
tttgcngggc ttcccaacct taccagaggg cgccccagct ggcaattccg acgtctaaga      60
aaccattatt atcatgacat taacccgcaa aaataggcgt atcacgaggc cccttcgtct     120
tcacctcgag tccctatcag tgatagaaat tgacatccct atcagcgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 45
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(5)
<223> OTHER INFORMATION: n is a, c, g, or t
```

```
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 45
ttnnnanggc ttcccaacct taccagaggg cgccccagct ggcaattccg acgtctaaga      60
aaccattatt atcatgacat taacctataa aaacaggcgt atcacgaggc cctttcgtct    120
tcacctcgag tccctatcag tgatagagat tgacatccct atcagtgata gagacactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa atttctgtc agtggagagg gtgaaggtga tgcaacatac ggaaaactta     360
cccttaantt ta                                                         372

<210> SEQ ID NO 46
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 46
tttgcngggc ttcccaacct taccagaggg cgccccagct ggcaattccg acgtctaaga     60
aaccattatt atcatgacgt taacctataa aaataggcgt atcacgaggc cctttcgtct   120
tcacctcgag tccctatcag tgatagagat tgacatccct atcagtgata gaaatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa atttctgtc agtggagagg gtgaaggtga tgcaacatac ggaaaactta    360
cccttaantt ta                                                        372

<210> SEQ ID NO 47
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 47
ttnnnnnggc ttcccaacct taccagaggg cgccccagct ggcaattccg acgtctaaga     60
aaccattatt atcatgacat taacctataa aaataggcgt atcacgaggc cctttcgtct   120
```

```
tcacctcgag tccctatcag cgatagagat tgacatccct atcagtgata gggatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                         372
```

```
<210> SEQ ID NO 48
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 48
```

```
ttnnnnnggc ttcccaacct taccagaggg cgccccagct ggcaattccg acgtctaaga     60
aaccattatt gtcatgacac taacctatga aaacaggcgt atcacgaggc cctttcgtct    120
tcgccttgag tccctatcag tgatagagat tgacatccct atcagtgata gagacactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                         372
```

```
<210> SEQ ID NO 49
<211> LENGTH: 371
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t

<400> SEQUENCE: 49
```

```
tttgcngggc ttcccaacct taccagaggg cgccccagct ggcaattccg acgtctaaga     60
aaccattatt atcatgacat taacctataa gagtaggcgt atcacgaggc cctttcgtcc    120
tcacctcgag tccctatcag tggtagagat tgacaccect atcagtgata gagatactga    180
gcacatcagc aggacgcacg accgaattca ttaaagagga gaaaggtacc gcatgcgtaa    240
aggagaagaa cttttcactg gagttgtccc aattcttgtt gaattagatg gtgatgttaa    300
tgggcacaaa ttttctgtca gtggagaggg tgaaggtgat gcaacatacg gaaaacttac    360 ccttaantt a                                                           371
```

```
<210> SEQ ID NO 50
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 50
tttnnnnggc ttcccaacct taccagaggg cgccccagct ggcaattccg acgtctgaga    60
aaccattatt atcatgacat caacctataa gaataggcgt atcacgaggc cctttcgtct   120
tcacctcgag tccctatcag tggcagagat tgacacccct atcagtgata gagatactga   180
gcacatcagc aggacgcact gaccgaattc attaaagagg agaaaggtac cgcatgcgta   240
aaggagaaga actttcact ggagttgtcc caattcttgt tgaattagat ggtgatgtta    300
atgggcacaa attttctgtc agtggagagg gtgaaggtga tgcaacatac ggaaaactta   360
cccttaantt ta                                                      372

<210> SEQ ID NO 51
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 51
tttgcngggc ttcccaacct taccagaggg cgccccagct ggcaattccg acgtctaaga    60
aaccattatt atcatgacat taacctataa agataggcgt atcacgaggc cctttcgtct   120
tcacctcgag tccctatcag tgatagagat tgacatccct atcagtgata gggatactga   180
gcacatcagc aggacgcact gaccgaattc attaaagagg agaaaggtac cgcatgcgta   240
aaggagaaga actttcact ggagttgtcc caattcttgt tgaattagat ggtgatgtta    300
atgggcacaa attttctgtc agtggagagg gtgaaggtga tgcaacatac ggaaaactta   360
cccttaantt ta                                                      372

<210> SEQ ID NO 52
<211> LENGTH: 347
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
```

```
<220> FEATURE:
<221> NAME/KEY: misc_feature
<222> LOCATION: (343)..(343)
<223> OTHER INFORMATION: n is a, c, g, or t

<400> SEQUENCE: 52
ttnnnnnggc ttcccaacct ttccagaggg cgccccagct ggcaattccg acgtctaaga      60
aaccattatt atcatgacat taacctataa aaataggcgt atcacgaggc cctttcgtct     120
tcacctcgag tccctatcag tgatagagat actgagcaca tcagcaggac gcactgaccg     180
aattcattaa agaggagaaa ggtaccgcat gcgtaaagga gaagaacttt tcactggagt     240
tgtcccaatt cttgttgaat tagatggtga tgttaatggg cacaaatttt ctgtcagtgg     300
agagggtgaa ggtgatgcaa catacggaaa acttacccct aanttta                   347

<210> SEQ ID NO 53
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t

<400> SEQUENCE: 53
tttgcngggc ttcccaacct taccagaggg cgccccagct ggcaattccg acgtctaagg      60
gatcattatt accatgacat taacctataa agataggcgt atcacgaggc cctttcgtct     120
tcacctcgag tccctatcag tgatagagat tgacatccct atcagtgata gagacactga     180
gcacatcagc aggacgcact gaccgaattc attaaagagg agaaaggtac cgcatgcgta     240
aaggagaaga actttcact ggagttgtcc caattcttgt tgaattagat ggtgatgtta     300
atgggcacaa attttctgtc agtggagagg gtgaaggtga tgcaacatac ggaaaactta     360
cccttaaatt ta                                                         372

<210> SEQ ID NO 54
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 54
tttgcngggc ttcccaacct taccagaggg cgccccagct ggcaattccg acgtctagga      60
aaccattatt atcatgacat caacctataa aaataggcgt gccacgaggc cctttcgtct     120
tcacctcggg tccctatcag tgatagagat tgacatccct accagtgata gggatactga     180
gcacatcagc aggacgcact gaccgaattc attaaagagg agaaaggtac cgcatgcgta     240
aaggagaaga actttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372
```

```
<210> SEQ ID NO 55
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 55
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 56
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 56
ttnnnnnggc ttcccaacct taccagaggg cgccccagct ggcaattccg acgtctaaga      60
aaccattatt atcatgacat taacctatga aaataggcgt atcacgaggc ccttccgtct     120
tcacctcgag tccctatcag tgatagagat tgacacccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 57
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
```

```
<220> FEATURE:
<221> NAME/KEY: misc_feature
<222> LOCATION: (368)..(368)
<223> OTHER INFORMATION: n is a, c, g, or t

<400> SEQUENCE: 57
tttgcngggc ttcccaacct taccagaggg cgccccagct ggcaattccg acgtctaaga      60
aaccattatt atcatgacat taacctatag aaacaggcgt atcgcgaggc cctttcgtct     120
tcacctcgag tccctatcag tgatagagat tgacatccct atcagtgata gaaatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                          372

<210> SEQ ID NO 58
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 58
ttnnnngggc ttcccaacct taccagaggg cgccccagct ggcaattccg acgtctagga      60
aaccattatt atcatggcat taacctataa aagtaggcgt atcacgaggc cctttcgtct     120
tcacctcgag tccctatcag tggtagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                          372

<210> SEQ ID NO 59
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 59
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
```

```
aaggagaaga acttttcact ggagttgtcc caattcttgt tgaattagat ggtgatgtta      300
atgggcacaa attttctgtc agtggagagg gtgaaggtga tgcaacatac ggaaaactta      360
cccttaantt ta                                                         372
```

<210> SEQ ID NO 60
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 60

```
tttgcnggggc ttcccaacct taccagaggg cgccccagct ggcaattccg acgtctaaga     60
aaccattatt atcatgacat taacctgtaa aaataggcgt accgcgaggc cccttcgtct      120
tcacctcggg tccctatcgg tgatagagat tgacacccct attagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 61
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 61

```
tttgcnggggc ttcccaacct taccagaggg cgccccagct ggcaattccg acgtctaaga    60
aaccactatt accatgacat taacctataa aaataggcgt atcacgaggc cctttcgtct    120
tcacctcgag tccctatcag tgatagagat tgacgcccct atcagtgata gagatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                       372
```

<210> SEQ ID NO 62
<211> LENGTH: 372
<212> TYPE: DNA
<213> ORGANISM: Artificial
<220> FEATURE:
<223> OTHER INFORMATION: mutant sequence of bacteriophage lambda tetO
      promoter

```
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 62
tttgcnnggc ttcccaacct taccagaggg cgccccagct ggcaattccg acgtctaaga    60
aaccattatt atcgtggcat taacctataa agataggcgt atcacgaggc cctttcgtct   120
tcacctcgag tccctatcag tgatagagat tgacatccct atcagtgata gagatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                       372

<210> SEQ ID NO 63
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 63
ttnnnnnggc ttcccaacct taccagaggg cgccccagct ggcaattccg acgtctaaga    60
aaccattatt atcatgacat taacctataa aaataggcgc atcacgaggc cctttcgtct   120
tcacctcgag tccctatcag tgatagagat tgacaccccct atcagtgata gagatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                       372

<210> SEQ ID NO 64
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 64 tttgcnggc ttcccaacct taccagaggg cgccccagct ggcaattccg acgtctaaga     60
aaccattatt atcatgacat taacctataa aaataggcgt atcacgaggc cctttcgtct   120
```

```
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 65
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 65
tttgcngggc ttcccaacct taccagaggg cgccccagct ggcaattccg acgtctaaga     60
aaccattatt atcatgacat taacctataa aaataggcgt atcacgaggc cctttcgtct    120
tcacctcgag tccctatcag tgatagagat tgacatccct atcggtgata gagagactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 66
<211> LENGTH: 744
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t

<400> SEQUENCE: 66
ttnnnnnggc ttcccaacct taccagaggg cgccccagct ggcaattccg acgtctaaga     60
aaccattatt atcatgacat taacctataa aaataggcgt atcacgaggc cctctcgtct    120
tcacctcgag tccctatcag tgatagagat tgacatccct atcagcgata gagacactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
```

```
atgggcacaa attttctgtc agtggagagg gtgaaggtga tgcaacatac ggaaaactta      360
cccttaantt tatttgcngg gcttcccaac cttaccagag ggcgccccag ctggcaattc      420
cgacgtctaa ggaaccatta ttatcatgac attaacctat aaaaataggc gtatcacgag      480
gccctttcgt ctccacctcg agtccctatc agtgatagag attgacgtcc ctatcagtga      540
tagagatact gagcacatca gcaggacgca ctgaccgaat tcattaaaga ggagaaaggt      600
accgcatgcg taaaggagaa gaacttttca ctggagttgt cccaattctt gttgaattag      660
atggtgatgt taatgggcac aaattttctg tcagtggaga gggtgaaggt gatgcaacat      720
acggaaaact taccccttaan ttta                                           744

<210> SEQ ID NO 67
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 67
tttgcngggc ttcccaacct taccagaggg cgccccagct ggcaattccg acgtctaaga       60
aaccattatt atcatgacat taacctgtaa aaataggcgt accacgaggc ccttcgtcc      120 ttaccccgag tccctgccag tgatagagat tgacatcccc atcagtgata gagacactga      180
gcacatcagc aggacgcact gaccgaattc attaaagagg agaaaggtac cgcatgcgta      240
aaggagaaga acttttcact ggagttgtcc caattcttgt tgaattagat ggtgatgtta      300
atgggcacaa attttctgtc agtggagagg gtgaaggtga tgcaacatac ggaaaactta      360
cccttaantt ta                                                         372

<210> SEQ ID NO 68
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 68
ttnnnnnggc ttcccaacct taccagaggg cgccccagct ggcaattccg acgtctaaga       60
aaccattatt atcatgacac taacctataa aaataggcgc atcacgaggc cctttcgtct      120
tcacctcgag tccctatcag tgatagagat tgacatccct atcagtgata gagacactga      180
gcacatcagc aggacgcact gaccgaattc attaaagagg agaaaggtac cgcatgcgta      240
aaggagaaga acttttcact ggagttgtcc caattcttgt tgaattagat ggtgatgtta      300
```

```
atgggcacaa attttctgtc agtggagagg gtgaaggtga tgcaacatac ggaaaactta    360
cccttaantt ta                                                        372
```

<210> SEQ ID NO 69
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 69

```
ttnnnngggc ttcccaacct taccagaggg cgccccagct ggcaattccg acgcctacga     60
agccattgtt atcatgacat taacctataa agacaggcgt atcacgaggc cccttcgcct    120
tcaccccggg tccctatcag tgatagagat tgacatccct atcggtgata gagacactgg    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 70
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 70

```
tttgcnngge ttcccaacct taccagaggg cgccccagct ggcaattccg acgtctaagg     60
aaccattatt atcatgacat taacctataa agtaggcat accatgaggc cctcccgcct    120
tcacctcgag tccttatcag tggtagaggt tgacgcccct atcggcgatg gagatactgg    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 71
<211> LENGTH: 372
<212> TYPE: DNA
<213> ORGANISM: Artificial
<220> FEATURE:
<223> OTHER INFORMATION: mutant sequence of bacteriophage lambda tetO
      promoter

```
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 71
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 72
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 72
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 73
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 73
tttgcngggc ttcccaacct taccagaggg cgccccagct ggcaattccg acgtctaaga      60
aaccattatt atcatgacat taacctataa aaataggcgt atcacgaggc cctttcgtct     120
```

```
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 74
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 74
ttnnnnnggc ttcccaacct taccagaggg cgccccagct ggcaattccg acgtctaaga    60
gaccattatt atcatgacat taacctataa aaataggcgt atcacgaggc cctttcgtct    120
tcacctcgag tccctatcag tggtagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 75
<211> LENGTH: 347
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 75
ttngcngggc ttcccaacct taccagaggg cgccccagct ggcaattccg acgtctaaga    60
aaccattatt atcatgacat taacctataa aaataggcgt atcacgaggc cctttcgtct    120
tcacctcgag tccctatcag tgatagagat actgagcaca tcagcaggac gcactgaccg    180
aattcattaa agaggagaaa ggtaccgcat gcgtaaagga agaactttt tcactggagt    240 tgtcccaatt cttgttgaat tagatggtga tgttaatggg cacaaatttt ctgtcagtgg    300
agagggtgaa ggtgatgcaa catacggaaa acttacccctt aaattta                 347

<210> SEQ ID NO 76
<211> LENGTH: 372
<212> TYPE: DNA
<213> ORGANISM: Artificial
```

<220> FEATURE:
<223> OTHER INFORMATION: mutant sequence of bacteriophage lambda tetO
     promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 76
ttnnnnnggc ttcccaacct taccagaggg cgccccagct ggcaattccg acgtctgaga      60
aaccattatt gtcatgacat taacctataa agataggcgt atcacgaggc cctttcgtct     120
tcacctcgag tccctatcag tgatagagat tgacatccct atcagtggta gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 77
<211> LENGTH: 372
<212> TYPE: DNA
<213> ORGANISM: Artificial
<220> FEATURE:
<223> OTHER INFORMATION: mutant sequence of bacteriophage lambda tetO
     promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 77
ttnnnnnggc ttcccaacct taccagaggg cgccccagct ggcaattccg acgtctagga      60
aaccattatt gtcatgacat taacctataa gaataggcgt atcacgaggc cctttcgtcc     120
tcaccccggg tccctatcag tgatagagat tgacatccct accagtgata aagatactgg    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 78
<211> LENGTH: 372
<212> TYPE: DNA
<213> ORGANISM: Artificial
<220> FEATURE:
<223> OTHER INFORMATION: mutant sequence of bacteriophage lambda tetO
     promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 78

```
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag cccctatcag tgatagagat tgacacccct accagtgaca gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372
```

<210> SEQ ID NO 79
<211> LENGTH: 347
<212> TYPE: DNA
<213> ORGANISM: Artificial
<220> FEATURE:
<223> OTHER INFORMATION: mutant sequence of bacteriophage lambda tetO promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 79

```
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat actgagcaca tcagcaggac gcactgaccg     180
aattcattaa agaggagaaa ggtaccgcat gcgtaaagga agaactttt cactggagt      240
tgtcccaatt cttgttgaat tagatggtga tgttaatggg cacaaatttt ctgtcagtgg     300
agagggtgaa ggtgatgcaa catacggaaa acttaccctt aanttta                   347
```

<210> SEQ ID NO 80
<211> LENGTH: 367
<212> TYPE: DNA
<213> ORGANISM: Artificial
<220> FEATURE:
<223> OTHER INFORMATION: mutant sequence of bacteriophage lambda tetO promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t

<400> SEQUENCE: 80

```
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaatta agaggagaaa ggtaccgcat gcgtaaagga     240
gaagaacttt tcactggagt tgtcccaatt cttgttgaat tagatggtga tgttaatggg     300
cacaaatttt ctgtcagtgg agagggtgaa ggtgatgcaa catacggaaa acttaccctt     360
aanttta                                                               367
```

```
<210> SEQ ID NO 81
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 81
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 82
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 82
ttnnnanggc ttcccaacct taccagaggg cgccccagct ggcaattccg acgtctaaga      60
aaccattatt atcatgacat taacctataa aaataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 83
<211> LENGTH: 372
<212> TYPE: DNA
<213> ORGANISM: Artificial
<220> FEATURE:
<223> OTHER INFORMATION: mutant sequence of bacteriophage lambda tet0
      promoter
```

```
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 83
tttgcngggc ttcccaacct taccagaggg cgccccagct ggcaattccg acgtctaaga      60
aaccattatt atcatgacat taacctacaa agataggcgt atcatggggc cctttcgtct     120
tcacctcgag tccctatcag tgatagagat tgacaccccct atcagtgaca gagatactgg    180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 84
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 84
ttnnnnnggc ttcccaacct taccagaggg cgccccagct ggcaattccg acgtctaaga      60
aaccactatt accatgacat taacctataa aaataggcgt atcacgaggc cctttcgtct     120
tcacctcgag tccctatcag tgacagagat tgacaccccct atcagtgata gagatactga    180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 85
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 85
tttgcngggc ttcccaacct taccagaggg cgccccagct ggcaattccg acgtctaaga      60
aaccattatt atcatgacat taacctataa aaataggcgt atcacgaggc cctttcgtct     120
```

```
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                       372
```

<210> SEQ ID NO 86
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 86

```
tttgcngggc ttcccaacct taccagaggg cgccccagct ggcaattccg acgtctaaga     60
aaccattatt atcatgacat taacctataa aaataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                       372
```

<210> SEQ ID NO 87
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 87

```
ttnnnnnggc ttcccaacct taccagaggg cgccccagct ggcaattccg acgtctaaga     60
aaccattatt atcatgacat tgacctacaa aagtaggcgt atcacgaggc cctttcgtct    120
tcacctcgag tccctatcag tgatagagat tgacatccct atcagtgata gaaatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                       372
```

```
<210> SEQ ID NO 88
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 88
ttnnnnnggc ttcccaacct taccagaggg cgccccagct ggcaattccg acgtctaaga      60
aaccattatt atcatgacat taacctataa aaacaggcgt atcacgaggc cctttcgtct     120
tcacctcggg tccctatcag tgatagagat tgacatccct atcagtgata gagacactga     180
gcgcatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 89
<211> LENGTH: 382
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (2)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t

<400> SEQUENCE: 89
tnnnnnnnnn tttgcngggc ttcccaacct taccagaggg cgccccagct ggcaattccg      60
acgtctaaga aaccattatt atcatgacat taacctatag aaataggcgt atcacgaggc     120
cctctcgtct ccacctcgag ccctgtcag taataggat tgacaccct accagtgata       180 gagacactga gcacatcagc aggacgcact gaccgaattc attaaagagg agaaaggtac     240
cgcatgcgta aaggagaaga acttttcact ggagttgtcc caattcttgt tgaattagat     300
ggtgatgtta atgggcacaa attttctgtc agtggagagg gtgaaggtga tgcaacatac     360
ggaaaactta cccttaantt ta                                              382

<210> SEQ ID NO 90
<211> LENGTH: 372
<212> TYPE: DNA
<213> ORGANISM: Artificial
<220> FEATURE:
<223> OTHER INFORMATION: mutant sequence of bacteriophage lambda tetO
      promoter
```

```
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 90
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                          372

<210> SEQ ID NO 91
<211> LENGTH: 120
<212> TYPE: DNA
<213> ORGANISM: Artificial
<220> FEATURE:
<223> OTHER INFORMATION: mutant sequence of bacteriophage lambda tetO
      promoter

<400> SEQUENCE: 91
cgcgtaaaga agaacagctt gtcacgcgtt ttgtgccaat tcttgatgaa cgaggcggtc      60
tggtcaatcg ggataaatgt cgcctgagtg datagggtga aggtgataca acatgccgaa    120

<210> SEQ ID NO 92
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 92
ttnnnnnggc ttcccaacct taccagaggg cgccccagct ggcaattccg acgtctaagg      60
ggccattatt atcatgacgc taacctgtga aggtaggcgt atcacgaggc ccttccgtct     120
tcgccttgag tccctattag tgatagaggt tgacgcccct atcagtggta gagatactgg     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                          372

<210> SEQ ID NO 93
<211> LENGTH: 92
<212> TYPE: DNA
<213> ORGANISM: Artificial
```

```
<220> FEATURE:
<223> OTHER INFORMATION: mutant sequence of bacteriophage lambda tetO
      promoter
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (68)..(72)
<223> OTHER INFORMATION: n is a, c, g, or t
<220> FEATURE:
<221> NAME/KEY: misc_feature
<222> LOCATION: (74)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (87)..(91)
<223> OTHER INFORMATION: n is a, c, g, or t

<400> SEQUENCE: 93
caaattttcg gtaagtggaa ggggcgtggg tgatgcaaca gcaggaaacc tgctggatag      60 ctctananann nncnnnnnnn ngnntgnnnn nt                                   92

<210> SEQ ID NO 94
<211> LENGTH: 347
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 94
tttnnngggc ttcccaacct taccagaggg cgccccagct ggcaattccg acgtctaaga      60
aaccattatt atcatgacat taacctataa aaataggcgt atcacgaggc cctttcgtct    120
tcacctcgag tccctatcag tgatagagat actgagcaca tcagcaggac gcactgaccg    180
aattcattaa agaggagaaa ggtaccgcat gcgtaaagga gaagaacttt tcactggagt    240
tgtcccaatt cttgttgaat tagatggtga tgttaatggg cacaaatttt ctgtcagtgg    300
agagggtgaa ggtgatgcaa catacggaaa acttacccct aanttta                  347

<210> SEQ ID NO 95
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
```

<400> SEQUENCE: 95

```
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                          372
```

<210> SEQ ID NO 96
<211> LENGTH: 372
<212> TYPE: DNA
<213> ORGANISM: Artificial
<220> FEATURE:
<223> OTHER INFORMATION: mutant sequence of bacteriophage lambda tetO promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 96

```
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                          372
```

<210> SEQ ID NO 97
<211> LENGTH: 372
<212> TYPE: DNA
<213> ORGANISM: Artificial
<220> FEATURE:
<223> OTHER INFORMATION: mutant sequence of bacteriophage lambda tetO promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 97

```
ttnnnanggc ttcccaacct taccagaggg cgccccagct ggcaattccg acgtctaaga      60
agccattatt atcatggcat taacctataa aaataggcgt atcacgaggc cctttcgtct     120
tcaccccgag tccctatcag tgatagagat tgacatccct atcagtgata gaggtactga     180
gcacatcagc aggacgcact gaccgaattc attaaagagg agaaaggtac cgcatgcgta     240
```

```
aaggagaaga actttcact ggagttgtcc caattcttgt tgaattagat ggtgatgtta    300
atgggcacaa attttctgtc agtggagagg gtgaaggtga tgcaacatac ggaaaactta    360
cccttaantt ta                                                       372
```

```
<210> SEQ ID NO 98
<211> LENGTH: 347
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 98
```

```
ttnnnanggc ttcccaacct taccagaggg cgccccagct ggcaattccg acgtctaaga    60
aaccattatt atcatgacat taacctataa aaataggcgt atcacgaggc cctttcgtct   120
tcacctcgag tccctatcag tgatagagat actgagcaca tcagcaggac gcactgaccg   180
aattcattaa agaggagaaa ggtaccgcat gcgtaaagga gaagaacttt tcactggagt   240
tgtcccaatt cttgttgaat tagatggtga tgttaatggg cacaaatttt ctgtcagtgg   300
agagggtgaa ggtgatgcaa catacggaaa acttacccct taantta              347
```

```
<210> SEQ ID NO 99
<211> LENGTH: 307
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (304)..(306)
<223> OTHER INFORMATION: n is a, c, g, or t

<400> SEQUENCE: 99
```

```
ttccgacgtc taagaaacca ttattatcat gacattaacc tataaaaata ggcgtatcac    60
gaggcccttt cgtcttcacc tcgagtccct atcagtgata gagatactga gcacatcagc   120
aggacgcact gaccgaattc attaaagagg agaaaggtac cgcatgcgta aaggagaaga   180
acttttcact ggagttgtcc caattcttgt tgaattagat ggtgatgtta atgggcacaa   240
attttctgtc agtggagagg gtgaaggtga tgcaacatac ggaaaactta cccttaantt   300 tatnnnc                                                              307
```

```
<210> SEQ ID NO 100
<211> LENGTH: 356
<212> TYPE: DNA
<213> ORGANISM: Artificial
<220> FEATURE:
<223> OTHER INFORMATION: mutant sequence of bacteriophage lambda tet0
      promoter
```

```
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (348)..(349)
<223> OTHER INFORMATION: n is a, c, g, or t
<220> FEATURE:
<221> NAME/KEY: misc_feature
<222> LOCATION: (351)..(355)
<223> OTHER INFORMATION: n is a, c, g, or t

<400> SEQUENCE: 100 tttgcnggc ttcccaacct taccagaggg cgccccagct ggcaattccg acgtctaaga      60
aaccattatt atcatgacat taacctataa aaataggcgt atcacgaggc cctttcgtct    120
tcacctcgag tccctatcag tgatagagat actgagcaca tcagcaggac gcactgaccg    180
aattcattaa agaggagaaa ggtaccgcat gcgtaaagga gaagaacttt tcactggagt    240
tgtcccaatt cttgttgaat tagatggtga tgttaatggg cacaaatttt ctgtcagtgg    300
agagggtgaa ggtgatgcaa catacggaaa acttacccct aantttannt nnnnna       356

<210> SEQ ID NO 101
<211> LENGTH: 347
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 101
ttnnnnnggc ttcccaacct taccagaggg cgccccagct ggcaattccg acgtctaaga     60
aaccattatt atcatgacat taacctataa aaataggcgt atcacgaggc cctttcgtct    120
tcacctcgag tccctatcag tgatagagat actgagcaca tcagcaggac gcactgaccg    180
aattcattaa agaggagaaa ggtaccgcat gcgtaaagga gaagaacttt tcactggagt    240
tgtcccaatt cttgttgaat tagatggtga tgttaatggg cacaaatttt ctgtcagtgg    300
agagggtgaa ggtgatgcaa catacggaaa acttacccct aanttta                 347

<210> SEQ ID NO 102
<211> LENGTH: 347
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
```

<400> SEQUENCE: 102

```
tttgcngggc ttcccaacct taccagaggg cgccccagct ggcaattccg acgtctaaga    60
aaccattatt atcatgacat taacctataa aaataggcgt atcacgaggc cctttcgtct   120
tcacctcgag tccctatcag tgatagagat actgagcaca tcagcaggac gcactgaccg   180
aattcattaa agaggagaaa ggtaccgcat gcgtaaagga gaagaacttt tcactggagt   240
tgtcccaatt cttgttgaat tagatggtga tgttaatggg cacaaatttt ctgtcagtgg   300
agagggtgaa ggtgatgcaa catacggaaa acttaccctt aanttta               347
```

<210> SEQ ID NO 103
<211> LENGTH: 347
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 103

```
ttnnnanggc ttcccaacct taccagaggg cgccccagct ggcaattccg acgtctaaga    60
aaccattatt atcatgacat taacctataa aaataggcgt atcacgaggc cctttcgtct   120
tcacctcgag tccctatcag tgatagagat actgagcaca tcagcaggac gcactgaccg   180
aattcattaa agaggagaaa ggtaccgcat gcgtaaagga gaagaacttt tcactggagt   240
tgtcccaatt cttgttgaat tagatggtga tgttaatggg cacaaatttt ctgtcagtgg   300
agagggtgaa ggtgatgcaa catacggaaa acttaccctt aanttta               347
```

<210> SEQ ID NO 104
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 104

```
tttgcnnggc ttcccaacct taccagaggg cgccccagct ggcaattccg acgtctaaga    60
aaccattatt atcatgacat taacctataa aaataggcgt atcacgaggc cctttcgtct   120
tcacctcgag tccctatcag tgatagagat tgacatccct atcagtgata gagatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
```

```
atgggcacaa attttctgtc agtggagagg gtgaaggtga tgcaacatac ggaaaactta        360
cccttaantt ta                                                            372
```

<210> SEQ ID NO 105
<211> LENGTH: 347
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 105

```
tttgcngggc ttcccaacct taccagaggg cgccccagct ggcaattccg acgtctaaga         60
aaccattatt atcatgacat taacctataa aaataggcgt atcacgaggc cctttcgtct        120
tcacctcgag tccctatcag tgatagagat actgagcaca tcagcaggac gcactgaccg        180
aattcattaa agaggagaaa ggtaccgcat gcgtaaagga gaagaacttt tcactggagt        240
tgtcccaatt cttgttgaat tagatggtga tgttaatggg cacaaatttt ctgtcagtgg        300
agagggtgaa ggtgatgcaa catacggaaa acttaccctt aanttta                     347
```

<210> SEQ ID NO 106
<211> LENGTH: 347
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 106

```
tttgcngggc ttcccaacct taccagaggg cgccccagct ggcaattccg acgtctaaga         60
aaccattatt atcatgacat taacctataa aaataggcgt atcacgaggc cctttcgtct        120
tcacctcgag tccctatcag tgatagagat actgagcaca tcagcaggac gcactgaccg        180
aattcattaa agaggagaaa ggtaccgcat gcgtaaagga gaagaacttt tcactggagt        240
tgtcccaatt cttgttgaat tagatggtga tgttaatggg cacaaatttt ctgtcagtgg        300
agagggtgaa ggtgatgcaa catacggaaa acttaccctt aanttta                     347
```

<210> SEQ ID NO 107
<211> LENGTH: 347
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t

```
<220> FEATURE:
<221> NAME/KEY: misc_feature
<222> LOCATION: (343)..(343)
<223> OTHER INFORMATION: n is a, c, g, or t

<400> SEQUENCE: 107
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat actgagcaca tcagcaggac gcactgaccg     180
aattcattaa agaggagaaa ggtaccgcat gcgtaaagga gaagaacttt tcactggagt     240
tgtcccaatt cttgttgaat tagatggtga tgttaatggg cacaaatttt ctgtcagtgg     300
agagggtgaa ggtgatgcaa catacggaaa acttacccct aanttta                  347

<210> SEQ ID NO 108
<211> LENGTH: 349
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t

<400> SEQUENCE: 108
antttgcnng gcttcccaac cttaccagag ggcgccccag ctggcaattc cgacgtctaa      60
gaaaccatta ttatcatgac attaacctat aaaaataggc gtatcacgag gccctttcgt    120
cttcacctcg agtccctatc agtgatagag atactgagca catcagcagg acgcactgac    180
cgaattcatt aaagaggaga aaggtaccgc atgcgtaaag gagaagaact ttcactgga     240 gttgtcccaa ttcttgttga attagatggt gatgttaatg ggcacaaatt ttctgtcagt    300
ggagagggtg aaggtgatgc aacatacgga aaacttaccc ttaanttta              349

<210> SEQ ID NO 109
<211> LENGTH: 347
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 109
ttnnnnnggc ttcccaacct taccagaggg cgccccagct ggcaattccg acgtctaaga      60
aaccattatt atcatgacat taacctataa aaataggcgt atcacgaggc cctttcgtct    120
tcacctcgag tccctatcag tgatagagat actgagcaca tcagcaggac gcactgaccg    180
aattcattaa agaggagaaa ggtaccgcat gcgtaaagga gaagaacttt tcactggagt    240
```

```
tgtcccaatt cttgttgaat tagatggtga tgttaatggg cacaaatttt ctgtcagtgg      300
agagggtgaa ggtgatgcaa catacggaaa acttacccct aanttta                   347

<210> SEQ ID NO 110
<211> LENGTH: 347
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 110
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat actgagcaca tcagcaggac gcactgaccg     180
aattcattaa agaggagaaa ggtaccgcat gcgtaaagga gaagaacttt tcactggagt     240
tgtcccaatt cttgttgaat tagatggtga tgttaatggg cacaaatttt ctgtcagtgg     300
agagggtgaa ggtgatgcaa catacggaaa acttacccct aanttta                   347

<210> SEQ ID NO 111
<211> LENGTH: 347
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 111 ttnnnnanggc ttcccaacct taccagaggg cgccccagct ggcaattccg acgtctaaga    60
aaccattatt atcatgacat taacctataa aaataggcgt atcacgaggc cctttcgtct    120
tcacctcgag tccctatcag tgatagagat actgagcaca tcagcaggac gcactgaccg    180
aattcattaa agaggagaaa ggtaccgcat gcgtaaagga gaagaacttt tcactggagt    240
tgtcccaatt cttgttgaat tagatggtga tgttaatggg cacaaatttt ctgtcagtgg    300
agagggtgaa ggtgatgcaa catacggaaa acttacccct aanttta                  347

<210> SEQ ID NO 112
<211> LENGTH: 364
<212> TYPE: DNA
<213> ORGANISM: Artificial
<220> FEATURE:
<223> OTHER INFORMATION: mutant sequence of bacteriophage lambda tetO
      promoter
```

```
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (9)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t

<400> SEQUENCE: 112
aannnnntnn nnnnnanttt gcngggcttc ccaaccttac cagagggcgc cccagctggc      60
aattccgacg tctaagaaac cattattatc atgacattaa cctataaaaa taggcgtatc     120
acgaggccct ttcgtcttca cctcgagtcc ctatcagtga tagagatact gagcacatca     180
gcaggacgca ctgaccgaat tcattaaaga ggagaaaggt accgcatgcg taaaggagaa     240
gaacttttca ctggagttgt cccaattctt gttgaattag atggtgatgt taatgggcac     300 aaatttttctg tcagtggaga gggtgaaggt gatgcaacat acggaaaact tacccttaan    360
ttta                                                                   364

<210> SEQ ID NO 113
<211> LENGTH: 379
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: misc_feature
<222> LOCATION: (6)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (363)..(365)
<223> OTHER INFORMATION: n is a, c, g, or t
<220> FEATURE:
<221> NAME/KEY: misc_feature
<222> LOCATION: (367)..(378)
<223> OTHER INFORMATION: n is a, c, g, or t

<400> SEQUENCE: 113
gnnntnnnnn nnantttgcn gggcttccca accttaccag agggcgcccc agctggcaat     60
tccgacgtct aagaaaccat tattatcatg acattaacct ataaaaatag gcgtatcacg     120 aggcccttc gtcttcacct cgagtcccta tcagtgatag agatactgag cacatcagca     180
ggacgcactg accgaattca ttaaagagga gaaaggtacc gcatgcgtaa aggagaagaa     240
```

-continued

```
cttttcactg gagttgtccc aattcttgtt gaattagatg gtgatgttaa tgggcacaaa      300
ttttctgtca gtggagaggg tgaaggtgat gcaacatacg gaaaacttac ccttaaattt      360
atnnncnnnn nnnnnnnnc                                                   379
```

<210> SEQ ID NO 114
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 114

```
tttgcnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372
```

<210> SEQ ID NO 115
<211> LENGTH: 357
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (2)..(10)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t

<400> SEQUENCE: 115

```
tnnnnnnnnn ttnnnanggc ttcccaacct taccagaggg cgccccagct ggcaattccg      60
acgtctaaga aaccattatt atcatgacat taacctataa aaataggcgt atcacgaggc     120
cctttcgtct tcacctcgag tccctatcag tgatagagat actgagcaca tcagcaggac     180
gcactgaccg aattcattaa agaggagaaa ggtaccgcat gcgtaaagga gaagaacttt     240
tcactggagt tgtcccaatt cttgttgaat tagatggtga tgttaatggg cacaaatttt     300
ctgtcagtgg agagggtgaa ggtgatgcaa catacggaaa acttacccctt aantttta     357
```

```
<210> SEQ ID NO 116
<211> LENGTH: 371
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t

<400> SEQUENCE: 116
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaatta ttaaaggagga gaaaggtacc gcatgcgtaa    240
aggagaagaa cttttcactg gagttgtccc aattcttgtt gaattagatg gtgatgttaa     300
tgggcacaaa ttttctgtca gtggagaggg tgaaggtgat gcaacatacg gaaaacttac    360
ccttaanttt a                                                         371

<210> SEQ ID NO 117
<211> LENGTH: 354
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t

<400> SEQUENCE: 117
cnnnnnantt tgcngggctt cccaaccttac cagagggcg ccccagctgg caattccgac      60
gtcaacctat aaaataggc gtatcacgag gccctctcgt cttcacctcg agtccctatc     120
agtgatagag attgacaccc ctatcagtga tagagatact gagcacatca gcaggacgca    180
ctgaccgaat tcattaaaga ggagaaaggt accgcatgcg taaaggagaa gaacttttca    240
ctggagttgt cccaattctt gttgaattag atggtgatgt taatgggcac aaattttctg    300
tcagtggaga gggtgaaggt gatgcaacat acggaaaact taccttaan ttta           354

<210> SEQ ID NO 118
<211> LENGTH: 389
<212> TYPE: DNA
<213> ORGANISM: Artificial
<220> FEATURE:
<223> OTHER INFORMATION: mutant sequence of bacteriophage lambda tet0
      promoter
```

```
<220> FEATURE:
<221> NAME/KEY: misc_feature
<222> LOCATION: (3)..(17)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t

<400> SEQUENCE: 118
aannnnnnnn nnnnnnnttt gcngggcttc ccaaccttac cagagggcgc cccagctggc      60
aattccgacg tctaagaaac cattattatc atgacattaa cctatagaaa caggcgtatc     120
acgaggccct ttcgtcttca cctcgagttc ctatcagtga tagagactga catccctatc     180
agtgatagag atactgagca catcagcagg acgcactgac cgaattcatt aaagaggaga     240
aaggtaccgc atgcgtaaag gagaagaact tttcactgga gttgtcccaa ttcttgttga     300
attagatggt gatgttaatg ggcacaaatt ttctgtcagt ggagagggtg aaggtgatgc     360
aacatacgga aaacttaccc ttaanttta                                       389

<210> SEQ ID NO 119
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 119
tttgcngggc ttcccaacct taccagaggg cgccccagct ggcaattccg acgtctaaga      60
agccattatt gtcatgacat taacctataa agataggcgt attacgaggc cctctcgtct     120
tcacctcgag tccctatcgg tgatagagat tgacatccct gtcagtggca gggatactga     180
gcacatcagc aggacgcact gaccgaattc attaaagagg agaaaggtac cgcatgcgta     240
aaggagaaga actttcact ggagttgtcc caattcttgt tgaattagat ggtgatgtta     300
atgggcacaa atttctgtc agtggagagg gtgaaggtga tgcaacatac ggaaaactta     360
cccttaantt ta                                                        372

<210> SEQ ID NO 120
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
```

```
<400> SEQUENCE: 120
ttnnnnnggc ttcccaacct taccagaggg cgccccagct ggcaattccg acgtctaaga      60
aaccattatt atcatgacat tagcctataa aaataggcgt atcacgaggc cctttcgtct     120
tcacctcgag cccctaccag tgacagaggt tgacgtccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 121
<211> LENGTH: 383
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (2)..(11)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t

<400> SEQUENCE: 121
annnnnnnnn ntttgcnggg cttcccaacc ttaccagagg gcgccccagc tggcaattcc      60
gacgtctaag aaaccattat tatcatgaca ttaacctata agataggcg tatcacgagg     120 cccttccgtc ttcacctcga gtccctatca gtgatagagg ttgacgtccc tatcagtggt     180
agagatactg agcacatcag caggacgcac tgaccgaatt cattaaagag gagaaaggta     240
ccgcatgcgt aaaggagaag aacttttcac tggagttgtc ccaattcttg ttgaattaga     300
tggtgatgtt aatgggcaca aattttctgt cagtggagag ggtgaaggtg atgcaacata     360
cggaaaactt acccttaant tta                                             383

<210> SEQ ID NO 122
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 122
tttgcngggc ttcccaacct taccagaggg cgccccagct ggcaattccg acgtctaagg      60
ggtcattatt atcatgacgc taacctgtga aggtaggcgt atcacgaggc ccttccgtct     120 tcgcctgag tccctattag tgatagaggt tgacgcccct atcagtggta gagatactgg     180
gcacatcagc aggacgcact gaccgaattc attaaagagg agaaaggtac cgcatgcgta     240
```

```
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 123
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 123

```
tttgcnggc ttcccaacct taccagaggg cgccccagct ggcaattccg acgtctaaga     60
aaccattatt atcatgacat taacctataa aaataggcgt atcacgaggc cctttcgtct   120
tcacctcgag tccctatcag tgatagagat tgacacccct atcagtgata gagatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                      372
```

<210> SEQ ID NO 124
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 124

```
tttgcnnggc ttcccaacct taccagaggg cgccccagct ggcaattccg acgtctaaga    60
aaccattatt atcatgacat taacctataa aaataggcgt accacgaggc cctttcgtct   120
tcacctcgag tccctaccag tgatagagat tgacatccct atcagtgata gaaatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                      372
```

<210> SEQ ID NO 125
<211> LENGTH: 372
<212> TYPE: DNA
<213> ORGANISM: Artificial
<220> FEATURE:
<223> OTHER INFORMATION: mutant sequence of bacteriophage lambda tetO
      promoter

```
<220> FEATURE:
<221> NAME/KEY: misc_feature
<222> LOCATION: (368)..(368)
<223> OTHER INFORMATION: n is a, c, g, or t

<400> SEQUENCE: 125
tttgcagggc ttcccaacct taccagaggg cgccccagct ggcaattccg acgtctaagg      60
aaccattatt atcatgacat taacctataa aaataggcgt atcacgaggc cctttcgtct     120
tcacctcgag tccctatcag tggtagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                          372

<210> SEQ ID NO 126
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 126
ttnnnnnggc ttcccaacct taccagaggg cgccccagct ggcaattccg acgtctaaga     60
aaccattatt attatgacat taacctataa aaataggcgt atcacgaggc cctttccgtct   120 tcacctcgag tccctatcag tgatagagat tgacatccct atcagtgata gaaatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                          372

<210> SEQ ID NO 127
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 127
ttnnnnnggc ttcccaacct taccagaggg cgccccagct ggcaattccg acgtctaaga     60
agccattatt atcatgacat taacctataa aagtaggcgt gtcacaaggc cctttcgtct    120
tcacctcgag tccctatcag cgatagagat tgacatccct atcagtgacc gagatactga    180
gcacatcagc aggacgcact gaccgaattc attaaagagg agaaaggtac cgcatgcgta    240
```
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta    372

<210> SEQ ID NO 128
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 128
ttnnnnnggc ttcccaacct taccagaggg cgccccagct ggcaattccg acgtctaaga    60
gaccattatt atcgtgacat taacctataa gaacaggcgt gtcacgaggc cctttcgtct    120
tcacctcgag tccctatcag tgacagagat tgacacccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta    372

<210> SEQ ID NO 129
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 129 tttgcnggge ttcccaacct taccagaggg cgccccagct ggcaattccg acgtctaaga    60
aaccattatt accatgccat taacctataa aaataggcgt atcacgaggc cctttcgcct    120
tcacctcgag tccctatcag tgatagagat tgacacccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta    372

<210> SEQ ID NO 130
<211> LENGTH: 372
<212> TYPE: DNA
<213> ORGANISM: Artificial
<220> FEATURE:
<223> OTHER INFORMATION: mutant sequence of bacteriophage lambda tetO
      promoter

```
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 130
ttnnnnnggc ttcccaacct taccagaggg cgccccagct ggcaattccg acgcctaaga      60
aaccattatt atcatgacat tagcctataa aaataggcgt accacgaggc cctttcgtct    120
tcacctcgag tccctatcag tgatagagat tgacacccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 131
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 131
tttgcngggc ttcccaacct taccagaggg cgccccagct ggcaattccg acgtctaaga     60
aaccattatt atcatgacat taacctataa aaataggcgt atcacgaggc cctttcgtct    120
tcacctcgag tccctatcag tgatagagac tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 132
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 132
ttnnnnnggc ttcccaacct taccagaggg cgccccagct ggcaattccg acgtctaaga     60
aaccattatt atcatgacat taacctataa aaataggcgt atcacgaggc cctttcgtct    120
```

```
tcacctcgag tccctatcag tgatagagat tgacacccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

```
<210> SEQ ID NO 133
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 133
```

```
ttnnnnnggc ttcccaacct taccagaggg cgccccagct ggcaattccg acgtctaaga     60
aaccattatt atcatgacat taacctataa aaataggcgt atcacgaggc cctctcgtct    120
tcacctcgag tccctatcag tgatagggat tgacatccct atcagtgata gagacactgg    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

```
<210> SEQ ID NO 134
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t

<400> SEQUENCE: 134
```

```
ttnnnnnggc ttcccaacct taccagaggg cgccccagct ggcaattccg acgtctaaga     60
aaccattgtt atcatgacat taacctataa aaataggcgt atcacgaggc cctttcgtct    120
tcacctcgag tccctatcag tgatagagat tgacacccct atcagtgaca gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaaatt ta                                                        372
```

```
<210> SEQ ID NO 135
<211> LENGTH: 372
<212> TYPE: DNA
<213> ORGANISM: Artificial
<220> FEATURE:
<223> OTHER INFORMATION: mutant sequence of bacteriophage lambda tet0
      promoter
```

```
<220> FEATURE:
<221> NAME/KEY: misc_feature
<222> LOCATION: (3)..(7)
<223> OTHER INFORMATION: n is a, c, g, or t

<400> SEQUENCE: 135
ttnnnnnggc ttcccaacct taccagaggg cgccccagct ggcaattccg acgtctaaga      60
aaccattatt atcatgacat taacctataa aaataggcgt atcacgaggc ccctttgtct     120
tcacctcgag cccctatcag tgatagagat tgacaccccct atcagtgata gagatactga    180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaaatt ta                                                         372

<210> SEQ ID NO 136
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 136
ttnnnnnggc ttcccaacct taccagaggg cgccccagct ggcaattccg acgtctaaga      60
aaccattact atcatgacat taacctataa aagtaggcgt atcacgaggc cctttcgtct     120
tcacctcgag tccctatcag tgatagagat tgacatctct atcagtgata gagacactga    180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 137
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 137
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacaccccct atcagtgcta gagatactga    180
gcacatcagc aggacgcact gaccgaattc attaaagagg agaaaggtac cgcatgcgta     240
```

-continued

```
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 138
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 138

```
ttnnnnnggc ttcccaacct taccagaggg cgccccagct ggcaattccg acgtctaaga     60
aaccattatt atcatgacat taacccataa aaataggcgt atcatgaggc cctttcgtct    120
tcacctcgag tccctatcag tgatagagat tgacacccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 139
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t

<400> SEQUENCE: 139

```
tttgcnnggc ttcccaacct taccagaggg cgccccagct ggcaattccg acgtctagga     60
aaccgttatt atcatgacgc caacctataa agataggcgt gtcacgaggc cctttcgcct    120
tcacctcgag ccctatcag tgatagagat tgacacccct gtcagtgata gggatactga     180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaaatt ta                                                        372
```

<210> SEQ ID NO 140
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t

```
<220> FEATURE:
<221> NAME/KEY: misc_feature
<222> LOCATION: (368)..(368)
<223> OTHER INFORMATION: n is a, c, g, or t

<400> SEQUENCE: 140
tttgcnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gggatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                          372

<210> SEQ ID NO 141
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t

<400> SEQUENCE: 141
ttnnnnnggc ttcccaacct taccagaggg cgccccagct ggcaattccg acgtctgaga      60
agccattatt atcatgacat taacctataa aagtaggcgt atcacgaggc cctttcgtct     120
tcacctcaag cccctatcag tgatagagat tgacatccct atcagtgata gagacactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaaatt ta                                                          372

<210> SEQ ID NO 142
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 142
ttngnanggc ttcccaacct taccagaggg cgccccagct ggcaattccg acgtctaaga      60
aaccattatt atcatgacat taacctataa aaataggcgt atcacgaggc cctttcgtct     120
```

```
tcacctcgag tccctatcag tgatagagat tgacatccct atcagtgata gagacactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 143
<211> LENGTH: 372
<212> TYPE: DNA
<213> ORGANISM: Artificial
<220> FEATURE:
<223> OTHER INFORMATION: mutant sequence of bacteriophage lambda tet0 promoter
<220> FEATURE:
<221> NAME/KEY: misc_feature
<222> LOCATION: (3)..(6)
<223> OTHER INFORMATION: n is a, c, g, or t

<400> SEQUENCE: 143

```
ttnnnngggc ttcccaacct taccagaggg cgccccagct ggcaattccg acgtctaaga    60
agccattact atcatgacat taacctatag gaataggcgc atcacggggc ccttccgcct   120
tcacctcgga tccctgtcag tgctagagat tgacatccct accggtgata aagatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaaatt ta                                                        372
```

<210> SEQ ID NO 144
<211> LENGTH: 372
<212> TYPE: DNA
<213> ORGANISM: Artificial
<220> FEATURE:
<223> OTHER INFORMATION: mutant sequence of bacteriophage lambda tet0 promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 144

```
ttnnnnnggc ttcccaacct taccagaggg cgccccagct ggcaattccg acgtctaaga    60
aaccattatt atcatgacac taacctataa aaataggcgc atcacgaggc ctttcgtct   120 ccacctcaag ccctatcag tgatagagat tgacatcccc gccggtgata gagacactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 145
<211> LENGTH: 372
<212> TYPE: DNA
<213> ORGANISM: Artificial
<220> FEATURE:
<223> OTHER INFORMATION: mutant sequence of bacteriophage lambda tet0 promoter

```
<220> FEATURE:
<221> NAME/KEY: misc_feature
<222> LOCATION: (3)..(7)
<223> OTHER INFORMATION: n is a, c, g, or t

<400> SEQUENCE: 145
ttnnnnnggc ttcccaacct taccagaggg cgccccagct ggcaattccg acgtctgaga      60
ggccattatt atcgtggcat tggcctataa aggcaggcgt gtcacgagac cctctcgtct     120
ccgcctcggg tccctatcaa tggtagagat tgacatcccc atcagtggtg gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaaatt ta                                                         372

<210> SEQ ID NO 146
<211> LENGTH: 371
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t

<400> SEQUENCE: 146
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaatta ttaaagagga gaaaggtacc gcatgcgtaa     240
aggagaagaa cttttcactg gagttgtccc aattcttgtt gaattagatg gtgatgttaa     300
tgggcacaaa ttttctgtca gtggagaggg tgaaggtgat gcaacatacg gaaaacttac     360 ccttaantt a                                                           371

<210> SEQ ID NO 147
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 147
tttgcngggc ttcccaacct taccagaggg cgccccagct ggcaattccg acgtctaaga      60
aaccattatt atcatgacgt taacctataa gaataggcgt atcacgaggc cctttcgtct     120
tcacctcgag tccctatcgg tgacagagat tgacatccct atcagtgata gagacactga     180
gcacatcagc aggacgcact gaccgaattc attaaagagg agaaaggtac cgcatgcgta     240
```

| | |
|---|---|
| aaggagaaga actttcact ggagttgtcc caattcttgt tgaattagat ggtgatgtta | 300 |
| atgggcacaa atttctgtc agtggagagg gtgaaggtga tgcaacatac ggaaaactta | 360 |
| cccttaantt ta | 372 |

<210> SEQ ID NO 148
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 148

| | |
|---|---|
| tttgcnggc ttcccaacct taccagaggg cgccccagct ggcaattccg acgtctaagg | 60 |
| aactattatt atcatgacat taacctataa aaataggcgt atcacgaggc ccttcgtct | 120 |
| tcacctcgag tccctatcag tgatagagat tgacatccct atcagtgata gagacactga | 180 |
| gcacatcagc aggacgcact gaccgaattc attaaagagg agaaaggtac cgcatgcgta | 240 |
| aaggagaaga actttcact ggagttgtcc caattcttgt tgaattagat ggtgatgtta | 300 |
| atgggcacaa atttctgtc agtggagagg gtgaaggtga tgcaacatac ggaaaactta | 360 |
| cccttaantt ta | 372 |

<210> SEQ ID NO 149
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t

<400> SEQUENCE: 149

| | |
|---|---|
| tttgcnggc ttcccaacct taccagaggg cgccccagct ggcaattccg acgtctaaga | 60 |
| aaccattatt atcatgacat taacctataa aaataggcgt atcacgaggc cctttcgtct | 120 |
| tcacctcgag tccctatcag tgatagggat tgacatccct atcagtgata gagacactga | 180 |
| gcacatcagc aggacgcact gaccgaattc attaaagagg agaaaggtac cgcatgcgta | 240 |
| aaggagaaga actttcact ggagttgtcc caattcttgt tgaattagat ggtgatgtta | 300 |
| atgggcacaa atttctgtc agtggagagg gtgaaggtga tgcaacatac ggaaaactta | 360 |
| cccttaaatt ta | 372 |

<210> SEQ ID NO 150
<211> LENGTH: 143
<212> TYPE: DNA
<213> ORGANISM: Artificial
<220> FEATURE:
<223> OTHER INFORMATION: mutant sequence of bacteriophage lambda tetO
      promoter

<400> SEQUENCE: 150

```
attccgacgt ctaagaaacc attattatca tgacattaac ctataaaaat aggcgtatca    60
cgaggccctt tcgtcttcac ctcgagtccc tatcggtgat agagattgac atccctatcg   120
gtgatagaga tactgagcac atc                                           143
```

<210> SEQ ID NO 151
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 151

```
tttgcnnggc ttcccaacct taccagaggg cgccccagct ggcaattccg acgtctaaga    60
aaccattatt atcatgacat taacctataa aaataggcgt atcacgaggc cctttcgtct   120
tcacctcgag tccctatcag tgatagagat tgacatccct atcagtgata gagacactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                       372
```

<210> SEQ ID NO 152
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 152

```
tttgcnlggc ttcccaacct taccagaggg cgccccagct ggcaattccg acgtctaaga    60
aaccattatt atcatgacat taacctataa aaacaggcgt atcacgaggc cctttcgtct   120
tcacctcggg tccctatcag tgatagagat tgacatccct atcagtgata gagacactga   180
gcgcatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                       372
```

<210> SEQ ID NO 153
<211> LENGTH: 372
<212> TYPE: DNA
<213> ORGANISM: Artificial
<220> FEATURE:
<223> OTHER INFORMATION: mutant sequence of bacteriophage lambda tet0
       promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 153
tttgcnnggc ttcccaacct taccagaggg cgccccagct ggcaattccg acgtctaaga        60
aaccattatt atcatgacat taacctataa aaataggcgt accacgaggc cctttcgtct       120
tcacctcgag tccctatcag tgatagagat tgacatccct atcagtgata gagacactga      180
gcacatcagc aggacgcact gaccgaattc attaaagagg agaaaggtac cgcatgcgta      240
aaggagaaga acttttcact ggagttgtcc caattcttgt tgaattagat ggtgatgtta      300
atgggcacaa attttctgtc agtggagagg gtgaaggtga tgcaacatac ggaaaactta      360
cccttaantt ta                                                          372

<210> SEQ ID NO 154
<211> LENGTH: 372
<212> TYPE: DNA
<213> ORGANISM: Artificial
<220> FEATURE:
<223> OTHER INFORMATION: mutant sequence of bacteriophage lambda tet0
       promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 154
tttgcnnggc ttcccaacct taccagaggg cgccccagct ggcaattccg acgtctgaga       60
aaccattatt atcatgacat tagcctataa aaataggcgt atcacggggc cctctcgtct      120
tcacctcaag tccctaccag tgatagagat tgacatccct atcagtgata gagacactga      180
gcacatcagc aggacgcact gaccgaattc attaaagagg agaaaggtac cgcatgcgta      240
aaggagaaga acttttcact ggagttgtcc caattcttgt tgaattagat ggtgatgtta      300
atgggcacaa attttctgtc agtggagagg gtgaaggtga tgcaacatac ggaaaactta      360
cccttaantt ta                                                          372

<210> SEQ ID NO 155
<211> LENGTH: 372
<212> TYPE: DNA
<213> ORGANISM: Artificial
<220> FEATURE:
<223> OTHER INFORMATION: mutant sequence of bacteriophage lambda tet0
       promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 155

```
tttgcngggc ttcccaacct taccagaggg cgccccagct ggcaattccg acgtctaaga      60
aaccattatt atcatggcat taacctataa aaataggcgt atcgcgaggc cctttcgtct     120
tcacctcgag tccctatcag tgatagagat tgacacccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372
```

<210> SEQ ID NO 156
<211> LENGTH: 372
<212> TYPE: DNA
<213> ORGANISM: Artificial
<220> FEATURE:
<223> OTHER INFORMATION: mutant sequence of bacteriophage lambda tetO
promoter
<220> FEATURE:
<221> NAME/KEY: misc_feature
<222> LOCATION: (6)..(6)
<223> OTHER INFORMATION: n is a, c, g, or t

<400> SEQUENCE: 156

```
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tggtaaagat tgacatccct atcagtgata gggatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaaatt ta                                                         372
```

<210> SEQ ID NO 157
<211> LENGTH: 372
<212> TYPE: DNA
<213> ORGANISM: Artificial
<220> FEATURE:
<223> OTHER INFORMATION: mutant sequence of bacteriophage lambda tetO
promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 157

```
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctaccag tgacagggat tgacatcccc atcagtgata gagagactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372
```

```
<210> SEQ ID NO 158
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 158
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 159
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 159
tttgcnnggc ttcccaacct taccagaggg cgccccagct ggcaattccg acgtctaaga      60
aaccattatt atcatgacat taacctataa aaataggcgt accacgaggc cctttcgtct     120
tcacctcgag tccctatcag tgatagagat tgacatccct atcagtgata gagacactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 160
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
```

```
<220> FEATURE:
<221> NAME/KEY: misc_feature
<222> LOCATION: (368)..(368)
<223> OTHER INFORMATION: n is a, c, g, or t

<400> SEQUENCE: 160
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 161
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 161
tttgcnnggc ttcccaacct taccagaggg cgccccagct ggcaattccg acgtctaaga      60
aaccgttatt atcatgacat tagcctataa aaataggcgt atcacgaggc ccttccgtct     120
tcacctcgag tccctatcag tgatagaggt tgacaccct atcagtgaca gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 162
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 162
tttgcnnggc ttcccaacct taccagaggg cgccccagct ggcaattccg acgtctaaga      60
aaccgttatt atcatgacat tagcctataa aaataggcgt atcacgaggc ccttccgtct     120
tcacctcgag tccctatcag tgatagaggt tgacaccct atcagtgaca gagatactga     180
gcacatcagc aggacgcact gaccgaattc attaaagagg agaaaggtac cgcatgcgta     240
```

| | | |
|---|---|---|
| aaggagaaga actttcact ggagttgtcc caattcttgt tgaattagat ggtgatgtta | 300 | |
| atgggcacaa attttctgtc agtggagagg gtgaaggtga tgcaacatac ggaaaactta | 360 | |
| cccttaantt ta | 372 | |

<210> SEQ ID NO 163
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 163

| | | |
|---|---|---|
| tttgcnnggc ttcccaacct taccagaggg cgccccagct ggcaattccg acgtctaaga | 60 | |
| aaccgttatt atcatgacat tagcctataa aaataggcgt atcacgaggc ccttccgtct | 120 | |
| tcacctcgag tccctatcag tgatagaggt tgacacccct atcagtgaca gagatactga | 180 | |
| gcacatcagc aggacgcact gaccgaattc attaaagagg agaaaggtac cgcatgcgta | 240 | |
| aaggagaaga actttcact ggagttgtcc caattcttgt tgaattagat ggtgatgtta | 300 | |
| atgggcacaa attttctgtc agtggagagg gtgaaggtga tgcaacatac ggaaaactta | 360 | |
| cccttaantt ta | 372 | |

<210> SEQ ID NO 164
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 164

| | | |
|---|---|---|
| ttnnnnnggc ttcccaacct taccagaggg cgccccagct ggcaattccg acgtctaaga | 60 | |
| aaccattatt atcatgacat taacctataa aaataggcgt atcacgaggc cctttcgtct | 120 | |
| tcacctcgag tccctatcag tgatagagat tgacatccct atcagtgata gagatactga | 180 | |
| gcacatcagc aggacgcact gaccgaattc attaaagagg agaaaggtac cgcatgcgta | 240 | |
| aaggagaaga actttcact ggagttgtcc caattcttgt tgaattagat ggtgatgtta | 300 | |
| atgggcacaa attttctgtc agtggagagg gtgaaggtga tgcaacatac ggaaaactta | 360 | |
| cccttaantt ta | 372 | |

<210> SEQ ID NO 165
<211> LENGTH: 372
<212> TYPE: DNA
<213> ORGANISM: Artificial
<220> FEATURE:
<223> OTHER INFORMATION: mutant sequence of bacteriophage lambda tetO
      promoter

```
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 165
ttnnnnnggc ttcccaacct taccagaggg cgccccagct ggcaattccg acgtctaaga    60
aaccattatt atcatgacat taacctataa aaataggcgt atcacgaggc cctttcgtct   120
tcacctcgag tccctatcag tgatagagat tgacatccct atcagtgata gagatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                       372

<210> SEQ ID NO 166
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 166
ttnnnnnggc ttcccaacct taccagaggg cgccccagct ggcaattccg acgtctaaga    60
aaccattatt atcatgacat taacctataa aaataggcgt atcacgaggc cctttcgtct   120
tcacctcgag tccctatcag tgatagagat tgacatccct atcagtgata gagatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                       372

<210> SEQ ID NO 167
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 167
ttnnnnnggc ttcccaacct taccagaggg cgccccagct ggcaattccg acgtctaaga    60
gaccattatt atcatgacat tgacctataa aaatagacgt accacgaggc cctttcgtct   120
```

```
tcacctcgag tccctatcag tggtagagat tgacatccct atcggtggta gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

```
<210> SEQ ID NO 168
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 168
ttnnnnnggc ttcccaacct taccagaggg cgccccagct ggcaattccg acgtctaaga     60
aaccattatt atcatgacgt taacctataa aaataggcgt atcacgaggc cctttcgtct    120
tcacctcgag tccctatcag tgatagagat tgacaccect atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

```
<210> SEQ ID NO 169
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 169 ttnnnnggge ttcccaacct taccagaggg cgccccagct ggcaattccg acgtctaaga     60
aaccattatt atcatgacac taacctataa gaataggcgt atcacgaggc cctttcgtct    120
tcacctcgag tccctatcag tgatagagat tgacatccct atcagtgata gagacactga    180
gcacatcagc acgacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

```
<210> SEQ ID NO 170
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t

<400> SEQUENCE: 170
tttgcnnggc ttcccaacct taccagaggg cgccccagct ggcaattccg acgtctaaga      60
aaccattatt atcatgacat caacctatag aaataggcgt gtcacgaggc cctttcgtct     120
tcacctcgag tccctatcag tggcagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaaatt ta                                                        372

<210> SEQ ID NO 171
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 171
tttgcnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 172
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
```

<400> SEQUENCE: 172

```
tttgcnnggc ttcccaacct taccagaggg cgccccagct ggcaattccg acgtctaaga      60
aaccattatt atcatgacat taacctataa aaataggcgt atcacggggc cctttcgtct     120
tcacctcgag tccctatcag tgatagaggt tgacatccct atcagtgata gaaatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                         372
```

<210> SEQ ID NO 173
<211> LENGTH: 372
<212> TYPE: DNA
<213> ORGANISM: Artificial
<220> FEATURE:
<223> OTHER INFORMATION: mutant sequence of bacteriophage lambda tetO promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 173

```
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                         372
```

<210> SEQ ID NO 174
<211> LENGTH: 372
<212> TYPE: DNA
<213> ORGANISM: Artificial
<220> FEATURE:
<223> OTHER INFORMATION: mutant sequence of bacteriophage lambda tetO promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 174

```
ttnnnanggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga    180
gcacatcagc aggacgcact gaccgaattc attaaagagg agaaaggtac cgcatgcgta    240
```

| aaggagaaga acttttcact ggagttgtcc caattcttgt tgaattagat ggtgatgtta | 300 |
| atgggcacaa attttctgtc agtggagagg gtgaaggtga tgcaacatac ggaaaactta | 360 |
| cccttaantt ta | 372 |

<210> SEQ ID NO 175
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 175

| ttnnnngggc ttcccaacct taccagaggg cgccccagct ggcaattccg acgtctaagg | 60 |
| aaccattatt atcatgacat taacctataa aagtaggcgt atcacgaggc cctttcgcct | 120 |
| tcacctcgag tccctatcag tgatagagat tgacacccct atcagtgata gagatactga | 180 |
| gcacatcagc aggacgcact gaccgaattc attaaagagg agaaaggtac cgcatgcgta | 240 |
| aaggagaaga acttttcact ggagttgtcc caattcttgt tgaattagat ggtgatgtta | 300 |
| atgggcacaa attttctgtc agtggagagg gtgaaggtga tgcaacatac ggaaaactta | 360 |
| cccttaantt ta | 372 |

<210> SEQ ID NO 176
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 176

| tttgcnggggc ttcccaacct taccagaggg cgccccagct ggcaattccg acgtctaaga | 60 |
| aaccattatt atcatgacat taacctataa aaataggcgt atcacgaggc cctttcgtct | 120 |
| tcacctcgag tccctatcag tgatagagat tgacacccct atcagtgata gagatactga | 180 |
| gcacatcagc aggacgcact gaccgaattc attaaagagg agaaaggtac cgcatgcgta | 240 |
| aaggagaaga acttttcact ggagttgtcc caattcttgt tgaattagat ggtgatgtta | 300 |
| atgggcacaa attttctgtc agtggagagg gtgaaggtga tgcaacatac ggaaaactta | 360 |
| cccttaantt ta | 372 |

<210> SEQ ID NO 177
<211> LENGTH: 334
<212> TYPE: DNA
<213> ORGANISM: Artificial
<220> FEATURE:
<223> OTHER INFORMATION: mutant sequence of bacteriophage lambda tet0
      promoter

```
<220> FEATURE:
<221> NAME/KEY: misc_feature
<222> LOCATION: (330)..(330)
<223> OTHER INFORMATION: n is a, c, g, or t

<400> SEQUENCE: 177
ctggcaattc cgacgtctaa gaaaccatta ttatcatgac attaacctat aaaagtaggc      60
ataccatgag gccctcccgc cttcacctcg agtccttatc agtggtagag gttgacgccc     120
ctatcggcga tggagatact gggcacatca gcaggacgca ctgaccgaat tcattaaaga     180
ggagaaaggt accgcatgcg taaaggagaa gaacttttca ctggagttgt cccaattctt     240
gttgaattag atggtgatgt taatgggcac aaattttctg tcagtggaga gggtgaaggt     300
gatgcaacat acggaaaact tacccttaan ttta                                 334

<210> SEQ ID NO 178
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 178
tttgcngggc ttcccaacct taccagaggg cgccccagct ggcaattccg acgtctaaga     60
aaccattatt atcatgacat taacctataa aagtaggcgt atcacgaggc cctttcgtct    120
tcacctcggg tccctatcag tgatagagat tgacgtccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 179
<211> LENGTH: 334
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (330)..(330)
<223> OTHER INFORMATION: n is a, c, g, or t

<400> SEQUENCE: 179
ctggcaattc cgacgtctaa gaaaccatta ttatcatgac attaacctat aaaaacaggc     60
gtatcacgag gcccttccgt cttcacctcg agtccctatc agtgatagag attgacatcc    120
ctatcagtga tggagacact gagcacatca gcaggacgca ctgaccgaat tcattaaaga    180
ggagaaaggt accgcatgcg taaaggagaa gaacttttca ctggagttgt cccaattctt    240
gttgaattag atggtgatgt taatgggcac aaattttctg tcagtggaga gggtgaaggt    300
gatgcaacat acggaaaact tacccttaan ttta                                 334
```

<210> SEQ ID NO 180
<211> LENGTH: 372
<212> TYPE: DNA
<213> ORGANISM: Artificial
<220> FEATURE:
<223> OTHER INFORMATION: mutant sequence of bacteriophage lambda tetO
    promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 180
tttgcnnggc ttcccaacct taccagaggg cgccccagct ggcaattccg acgtctaaga      60
aaccactatt accacgacat taacctatag agataggcgc atcacgaggc cctttcgtct     120
tcacctcgag tccctatcag tgacagagat tgacatccct attagtgata gagatactga     180
gcacatcagc aggacgcact gaccgaattc attaaagagg agaaaggtac cgcatgcgta     240
aaggagaaga actttcact ggagttgtcc caattcttgt tgaattagat ggtgatgtta     300
atgggcacaa attttctgtc agtggagagg gtgaaggtga tgcaacatac ggaaaactta     360
cccttaantt ta                                                         372

<210> SEQ ID NO 181
<211> LENGTH: 347
<212> TYPE: DNA
<213> ORGANISM: Artificial
<220> FEATURE:
<223> OTHER INFORMATION: mutant sequence of bacteriophage lambda tetO
    promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 181
tttgcnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat actgagcaca tcagcaggac gcactgaccg     180
aattcattaa agaggagaaa ggtaccgcat gcgtaaagga gaagaacttt tcactggagt     240
tgtcccaatt cttgttgaat tagatggtga tgttaatggg cacaaatttt ctgtcagtgg     300
agagggtgaa ggtgatgcaa catacggaaa acttaccctt aanttta                  347

<210> SEQ ID NO 182
<211> LENGTH: 347
<212> TYPE: DNA
<213> ORGANISM: Artificial
<220> FEATURE:
<223> OTHER INFORMATION: mutant sequence of bacteriophage lambda tetO
    promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

```
<220> FEATURE:
<221> NAME/KEY: misc_feature
<222> LOCATION: (343)..(343)
<223> OTHER INFORMATION: n is a, c, g, or t

<400> SEQUENCE: 182
ttnnnanggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat actgagcaca tcagcaggac gcactgaccg     180
aattcattaa agaggagaaa ggtaccgcat gcgtaaagga gaagaacttt tcactggagt     240
tgtcccaatt cttgttgaat tagatggtga tgttaatggg cacaaatttt ctgtcagtgg     300
agagggtgaa ggtgatgcaa catacggaaa acttacccctt aanttta                 347

<210> SEQ ID NO 183
<211> LENGTH: 314
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (310)..(310)
<223> OTHER INFORMATION: n is a, c, g, or t

<400> SEQUENCE: 183
cccagctggc aattccgacg tctaagaaac cattattatc atgacattaa cctataaaaa      60
taggcgtatc acgaggccct ttcgtcttca cctcgagtcc ctatcagtga tagagatact     120
gagcacatca gcaggacgca ctgaccgaat tcattaaaga ggagaaaggt accgcatgcg     180
taaaggagaa gaacttttca ctggagttgt cccaattctt gttgaattag atggtgatgt     240
taatgggcac aaattttctg tcagtggaga gggtgaaggt gatgcaacat acggaaaact     300 taccccttaan ttta                                                      314

<210> SEQ ID NO 184
<211> LENGTH: 317
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (313)..(313)
<223> OTHER INFORMATION: n is a, c, g, or t

<400> SEQUENCE: 184
cgccccagct ggcaattccg acgtctaaga aaccattatt atcatgacat taacctataa      60
aaataggcgt atcacgaggc cctttcgtct tcacctcgag tccctatcag tgatagagat     120
actgagcaca tcagcaggac gcactgaccg aattcattaa agaggagaaa ggtaccgcat     180
gcgtaaagga gaagaacttt tcactggagt tgtcccaatt cttgttgaat tagatggtga     240
tgttaatggg cacaaatttt ctgtcagtgg agagggtgaa ggtgatgcaa catacggaaa     300 acttacccctt aanttta                                                   317

<210> SEQ ID NO 185
<211> LENGTH: 308
<212> TYPE: DNA
<213> ORGANISM: Artificial
```

```
<220> FEATURE:
<223> OTHER INFORMATION: mutant sequence of bacteriophage lambda tet0
      promoter
<220> FEATURE:
<221> NAME/KEY: misc_feature
<222> LOCATION: (304)..(304)
<223> OTHER INFORMATION: n is a, c, g, or t

<400> SEQUENCE: 185
tggcaattcc gacgtctaag aaaccattat tatcatgaca ttaacctata aaataggcg      60 tatcacgagg ccctttcgtc ttcacctcga gtccctatca gtgatagaga tactgagcac    120
atcagcagga cgcactgacc gaattcatta agaggagaa aggtaccgca tgcgtaaagg    180
agaagaactt ttcactggag ttgtcccaat tcttgttgaa ttagatggtg atgttaatgg   240
gcacaaattt tctgtcagtg gagagggtga aggtgatgca acatacggaa aacttaccct   300 taanttta                                                             308

<210> SEQ ID NO 186
<211> LENGTH: 315
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (311)..(311)
<223> OTHER INFORMATION: n is a, c, g, or t

<400> SEQUENCE: 186
ccccagctgg caattccgac gtctaagaaa ccattattat catgacatta acctataaaa    60
ataggcgtat cacgaggccc tttcgtcttc acctcgagtc cctatcagtg atagagatac   120
tgagcacatc agcaggacgc actgaccgaa ttcattaaag aggagaaagg taccgcatgc   180
gtaaaggaga gaacttttc actggagttg tcccaattct tgttgaatta gatggtgatg    240
ttaatgggca aaattttct gtcagtggag agggtgaagg tgatgcaaca tacggaaaac    300 ttaccccttaa nttta                                                    315

<210> SEQ ID NO 187
<211> LENGTH: 302
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (298)..(298)
<223> OTHER INFORMATION: n is a, c, g, or t

<400> SEQUENCE: 187
ttccgacgtc taagaaacca ttattatcat gacattaacc tataaaaata ggcgtatcac    60
gaggcccttt cgtcttcacc tcgagtccct atcagtgata gagatactga gcacatcagc   120
aggacgcact gaccgaattc attaaagagg agaaaggtac cgcatgcgta aaggagaaga   180
acttttcact ggagttgtcc caattcttgt tgaattagat ggtgatgtta atgggcacaa    240
attttctgtc agtggagagg gtgaaggtga tgcaacatac ggaaaactta cccttaantt   300
ta                                                                   302
```

<210> SEQ ID NO 188
<211> LENGTH: 347
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 188
ttnnnanggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat actgagcaca tcagcaggac gcactgaccg     180
aattcattaa agaggagaaa ggtaccgcat gcgtaaagga gaagaacttt tcactggagt     240
tgtcccaatt cttgttgaat tagatggtga tgttaatggg cacaaatttt ctgtcagtgg     300
agagggtgaa ggtgatgcaa catacggaaa acttacccct aanttta                   347

<210> SEQ ID NO 189
<211> LENGTH: 314
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (310)..(310)
<223> OTHER INFORMATION: n is a, c, g, or t

<400> SEQUENCE: 189
cccagctggc aattccgacg tctaagaaac cattattatc atgacattaa cctataaaaa      60
taggcgtatc acgaggccct ttcgtcttca cctcgagtcc ctatcagtga tagagatact     120
gagcacatca gcaggacgca ctgaccgaat tcattaaaga ggagaaaggt accgcatgcg     180
taaaggagaa gaacttttca ctggagttgt cccaattctt gttgaattag atggtgatgt     240
taatgggcac aaattttctg tcagtggaga gggtgaaggt gatgcaacat acggaaaact     300 taccccttaan ttta                                                      314

<210> SEQ ID NO 190
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

```
<400> SEQUENCE: 190 tttgcnggc ttcccaacct taccagaggg cgccccagct ggcaattccg acgtctaaga      60
aaccattatt atcatgacat taacctgtag aagtaggcgt atcacgaggc cctttcgcct    120
tcacctcgag tccctattag tgatagaggt tgacacccct atcagtggta gggatactga    180
gcgcatcagc aggacgcact gaccgaattc attaaagagg agaaggtac cgcatgcgta     240 aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 191
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 191
tttgcnnggc ttcccaacct taccagaggg cgccccagct ggcaattccg acgtctaaga    60
aaccattatt atcatgacat taacctataa aataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaggtac cgcatgcgta    240 aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 192
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 192 tttgcnggc ttcccaacct taccagaggg cgccccagct ggcaattccg acgtctaaga     60
aaccattatt atcatgacat taacctataa aataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaggtac cgcatgcgta    240 aaggagaaga acttttcact ggagttgtcc caattcttgt tgaattagat ggtgatgtta    300
```

```
atgggcacaa attttctgtc agtggagagg gtgaaggtga tgcaacatac ggaaaactta      360
cccttaantt ta                                                         372
```

<210> SEQ ID NO 193
<211> LENGTH: 377
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t

<400> SEQUENCE: 193

```
ttnnnttnnn anggcttccc aaccttacca gagggcgccc cagctggcaa ttccgacgtc       60
taagaaacca ttattatcat gacattaacc tataaaaata ggcgtatcac gaggcccttt      120
cgtcttcacc tcgagtccct atcagtgata gagattgaca tccctatcag tgatagagat      180
actgagcaca tcagcaggac gcactgaccg aattcattaa agaggagaaa ggtaccgcat      240
gcgtaaagga gaagaacttt tcactggagt tgtcccaatt cttgttgaat tagatggtga      300
tgttaatggg cacaaatttt ctgtcagtgg agagggtgaa ggtgatgcaa catacggaaa      360
acttaccctt aanttta                                                    377
```

<210> SEQ ID NO 194
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 194

```
tttgcnnggc ttcccaacct taccagaggg cgccccagct ggcaattccg acgtctaaga       60
aaccattatt atcatgacat taacctataa aaataggcgt atcacgaggc cctttcgtct      120
tcacctcgag tccctatcag tgatagagat tgacatccct atcagtgata gagatactga      180
gcacatcagc aggacgcact gaccgaattc attaaagagg agaaaggtac cgcatgcgta      240
aaggagaaga acttttcact ggagttgtcc caattcttgt tgaattagat ggtgatgtta      300
atgggcacaa attttctgtc agtggagagg gtgaaggtga tgcaacatac ggaaaactta      360
cccttaantt ta                                                         372
```

```
<210> SEQ ID NO 195
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 195
tttgcngggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 196
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 196
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 197
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
```

```
<220> FEATURE:
<221> NAME/KEY: misc_feature
<222> LOCATION: (368)..(368)
<223> OTHER INFORMATION: n is a, c, g, or t

<400> SEQUENCE: 197
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga actttcact ggagttgtcc caattcttgt tgaattagat ggtgatgtta      300
atgggcacaa attttctgtc agtggagagg gtgaaggtga tgcaacatac ggaaaactta     360
cccttaantt ta                                                        372

<210> SEQ ID NO 198
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (4)..(7)
<223> OTHER INFORMATION: n is a, c, g, or t

<400> SEQUENCE: 198
tttnnnnggc ttcccaacct taccagaggg cgccccagct ggcaattccg acgtctaaga      60
aaccaccatt atcatgacat taacctatag aagtaggcgt atcacgaggc cctttcgtct     120
tcacctcgag tccctattag tgatagagat tgacaccccct accagtggta gagatactga     180
gcacatcagc aggacgcact gaccgaattc attaaagagg agaaaggtac cgcatgcgta     240
aaggagaaga actttcact ggagttgtcc caattcttgt tgaattagat ggtgatgtta      300
atgggcacaa attttctgtc agtggagagg gtgaaggtga tgcaacatac ggaaaactta     360
cccttaaatt ta                                                        372

<210> SEQ ID NO 199
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 199
ttnnnnnggc ttcccaacct taccagaggg cgccccagct ggcaattccg acgtctaagg      60
gatcattatt accatgacat taacctataa agataggcgt atcacgaggc cctttcgtct     120
tcacctcgag tccctatcag tgatagagat tgacatccct atcagtgata gagacactga     180
gcacatcagc aggacgcact gaccgaattc attaaagagg agaaaggtac cgcatgcgta     240
aaggagaaga actttcact ggagttgtcc caattcttgt tgaattagat ggtgatgtta      300
```
atgggcacaa attttctgtc agtggagagg gtgaaggtga tgcaacatac ggaaaactta    360
cccttaantt ta    372

<210> SEQ ID NO 200
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 200
tttgcngggc ttcccaacct taccagaggg cgccccagct ggcaattccg acgtctaaga    60
aaccattatt atcatgacat taacctataa aaataggcgt atcacgaggc cctctcgtct    120
tcaccccgag tccctatcag tgatggagat tgacaccccc t atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta    372

<210> SEQ ID NO 201
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 201
tttgcngggc ttcccaacct taccagaggg cgccccagct ggcaattccg acgtctaaga    60
aaccattatt atcatgacat taacctataa aaataggcgt atcacgaggc cctttcgtct    120
tcacctcgag tccctatcag tgatagagat tgacatcccc atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta    372

<210> SEQ ID NO 202
<211> LENGTH: 372
<212> TYPE: DNA
<213> ORGANISM: Artificial
<220> FEATURE:
<223> OTHER INFORMATION: mutant sequence of bacteriophage lambda tet0
      promoter

```
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 202
ttnnnnnggc ttcccaacct taccagaggg cgccccagct ggcaattccg acgtctaaga      60
aaccgttatt atcatgacat taacctataa aaataggcgt atcacgaggc cctttcgtct     120
tcacctcgag tccctatcag tgatagagat tgacatccct atcagtgata gagacactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 203
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 203 ttnnnnggc ttcccaacct taccagaggg cgccccagct ggcaattccg acgtctaaga       60
aaccattatt atcatgacat taacctataa aaataggcgt atcacgaggc cctttcgtct     120
tcacctcgag tccctatcag tgatagagat tgacatccct atcagtgata gagacactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                        372

<210> SEQ ID NO 204
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 204
ttnnnnnggc ttcccaacct taccagaggg cgccccagct ggcaattccg acgtctaaga      60
aaccattatt atcatgacat taacctatag aaataggcgt atcacgaggc ccttcgtct     120
```

```
tcacctcgag ccccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 205  
<211> LENGTH: 372  
<212> TYPE: DNA  
<213> ORGANISM: Artificial  
<220> FEATURE:  
<223> OTHER INFORMATION: mutant sequence of bacteriophage lambda tetO promoter  
<220> FEATURE:  
<221> NAME/KEY: misc_feature  
<222> LOCATION: (3)..(7)  
<223> OTHER INFORMATION: n is a, c, g, or t  
<220> FEATURE:  
<221> NAME/KEY: misc_feature  
<222> LOCATION: (368)..(368)  
<223> OTHER INFORMATION: n is a, c, g, or t

<400> SEQUENCE: 205

```
ttnnnnnggc ttcccaacct taccagaggg cgccccagct ggcaattccg acgtctaagg     60
gaccattatt accatagcat tagcctataa agataggcgc accacggggc cctttcgcct    120
tcaccccggg tccctatcaa cgacagagat tgacaccect atcagtgata gagatactgg    180
gcgcatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

<210> SEQ ID NO 206  
<211> LENGTH: 372  
<212> TYPE: DNA  
<213> ORGANISM: Artificial  
<220> FEATURE:  
<223> OTHER INFORMATION: mutant sequence of bacteriophage lambda tetO promoter  
<220> FEATURE:  
<221> NAME/KEY: misc_feature  
<222> LOCATION: (3)..(7)  
<223> OTHER INFORMATION: n is a, c, g, or t  
<220> FEATURE:  
<221> NAME/KEY: misc_feature  
<222> LOCATION: (368)..(368)  
<223> OTHER INFORMATION: n is a, c, g, or t

<400> SEQUENCE: 206

```
ttnnnnnggc ttcccaacct taccagaggg cgccccagct ggcaattccg acgtctaaga     60
aaccattatt atcatgacat taacctataa aataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

```
<210> SEQ ID NO 207
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 207
ttnnnnnggc ttcccaacct taccagaggg cgccccagct ggcaattccg acgtctaaga      60
aaccattatt atcatgacat taacctataa aaataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 208
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 208
ttnnnnnggc ttcccaacct taccagaggg cgccccagct ggcaattccg acgtctaaga      60
aaccattatt atcatgacat taacctataa aaataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 209
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
```

```
<220> FEATURE:
<221> NAME/KEY: misc_feature
<222> LOCATION: (368)..(368)
<223> OTHER INFORMATION: n is a, c, g, or t

<400> SEQUENCE: 209
tttgcngggc ttcccaacct taccagaggg cgccccagct ggcaattccg acgtctgaga     60
aaccattact gtcatgacat taacctacaa gaataggcgt atcacgaggc cccttcgtcc    120
tcacctcgag tccctatcag tgatagagat tgacatccct accagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                       372

<210> SEQ ID NO 210
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 210
tttgcngggc ttcccaacct taccagaggg cgccccagct ggcaattccg acgtctaaga     60
aaccattatt atcatgacat taacctataa aaataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                       372

<210> SEQ ID NO 211
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 211
tttgcngggc ttcccaacct taccagaggg cgccccagct ggcaattccg acgtctaaga     60
aaccattatt atcatgacat taacctataa aaataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
```

```
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 212
<211> LENGTH: 120
<212> TYPE: DNA
<213> ORGANISM: Artificial
<220> FEATURE:
<223> OTHER INFORMATION: mutant sequence of bacteriophage lambda tet0
      promoter

<400> SEQUENCE: 212
catcgtcgca gcgagtccct gtcaatgatc gagattgaca tcccggtcag tcagcctgcg     60
cctcagccca tcgccaggaa tgccataccg acagaattaa agtccggaaa ggtaccgcat    120

<210> SEQ ID NO 213
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 213
ttnnnanggc ttcccaacct taccagaggg cgccccagct ggcaattccg acgtctaagg     60
aaccattatt atcatggcat taacctatag aagtaggcgt atcacgaggc cctttcgtct    120
tcacctcgag tccctatcag tgatagaggt tgacgtccct atcagcgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 214
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 214 tttgcnggggc ttcccaacct taccagaggg cgccccagct ggcaattccg acgtctaaga    60
aaccattatt atcatgacat taacctataa aaataggcgt atcacgaggc cctttcgtct    120
```

```
tcacctcgag tccctatcag tggtagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 215
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 215
ttnnnnnggc ttcccaacct taccagaggg cgccccagct ggcaattccg acgtctaaga     60
aatcattatt atcatgacat taacctatag aaataggcgt atcacgaggc cctttcgtcc    120
tcacctcgag tccctatcag tgatagagat tgacatccct atcagtggta gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 216
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 216
ttnnnnnggc ttcccaacct taccagaggg cgccccagct ggcaattccg acgtctaaga     60
aaccattatt atcatgacat taacctataa aaataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372
```

```
<210> SEQ ID NO 217
<211> LENGTH: 371
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t

<400> SEQUENCE: 217
tttgcnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaatta ttaaagagga gaaaggtacc gcatgcgtaa     240
aggagaagaa cttttcactg gagttgtccc aattcttgtt gaattagatg gtgatgttaa     300
tgggcacaaa ttttctgtca gtggagaggg tgaaggtgat gcaacatacg gaaaacttac     360 ccttaantt t a                                                          371

<210> SEQ ID NO 218
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 218
ttnnnnnggc ttcccaacct taccagaggg cgccccagct ggcaattccg acgtctaaga      60
aaccattatt atcatgacat taacctataa aaataggcgt atcacgaggc cctttcgtct     120
tcacctcgag tccctatcag tgatagagat tgacatccct atcagtgata gagatactga     180
gcacatcagc aggacgcact gaccgaattc attaaagagg agaaaggtac cgcatgcgta     240
aaggagaaga acttttcact ggagttgtcc caattcttgt tgaattagat ggtgatgtta     300
atgggcacaa attttctgtc agtggagagg gtgaaggtga tgcaacatac ggaaaactta     360
cccttaantt ta                                                          372

<210> SEQ ID NO 219
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(5)
<223> OTHER INFORMATION: n is a, c, g, or t
```

```
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 219
ttnnnanggc ttcccaacct taccagaggg cgccccagct ggcaattccg acgtctaaga     60
aaccattatt atcatgacat taacctataa aaataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 220
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 220
tttgcnnggc ttcccaacct taccagaggg cgccccagct ggcaattccg acgtctaagg     60
aaccattatt atcgtgacat taacctataa aaataggcgt atcacgaggc cctttcgcct    120
ccacctcgag tccctaccag tgatagggat tgacatccct atcagtgata gaaatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 221
<211> LENGTH: 372
<212> TYPE: DNA
<213> ORGANISM: Artificial
<220> FEATURE:
<223> OTHER INFORMATION: mutant sequence of bacteriophage lambda tet0
      promoter
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 221 ttnnnnggge ttcccaacct taccagaggg cgccccagct ggcaattccg acgtctaaga     60
aaccattatt atcatgacat taacctataa aaataggcgt atcacgaggc cctttcgtct    120
```

```
tcacctcgag tccctatcag tgatagagat tgacatccct atcagtggta gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                       372
```

<210> SEQ ID NO 222
<211> LENGTH: 372
<212> TYPE: DNA
<213> ORGANISM: Artificial
<220> FEATURE:
<223> OTHER INFORMATION: mutant sequence of bacteriophage lambda tet0 promoter
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 222

```
ttnnnngggc ttcccaacct taccagaggg cgccccagct ggcaattccg acgtctaaga    60
aaccactatt atcatgacat taacctataa gagtaggcgt atcacgaggc cctttcgtct   120
tcacctcgag tccctgtcag tgatagagat tgacatccct atcagtgata gagatactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                      372
```

<210> SEQ ID NO 223
<211> LENGTH: 347
<212> TYPE: DNA
<213> ORGANISM: Artificial
<220> FEATURE:
<223> OTHER INFORMATION: mutant sequence of bacteriophage lambda tet0 promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t

<400> SEQUENCE: 223

```
tttgcngggc ttcccaacct taccagaggg cgccccagct ggcaattccg acgtctaaga    60
aaccattatt atcatgacat taacctataa aaataggcgt atcacgaggc cctttcgtct   120
tcacctcgag tccctatcag tgatagagat actgagcaca tcagcaggac gcactgaccg   180
aattcattaa agaggagaaa ggtaccgcat gcgtaaagga agaactttt cactggagt   240 tgtcccaatt cttgttgaat tagatggtga tgttaatggg cacaaattt ctgtcagtgg   300 agagggtgaa ggtgatgcaa catacggaaa acttacccct aanttta               347
```

<210> SEQ ID NO 224
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 224
tttgcngggc ttcccaacct taccagaggg cgccccagct ggcaattccg acgtctaaga    60
aaccattatt atcatgacat taacctataa aaataggcgt atcacgaggc cctttcgtct   120
tcacctcgag tccctatcag tgatagagat tgacatccct atcagtgata gagacactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                      372

<210> SEQ ID NO 225
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 225
ttnnnnnggc ttcccaacct taccagaggg cgccccagct ggcaattccg acgtctaaga    60
aaccattatt atcatgacat taacctataa aaataggcgt atcacgaggc cctttcgttt   120
tcacctcgag tccccatcag tgacagagat tgacatccct atcagtgata gagacactga   180
gcacatcagc aggacgcact gaccgaattc attaaagagg agaaaggtac cgcatgcgta   240
aaggagaaga acttttcact ggagttgtcc caattcttgt tgaattagat ggtgatgtta   300
atgggcacaa attttctgtc agtggagagg gtgaaggtga tgcaacatac ggaaaactta   360
cccttaantt ta                                                      372

<210> SEQ ID NO 226
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t -continued

<400> SEQUENCE: 226

```
tttgcngggc ttcccaacct taccagaggg cgccccagct ggcaattccg acgtctaagg     60
gaccattatt atcatgacat taacctataa aaataggcgt atcacgaggc cctttcgtct    120
tcacctcgag tccctatcag tgatagagat tgacatccct atcagtgata gaaatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                       372
```

<210> SEQ ID NO 227
<211> LENGTH: 372
<212> TYPE: DNA
<213> ORGANISM: Artificial
<220> FEATURE:
<223> OTHER INFORMATION: mutant sequence of bacteriophage lambda tetO promoter
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 227

```
ttnnnnnggc ttcccaacct taccagaggg cgccccagct ggcaattccg acgtctaaga     60
aaccattatc atcatgacat taacctataa aaataggcgt atcacgaggc cctttcgtct    120
tcacctcgag tccctatcag tgacagagat tgacatccct atcagtggta gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                       372
```

<210> SEQ ID NO 228
<211> LENGTH: 372
<212> TYPE: DNA
<213> ORGANISM: Artificial
<220> FEATURE:
<223> OTHER INFORMATION: mutant sequence of bacteriophage lambda tetO promoter
<220> FEATURE:
<221> NAME/KEY: misc_feature
<222> LOCATION: (3)..(7)
<223> OTHER INFORMATION: n is a, c, g, or t

<400> SEQUENCE: 228

```
ttnnnnnggc ttcccaacct taccagaggg cgccccagct ggcaattccg acgtctgaga     60
aaccattatt atcataacat taacctataa agataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaaatt ta                                                       372
```

```
<210> SEQ ID NO 229
<211> LENGTH: 372
<212> TYPE: DNA
<213> ORGANISM: Artificial
<220> FEATURE:
<223> OTHER INFORMATION: mutant sequence of bacteriophage lambda tetO
      promoter
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t

<400> SEQUENCE: 229
tttgcngggc ttcccaacct taccagaggg cgccccagct ggcaattccg acgtctaagg      60
aaccattatt gtcatgacat taacctataa aaataggcgt atcacgaggc cctttcgtct    120
tcacctcgag tccctatcag tgatagagat tgacatccct atcagtgata gagatactga    180
gcacatcagc aggacgcact gaccgaattc attaaagagg agaaaggtac cgcatgcgta    240
aaggagaaga acttttcact ggagttgtcc caattcttgt tgaattagat ggtgatgtta    300
atgggcacaa attttctgtc agtggagagg gtgaaggtga tgcaacatac ggaaaactta    360
cccttaantt ta                                                        372

<210> SEQ ID NO 230
<211> LENGTH: 47
<212> TYPE: DNA
<213> ORGANISM: Artificial
<220> FEATURE:
<223> OTHER INFORMATION: mutant sequence of bacteriophage lambda tetO
      promoter

<400> SEQUENCE: 230
attgggacaa caccagtgaa taattcttca cctttagaca tttttct                   47

<210> SEQ ID NO 231
<211> LENGTH: 48
<212> TYPE: DNA
<213> ORGANISM: Artificial
<220> FEATURE:
<223> OTHER INFORMATION: mutant sequence of bacteriophage lambda tetO
      promoter

<400> SEQUENCE: 231
acgccaagcg cgcaattaac cctcactaaa gggaacaaaa gctggagc                  48
```